US009040684B2

(12) United States Patent
Buchanan et al.

(10) Patent No.: US 9,040,684 B2
(45) Date of Patent: *May 26, 2015

(54) CELLULOSE INTERPOLYMERS AND METHOD OF OXIDATION

(71) Applicant: Eastman Chemical Company, Kingsport, TN (US)

(72) Inventors: Charles Michael Buchanan, Bluff City, TN (US); Norma Lindsey Buchanan, Bluff City, TN (US); Susan Northrop Carty, Kingsport, TN (US); Chung-Ming Kuo, Kingsport, TN (US); Juanelle Little Lambert, Gray, TN (US); Michael Orlando Malcolm, Kingsport, TN (US); Jessica Dee Posey-Dowty, Kingsport, TN (US); Thelma Lee Watterson, Kingsport, TN (US); Matthew Davie Wood, Gray, TN (US); Margaretha Soderqvist Lindblad, Vallentuna (SE)

(73) Assignee: EASTMAN CHEMICAL COMPANY, Kingsport, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/728,232

(22) Filed: Dec. 27, 2012

(65) Prior Publication Data

US 2013/0116426 A1   May 9, 2013

Related U.S. Application Data

(60) Continuation of application No. 12/975,440, filed on Dec. 22, 2010, which is a division of application No. 10/995,750, filed on Nov. 23, 2004, now Pat. No. 7,879,994.

(60) Provisional application No. 60/525,787, filed on Nov. 28, 2003.

(51) Int. Cl.
| C08B 15/04 | (2006.01) |
| C08B 15/02 | (2006.01) |
| C08B 3/22 | (2006.01) |
| C08B 3/06 | (2006.01) |
| A61K 9/20 | (2006.01) |
| A61K 9/48 | (2006.01) |
| A61K 47/38 | (2006.01) |
| C08B 3/04 | (2006.01) |
| C08B 3/16 | (2006.01) |
| C08B 3/24 | (2006.01) |
| C08L 1/10 | (2006.01) |
| C08L 1/12 | (2006.01) |
| C08L 1/14 | (2006.01) |
| C09D 17/00 | (2006.01) |
| C08B 3/08 | (2006.01) |
| A61K 9/19 | (2006.01) |
| A61K 9/28 | (2006.01) |

(52) U.S. Cl.
CPC ... *C08B 3/06* (2013.01); *A61K 9/19* (2013.01); *A61K 9/2054* (2013.01); *A61K 9/2866* (2013.01); *A61K 9/4891* (2013.01); *A61K 47/38* (2013.01); *C08B 3/04* (2013.01); *C08B 3/16* (2013.01); *C08B 3/22* (2013.01); *C08B 3/24* (2013.01); *C08L 1/10* (2013.01); *C08L 1/12* (2013.01); *C08L 1/14* (2013.01); *C09D 17/00* (2013.01); *C08B 15/02* (2013.01); *C08B 15/04* (2013.01); *C08B 3/08* (2013.01)

(58) Field of Classification Search
USPC .............................................. 536/63, 64, 76
See application file for complete search history.

(56) References Cited

U.S. PATENT DOCUMENTS

| 2,363,091 A | 11/1944 | Seymour et al. |
| 2,758,111 A | 8/1956 | Roth |
| 3,414,640 A | 12/1968 | Garetto et al. |
| 3,489,743 A | 1/1970 | Crane |
| 3,845,770 A | 11/1974 | Theeuwes et al. |
| 3,859,228 A | 1/1975 | Morishita et al. |
| 3,916,899 A | 11/1975 | Theeuwes et al. |
| 3,977,404 A | 8/1976 | Theeuwes |
| 4,327,725 A | 5/1982 | Cortese et al. |
| 4,474,846 A | 10/1984 | Doerer et al. |

(Continued)

FOREIGN PATENT DOCUMENTS

| CH | 146 541 | 4/1931 |
| CH | 150 525 | 10/1931 |

(Continued)

OTHER PUBLICATIONS

EPO machine translation of FR 2831171 A1, http://worldwide.espacenet.com, accessed online on Oct. 2, 2013.*
Paquette, L.A., Encyclopedia of Reagents for Organic Synthesis, 1995, John Wiley & Sons Ltd., vol. 5, p. 3221-3223.*
Benaglia et al., Chem. Rev., 2003, 103(9), p. 3401-3430, Publication Date (Web): Jul. 4, 2003.*
Invitation to Pay Additional Fees from the International Searching Authority, date of mailing Mar. 30, 2005received in International Application No.PCT/US2004/039390.

(Continued)

*Primary Examiner* — Jonathan S Lau
(74) *Attorney, Agent, or Firm* — Steven Owen; Polly Owen

(57) ABSTRACT

This invention provides cellulose ester interpolymers, and methods of oxidizing cellulose interpolymers and cellulose ester interpolymers. The invention also provides routes to access carboxylated cellulose ester derivatives with high acid numbers wherein the carboxyl group is attached directly to the cellulose backbone by a carbon-carbon bond. Through functionalization of an intermediate aldehyde, the corresponding cationic or zwitterionic cellulose ester derivatives can also be accessed. The interpolymers of the present invention have a number of end-use applications, for example, as binder resins in various types of coating compositions and as drug delivery agents.

12 Claims, 7 Drawing Sheets

(56) References Cited

U.S. PATENT DOCUMENTS

| | | |
|---|---|---|
| 4,590,265 A | 5/1986 | Bogan et al. |
| 4,627,850 A | 12/1986 | Deters et al. |
| 4,795,641 A | 1/1989 | Kashdan |
| 4,812,495 A | 3/1989 | Sand et al. |
| 4,839,113 A | 6/1989 | Villaine et al. |
| 4,894,448 A | 1/1990 | Pelzer |
| 4,906,579 A | 3/1990 | Yalpani et al. |
| 4,935,048 A | 6/1990 | Young |
| 4,960,814 A | 10/1990 | Wu et al. |
| 4,982,793 A | 1/1991 | Holtmyer et al. |
| 4,983,670 A | 1/1991 | Yates et al. |
| 4,985,553 A | 1/1991 | Fuertes et al. |
| 4,986,921 A | 1/1991 | Yates et al. |
| 5,008,385 A | 4/1991 | Diamantoglou |
| 5,055,230 A | 10/1991 | Clubley et al. |
| 5,067,565 A | 11/1991 | Holtmyer et al. |
| 5,122,549 A | 6/1992 | Holtmyer et al. |
| 5,134,229 A | 7/1992 | Saferstein et al. |
| 5,223,642 A | 6/1993 | Schonwalder |
| 5,252,117 A | 10/1993 | Young |
| 5,326,864 A | 7/1994 | Besemer et al. |
| 5,384,163 A | 1/1995 | Budde et al. |
| 5,414,079 A | 5/1995 | Banker et al. |
| 5,455,340 A | 10/1995 | Bernard et al. |
| 5,482,704 A | 1/1996 | Sweger et al. |
| 5,484,913 A | 1/1996 | Stilwell et al. |
| 5,484,914 A | 1/1996 | Skibida et al. |
| 5,492,560 A | 2/1996 | Fairchild |
| 5,501,772 A | 3/1996 | Elliott et al. |
| 5,501,773 A | 3/1996 | Elliott et al. |
| 5,502,178 A | 3/1996 | Gupta et al |
| 5,538,730 A | 7/1996 | Romeo et al. |
| 5,541,316 A | 7/1996 | Engelskirchen et al. |
| 5,559,171 A | 9/1996 | Buchanan et al. |
| 5,567,277 A | 10/1996 | Elliott et al. |
| 5,594,068 A | 1/1997 | Buchanan et al. |
| 5,599,858 A | 2/1997 | Buchanan et al. |
| 5,599,977 A | 2/1997 | Kiely et al. |
| 5,647,956 A | 7/1997 | Elliott et al. |
| 5,662,773 A | 9/1997 | Frederick et al. |
| 5,668,273 A | 9/1997 | Allen et al. |
| 5,676,964 A | 10/1997 | Della Valle et al. |
| 5,679,146 A | 10/1997 | Kalt et al. |
| 5,695,694 A | 12/1997 | Iwata et al. |
| 5,696,101 A | 12/1997 | Wu et al. |
| 5,698,688 A | 12/1997 | Smith et al. |
| 5,772,013 A | 6/1998 | Kunz et al. |
| 5,776,394 A | 7/1998 | Schrott et al. |
| 5,780,618 A | 7/1998 | Banker et al. |
| 5,789,571 A | 8/1998 | Beavers et al. |
| 5,792,856 A | 8/1998 | Allen et al. |
| 5,804,296 A | 9/1998 | Itoh et al. |
| 5,820,636 A | 10/1998 | Angstmann et al. |
| 5,821,360 A | 10/1998 | Engelskirchen et al. |
| 5,831,043 A | 11/1998 | Fleche |
| 5,834,095 A | 11/1998 | Dutkiewicz et al. |
| 5,856,470 A | 1/1999 | Moeller et al. |
| 5,883,025 A | 3/1999 | Karstens et al. |
| 5,885,412 A | 3/1999 | Paart et al. |
| 5,892,027 A | 4/1999 | Moeller et al. |
| 5,906,894 A | 5/1999 | West et al. |
| 5,914,003 A | 6/1999 | Kosowski et al. |
| 5,916,798 A | 6/1999 | Lund et al. |
| 5,929,229 A | 7/1999 | Edgar et al. |
| 5,959,101 A | 9/1999 | Engelskirchen et al. |
| 5,970,988 A | 10/1999 | Buchanan et al. |
| 5,973,139 A | 10/1999 | Lee et al. |
| 5,994,530 A | 11/1999 | Posey-Dowty et al. |
| 5,997,790 A | 12/1999 | Vos et al. |
| 6,022,614 A | 2/2000 | Aubry et al. |
| 6,025,007 A | 2/2000 | Krawczyk |
| 6,036,913 A | 3/2000 | Shibue et al. |
| 6,093,490 A | 7/2000 | Meraldi et al. |
| 6,111,097 A | 8/2000 | Nagashima et al. |
| 6,114,037 A | 9/2000 | Vos et al. |
| 6,123,172 A | 9/2000 | Byrd et al. |
| 6,129,867 A | 10/2000 | Chevalier et al. |
| 6,130,328 A | 10/2000 | Shimpo et al. |
| 6,132,759 A | 10/2000 | Schacht et al. |
| 6,133,439 A | 10/2000 | Buchanan et al. |
| 6,165,493 A | 12/2000 | Neurath et al. |
| 6,183,596 B1 | 2/2001 | Matsuda et al. |
| 6,184,272 B1 | 2/2001 | Foelster et al. |
| 6,211,358 B1 | 4/2001 | Honda et al. |
| 6,224,663 B1 | 5/2001 | Cantiani et al. |
| 6,228,126 B1 | 5/2001 | Cimecioglu et al. |
| 6,231,657 B1 | 5/2001 | Cantiani et al. |
| 6,235,931 B1 | 5/2001 | Wang et al. |
| 6,241,780 B1 | 6/2001 | Arkens et al. |
| 6,241,851 B1 | 6/2001 | Marcoccia |
| 6,254,724 B1 | 7/2001 | Seltzer et al. |
| 6,261,689 B1 | 7/2001 | Meraldi et al. |
| 6,310,200 B1 | 10/2001 | Vermaas |
| 6,335,464 B1 | 1/2002 | Ochi et al. |
| 6,368,456 B1 | 4/2002 | Cimecioglu et al. |
| 6,369,023 B1 | 4/2002 | Rodrigues et al. |
| 6,379,494 B1 | 4/2002 | Jewell et al. |
| 6,409,881 B1 | 6/2002 | Jaschinski |
| 6,440,547 B1 | 8/2002 | Luo et al. |
| 6,479,467 B1 | 11/2002 | Buchanan et al. |
| 6,495,190 B1 | 12/2002 | Yaginuma et al. |
| 6,498,269 B1 | 12/2002 | Merbouh et al. |
| 6,518,419 B1 | 2/2003 | Van Der Lugt et al. |
| 6,524,348 B1 | 2/2003 | Jewell et al. |
| 6,559,912 B2 | 5/2003 | Aminaka |
| 6,562,195 B2 | 5/2003 | Cimecioglu et al. |
| 6,586,212 B1 | 7/2003 | Buchanan et al. |
| 6,586,588 B1 | 7/2003 | Cimecioglu et al. |
| 6,596,809 B2 | 7/2003 | Charmot et al. |
| 6,608,229 B2 | 8/2003 | Bragd et al. |
| 6,610,671 B2 | 8/2003 | Buchanan et al. |
| 6,613,528 B2 | 9/2003 | Helbert et al. |
| 6,627,749 B1 | 9/2003 | Kumar |
| 6,627,750 B2 | 9/2003 | Wang |
| 6,635,755 B1 | 10/2003 | Jaschinski et al. |
| 6,695,950 B1 | 2/2004 | Cimecioglu et al. |
| 6,716,976 B1 | 4/2004 | Jetten et al. |
| 6,730,631 B1 | 5/2004 | Eberle et al. |
| 6,736,933 B2 | 5/2004 | Jewell et al. |
| 6,746,641 B1 | 6/2004 | Gunkel et al. |
| 6,770,755 B1 | 8/2004 | Gunnars et al. |
| 6,790,822 B1 | 9/2004 | Baba et al. |
| 6,793,686 B2 | 9/2004 | Cimecioglu et al. |
| 6,797,773 B1 | 9/2004 | Pagliaro et al. |
| 6,803,410 B2 | 10/2004 | Charmot et al. |
| 6,814,914 B2 | 11/2004 | Tasaka et al. |
| 6,821,383 B2 | 11/2004 | Shore et al. |
| 6,824,645 B2 | 11/2004 | Jaschinski et al. |
| 6,824,649 B2 | 11/2004 | Jewell et al. |
| 6,831,173 B1 | 12/2004 | Jetten et al. |
| 6,835,707 B1 | 12/2004 | Panandiker et al. |
| 6,844,066 B2 | 1/2005 | Hamed |
| 6,858,717 B1 | 2/2005 | Ball |
| 6,872,821 B2 | 3/2005 | Cimecioglu et al. |
| 6,875,861 B1 | 4/2005 | Besemer et al. |
| 6,894,160 B2 | 5/2005 | Capan et al. |
| 6,914,139 B2 | 7/2005 | Mukunoki et al. |
| 6,919,447 B2 | 7/2005 | Komen et al. |
| 6,936,710 B2 | 8/2005 | Bragd et al. |
| 6,939,961 B1 | 9/2005 | Schlesiger |
| 6,942,726 B2 | 9/2005 | Cook et al. |
| 6,974,608 B2 | 12/2005 | Shimizu et al. |
| 6,977,275 B2 | 12/2005 | Buchanan et al. |
| 6,984,730 B2 | 1/2006 | Yamada et al. |
| 6,986,828 B2 | 1/2006 | Jollez et al. |
| 6,987,181 B2 | 1/2006 | Jaschinski et al. |
| 7,001,483 B2 | 2/2006 | Severeid et al. |
| 7,007,752 B2 | 3/2006 | Reddy et al. |
| 7,008,887 B2 | 3/2006 | Rearick et al. |
| 7,026,303 B2 | 4/2006 | Cimiluca et al. |
| 7,026,470 B2 | 4/2006 | Obie |
| 7,030,179 B2 | 4/2006 | Patterson et al. |
| 7,030,187 B2 | 4/2006 | Charmot et al. |
| 7,037,441 B2 | 5/2006 | Offord |

(56) References Cited

U.S. PATENT DOCUMENTS

| | | |
|---|---|---|
| 7,052,540 B2 | 5/2006 | McCreight et al. |
| 7,086,935 B2 | 8/2006 | Wang |
| 7,098,193 B2 | 8/2006 | Myatt et al. |
| 7,109,325 B2 | 9/2006 | Komen et al. |
| 7,122,660 B1 | 10/2006 | Nakanishi et al. |
| 7,135,557 B2 | 11/2006 | Weerawarna et al. |
| 7,148,344 B2 | 12/2006 | Nakanishi et al. |
| 7,153,390 B2 | 12/2006 | Spence et al. |
| 7,153,904 B2 | 12/2006 | Richardson et al. |
| 7,156,952 B2 | 1/2007 | Ragnar |
| 7,208,593 B2 | 4/2007 | Yoshii et al. |
| 7,220,731 B2 | 5/2007 | Davidson et al. |
| 7,229,689 B2 | 6/2007 | Qin et al. |
| 7,230,049 B2 | 6/2007 | Weerawarna |
| 7,241,836 B2 | 7/2007 | Weerawarna |
| 7,247,722 B2 | 7/2007 | Cimedoglu et al. |
| 7,258,764 B2 | 8/2007 | Mauler |
| 7,259,257 B2 | 8/2007 | Schlesiger et al. |
| 7,262,181 B2 | 8/2007 | Zhang et al. |
| 7,282,091 B2 | 10/2007 | Hashimoto |
| 7,297,228 B2 | 11/2007 | Anderson et al. |
| 7,303,654 B2 | 12/2007 | Tokarz et al. |
| 7,306,832 B2 | 12/2007 | Tasaka et al. |
| 7,307,149 B2 | 12/2007 | Dhugga et al. |
| 7,348,371 B2 | 3/2008 | Mehta et al. |
| 7,348,424 B2 | 3/2008 | Miyazawa et al. |
| 7,357,987 B2 | 4/2008 | Hunter |
| 7,387,830 B2 | 6/2008 | Maul et al. |
| 7,393,905 B2 | 7/2008 | Weerawarna |
| 7,399,440 B2 | 7/2008 | Kazama et al. |
| 7,399,604 B2 | 7/2008 | Sasisekharan et al. |
| 7,456,265 B2 | 11/2008 | Narayan et al. |
| 7,462,260 B2 | 12/2008 | Spence et al. |
| 7,470,385 B2 | 12/2008 | Yamada |
| 7,481,848 B2 | 1/2009 | Nakazaki et al. |
| 7,485,719 B2 | 2/2009 | Abe et al. |
| 7,485,720 B2 | 2/2009 | Yamane et al. |
| 7,494,611 B2 | 2/2009 | Shimizu et al. |
| 7,513,973 B2 | 4/2009 | Stoyanov et al. |
| 7,514,552 B2 | 4/2009 | Yamasaki et al. |
| 7,517,675 B2 | 4/2009 | Vercauteren et al. |
| 7,521,127 B2 | 4/2009 | Oya |
| 7,524,933 B2 | 4/2009 | Dhugga et al. |
| 7,528,100 B2 | 5/2009 | Gunn et al. |
| 7,544,379 B2 | 6/2009 | Kawamura et al. |
| 7,569,078 B2 | 8/2009 | Legrand |
| 7,569,556 B2 | 8/2009 | Narayan et al. |
| 7,579,443 B2 | 8/2009 | Dhugga et al. |
| 7,585,387 B2 | 9/2009 | Day et al. |
| 7,585,905 B2 | 9/2009 | Shelton et al. |
| 7,589,051 B2 | 9/2009 | Erazo-Majewicz et al. |
| 7,595,392 B2 | 9/2009 | Kumar et al. |
| 7,604,852 B2 | 10/2009 | Oya |
| 7,608,689 B2 | 10/2009 | Harris et al. |
| 7,628,888 B2 | 12/2009 | Beckman et al. |
| 7,635,506 B2 | 12/2009 | Takagi |
| 7,638,293 B2 | 12/2009 | De Kreij et al. |
| 7,645,874 B2 | 1/2010 | Saferstein et al. |
| 7,649,086 B2 | 1/2010 | Belanger et al. |
| 7,649,089 B2 | 1/2010 | Kumar et al. |
| 7,649,090 B2 | 1/2010 | Skuratowicz et al. |
| 7,662,801 B2 | 2/2010 | Kumar et al. |
| 7,671,100 B2 | 3/2010 | Gaserod et al. |
| 7,671,101 B2 | 3/2010 | Gaserod et al. |
| 7,671,102 B2 | 3/2010 | Gaserod et al. |
| 7,678,187 B2 | 3/2010 | Boersma et al. |
| 7,678,558 B2 | 3/2010 | Comstock et al. |
| 7,683,038 B2 | 3/2010 | Bellini et al. |
| 7,686,921 B2 | 3/2010 | Hamed et al. |
| 7,687,477 B2 | 3/2010 | Mikkonen et al. |
| 2001/0034442 A1 | 10/2001 | Bragd et al. |
| 2002/0072598 A1 | 6/2002 | Besemer et al. |
| 2002/0086990 A1 | 7/2002 | Kumar et al. |
| 2002/0098317 A1 | 7/2002 | Jaschinski et al. |
| 2003/0051834 A1 | 3/2003 | Weerawarna et al. |
| 2003/0171458 A1 | 9/2003 | Buchanan et al. |
| 2005/0028292 A1 | 2/2005 | Weerawarna et al. |
| 2005/0028953 A1 | 2/2005 | Severeid et al. |
| 2005/0106686 A1 | 5/2005 | Jetten et al. |
| 2005/0121159 A1 | 6/2005 | Jetten et al. |
| 2007/0203335 A1 | 8/2007 | Huttermann et al. |
| 2008/0105393 A1 | 5/2008 | Basemer et al. |

FOREIGN PATENT DOCUMENTS

| | | |
|---|---|---|
| CN | 186427 A | 12/2006 |
| DE | 516 462 | 1/1931 |
| DE | 874 440 | 4/1953 |
| EP | 0979826 A1 | 2/2000 |
| EP | 1077221 A1 | 2/2001 |
| FR | 2831171 | 4/2003 |
| GB | 568439 | 4/1945 |
| GB | 2314840 A | 1/1998 |
| WO | WO 9116357 A1 | 10/1991 |
| WO | WO 96/38484 A1 | 12/1996 |
| WO | WO 9923240 A1 | 5/1999 |
| WO | WO 9957158 A1 | 11/1999 |
| WO | WO 00/50463 | 8/2000 |
| WO | WO 0050621 A2 | 8/2000 |
| WO | WO 01/05377 A1 | 1/2001 |
| WO | WO 0100681 A1 | 1/2001 |
| WO | WO 0134657 A1 | 5/2001 |

OTHER PUBLICATIONS

Rouse, Ben P., "Cellulose Derivatives", Kirk-Othmer Encyclopedia of Chemical Technology, vol. 4, 1964, pp. 616-683.
Edgar, Kevin J. et al, Prog. Polym. Sci. 2001, 26, pp. 1605-1688.
Buchanan, Charles M. et al, Macromolecules 1992, 24, pp. 3050-3059, and pp. 360-3064.
Sand, I.D., Polymer Material Science Engineering, 1987, pp. 57-63.
Sosnovsky, G. et al, Synthesis, 1976, pp. 735-736.
Ma, Zhenkun et al, J. Org. Chem., 1991, 56, pp. 6110-6114.
Melvin, Fiona et al, Tetrahedron Letters, 1999, 40, pp. 1201-1202.
De Nooy, A.E.J. et al, Macromolecules, 1996, 29, pp. 6541-6547.
De Nooy, A.E.J. et al, Tetrahedron 1995, 51, pp. 8023-8032.
Sierakowski, M.R. et al, Carbohydrate Polymers, 2000, 42, pp. 51-57.
Jiang, Bo et al, Carbohydrate Research, 2000, 327, pp. 455-461.
De Nooy, Arjan E.J. et al, Carbohydrate Research, 1995, 269, pp. 89-98.
De Nooy, A.E.J. et al, Recl. Trav. Chim. Pays-Bas, 1994, 113, pp. 165-166.
Thaburet, Jean-Francois et al, Carbohydrate Research, 2001, 330, pp. 21-29.
Chang, Pahn S. et al, Carbohydrate Letters, 1998, 3, pp. 31-38.
Schnatbaum, Karsten et al, Synthesis, 1999, 5, pp. 864-872.
Brochette-Lemoine, Sandrine et al, Journal of Molecular Catalysis A: Chem. 1999, 150, pp. 31-36.
Bragd, Petter L. et al. Carbohydrate Research 2000, 328, pp. 355-363.
Bragd, Petter L. et al, Journal of Molecular Catalysis A: Chem., 2001, 170, pp. 35-42.
Hochkar, H. et al, Journal of Catalysis. 2000, 194, pp. 343-351.
Ito, Kazunori et al, Proc. Electrochem. Soc., 1993, pp. 260-267.
Györgydeák, Zoltán et al, Carbohydrate Research, 1995, 268, pp. 85-92.
Kato, Yumiko et al, Cellulose, 2002, 9, pp. 75-81.
Isogai, Akira et al, Cellulose, 1998, 5, pp. 153-164.
Kirk-Othmer Encyclopedia of Chemical Technology, 2d Ed. vol. 11, pp. 613-615, 1966.
Kirk-Othmer Encyclopedia of Chemical Technology, 2d Ed., vol. 11, pp. 621-623, 1996.
Kawamura, Tatsuyoshi et al, The Journal of Experimental Medicine, 2000, 192, pp. 1491-1500.
Neurath, A. Robert et al, BMC Infectious Diseases, 2002, 2:6 pp. 1-13.
Neurath, A. Robert et al, BMC Infectious Diseases, 2001, 1:17 pp. 1-12.
Manson, Kelledy H. et al, Antimicrobial Agents and Chemotherapy, 2000, 44, pp. 3199-3202.

(56) References Cited

OTHER PUBLICATIONS

Busso, Mariano E. et al, Antimicrobial Agents and Chemotherapy, 1990, 34, pp. 1991-1995.
T. Heinze et al., "The first on a convenient synthesis of novel reactive amphiphilic polysaccharides", Macromol. Rapid Commun., 17, 1996, pp. 675-681.
W. Herrmann et al., "The selective catalytic oxidation of terminal alcohols: a novel four-component system with MTO as a catalyst", Journal of Organometallic Chemistry, 579, 199, pp. 404-407, 1999.
R. Rowe, "Materials used in the film coating of oral dosage forms", Materials Used in the Pharmaceutical Formulation, Edited by A.T. Florence, pp. 1-36, 1984.
P. Chang et al., "Oxidation of Primary Alcohol Groups of Naturally Occurring Polysaccharides with 2,2,6,6-Tetramethyl-l-Piperidine", J. Carbohydrate Chemistry, 15(7) 1996, pp. 819-830.
C. Buchanan et al., "Preparation and Characterization of Cellulose Monoacetates: The Relationship between Structure and Water Solubility", Macromolecules, 1991, 24, pp. 3060-3064.
A. Cecchetto et al., "Efficient Mn-Cu and Mn-Co-TEMPO-catalysed oxidation of alcohols into aldehydes and ketones by oxygen under mild conditions", Tetrahedron Letters, 42, 2001, pp. 6651-6653.
J. Celia et al., "Nitroxide-Catalyzed Oxidation of Alcohols Using m-Chloroperbenktoic Acid. A New Method", J. Org. Chem., vol. 40, No. 12, 1975, pp. 1860-1862.
K. Walker, "Neue Aspekte des Naβ-in-Naβ-Lackierens", Farbe und Lack, v. 87, 1981, pp. 198-200 (abstract).
G. Tocco et al., "La formilcellulosa", Goirnale di Chimica Industriale ed Applicata, v. 13, 1931, pp. 325-330 (abstract).
B. Philipp et al., "Untersuchungen zur sulfatierung von celluloseforrniat im vergleich zu cellulose-acetat unter homogenen reaktionsbedingungen", Cellulose Chem. Technol., 24, 1990, pp. 667-678.
K. Ito et al., "Catalytic Oxidation of Sugars by 4-(Acetylamino)-TEMPO", Proceedings-Electrochemical Society, 1993, Coden: Pesodo, ISSN: 0161-6374.
A. de Nooy et al., "On the Use of Stable Organic Nitroxyl Radicals for the Oxidation of Primary and Secondary Alcohols", Synthesis, 1996, vol. 10, pp. 1153-1176.
Heuser, "Cellulose Esters with Other Organic Acids—Formyl Cellulose (Cellulose Formates)", The Chemistry of Cellulose, Publisher: John Wiley and Sons, Inc., pp. 284-286, 1944.
C. Malm et al., "Primary Hydroxyl Groups in Hydrolyzed Cellulose Acetate", Journal of the American Chemical Society, 1950, 72(6), pp. 2674-2678.
T. Heinze et al., "New Polymers Based on Cellulose", Lenzinger Berichte, 2000, 79, pp. 39-44, CODEN: LEBEAW, ISSN: 0024-0907.
T. Fujimoto et al., "Reaction of Cellulose with Formic Acid and Stability of Cellulose Formate" Journal of Polymer Science Part C: Polymer Letters, ISSN: 08876258, vol. 24, Issue 10, Oct. 1986, pp. 495-501.
Notification of Transmittal of the International Search Report and the Written Opinion of the International Searching Authority or the Declaration, date of mailing May 7, 2005, received in International Application No. PCT/US2004/039390.
A.M. Wilimbe et al., "Preparation of Oxidised Cellulose BP", Research and Industry, vol. 23, Sep. 1978, pp. 162-165.
C. Bertocchi et al., "Synthesis and Characterisation of Polyglucuronan", Carbohydrate Polymers, 27, (1995) pp. 295-297.
E.V. Gert et al., "Preparation of Powdered Oxycellulose in Nitric Acid", Polymer Science Ser., A, vol. 37, No. 7, 1995, pp. 670-675.
Th. Heinze et al., "Properties and following reactions of homogeneously oxidized celluloses", Cellulosics: Chemical, biochemical and material aspects, J.F.K., G.O. Philips and P.A. Williams (editors): 349-354, Ellis Norwood, New York, (1993).
E.C. Yackel et al., "The Oxidation of Cellulose by Nitrogen Dioxide", J. Am. Chem. Soc. 1942, 64, pp. 121-127.
E.J. Strojny, et al., "Oxidation of 2-Methoxyethanol to Methoxyacetic Acid by Nitric Acid Solutions", J. Am Chem. Soc., 1971, 93, pp. 1171-1178.
Y. Ogata, "Oxidations with Nitric Acids or Nitrogen Oxides", pp. 313-315. Oxidation in Organic Chemistry, Part C, W.S. Trahanovsky, editor, 1978.
T.P. Nevell, "The Oxidation of Cotton Cellulose by Nitrogen Dioxide", The Journal of the Textile Institute, Mar. 1951, 42, pp. T91-T129.
C. Mercer et al., "Keto Groups in Cellulose and Mannan Oxidized by Dinitrogen Tetroxide", Carbohydrate Research, 1970, 14, pp. 109-113.
T.J. Painter, "Preparation and Periodate Oxidation of C-6-Oxycellulose: Conformational Interpretation of Hemiacetal Stability", Carbohydrate Research, 1997, 55, pp. 95-103.
A.C. Besemer, et al., "Autocatalytic oxidation of primary hydroxyl functions in glucans with nitrogen oxides" Carbohydrate Research, 1997, 304, pp. 117-123.
V. Kumar et al., "HNO3/H3PO4-NANO2 mediated oxidation of cellulose—preparation and characterization of bioabsorbable oxidized celluloses in high yields and with different levels of oxication", Carbohydrate Polymers, 2002. 48, pp. 403-412.
M.L., Wolfrom et al., "Alkaline Hypochlorite Oxidation of Cellulose Anagogs", Tappi, Apr. 1964, vol. 47, No. 4, pp. 189-192.
M. Lewin, "Bleaching and Oxidation of Cellulose Hypobromite and Hypochlorite-Bromide Solutions" Tappi, Jun. 1965, vol. 48, No. 6, pp. 333-343.
S.K. Chakrabartty, "Alkaline Hypohalite Oxidations", pp. 344-348. Oxidation in Organic Chemistry, Part C, W.S. Trahanovsky, editor. 1978.
O.P. Singh, "Kinetics and Mechanism of Hypochlorite Oxidation of Cellulose", Textile Dryer & Printer, Feb. 17, 1982, pp. 35-38.
R.L. Whistler et al., "Action of Alkaline Hypochlorite on Corn Starch Amylose and Methyl 4-O-Mythyl-D-glucopyranosides", J. Am. Chem. Soc., 1956, 78, pp. 4704-4709.
R.L. Whistler et al., "Oxidation of Amylopectin with Hypochlorite at Different Hydrogen Ion Concentrations", J. Am. Chem. Soc., 1957, 79, pp. 6460-6464.
R.L. Whistler et al., "Oxidation of Alginic Acid with Hypochlorite at Differenct Hydrogen Ion Concentrations", J. Am. Chem. Soc., 1958, 80, pp. 5701-5704.
A.C. Besemer et al., "Dicarboxy-Starch by Sodium Hypochlorite/Bromide Oxidation and Its Calcium Binding Properties", Starch, 1994, 46, pp. 95-101.
A.E.J. de Nooy et al., "TEMPO-Medicated Oxidation of Pullulan and Influence of Ionic Strength and Linear Charge Density on the Dimensions of the Obtained Polyelectrolyte Chains", Macromolecules, 1996, 29, pp. 6541-6547.
P.L. Bragd et al., "Bromide-free TEMPO-mediated oxidation of primary alcohol groups in starch and methyl α-D-glucopyranoside", Carbohydrate Research 2000, 328, pp. 355-363.
Y. Kondo, "A convenient synthesis of methyl 4,6-O-benzylidene-α- and β-D-allo-pyranosideS", Carbohydrate Research, 1973, 30, pp. 386-389.
A.C. Besemer et al., "Methods for the Selective Oxidation of Cellulose: Preparation of 2,3-Dicarboxycellulose and 6-Carboxycellulose", pp. 73-82 Cellulose Derivatives Modification, Characterization, and Nanostructures. ACS Symposium Series 688, T.J. Heinze and W.G. Glasser, Editors, 1998.
P. Collins et al., "Monosaccharides" John Wiley & Sons, 1995, pp. 406-408.
B. Lindberg et al., "The Occurrence of 3-Oxoglucose Units in Oxidised Cellulose" Acta Chemica Scandinavica 1957, 11, pp. 1355-1358.
C. Tahiri et al., "TEMPO-oxidation of cellulose: Synthesis and characterisation of polyglucuronan", Cellulose, 2000, 7, pp. 177-188.
L. Gan et al., "Formylation of primary hydroxyl groups in sugars", Carbohydrate Research, 206, 1990, pp. 65-69.
T. Miyazawa et al., "Synthesis and Polymerization of 4-O-Vinylbenzyl-2,2,6,6-Tetramethylpiperidine", Journal of Polymer Science, Polymer Chemistry Edition, vol. 23, 1985, pp. 1527-1535.
H. Kern et al., "Synthesis, control of substitution pattern and phase transitions of 2,3-di-O-methylcellulose" Carbohydrate Research, 326, 2000, pp. 67-79.

(56) References Cited

OTHER PUBLICATIONS

T. Heinz et al., "p-Toluenesulfonyl esters in cellulose modifications: acylation of remaining hydroxyl groups", Macromol. Chem. Phys., 197, 1996, pp. 4207-4224.

W. Stevens et al., "Mixed Carboxylic Acid Anhydrides", 83, 1964, Recueil, pp. 1287-1293.

Klemm, D.O. "Regiocontrol in Cellulose Chemistry: Principles and Examples of Etherification and Esterification", T.J. Heinz and W.G. Glasser, Editors, 1998, Oxford University Press, pp. 19-37.

Klemm, D.O.: Heinze et al. Cellulose Derivatives, 1998, ACS Symposium, vol. 688, pp. 19-37.

M. Schnabelrauch et al., "Readily hydrolyzable cellulose esters as intermediates for the regioselective derivation of cellulose, 1—Synthesis and characterization of soluble, low substituted cellulose formats", Die Angewandte Makromolekulare Chemie, 198, 1992, pp. 155-164 (Nr. 3451).

V. Mehlenbacher, "Organic Analysis—Hydroxyl Groups", J. Mitchell Jr. I.M. Kolthoff. E.S. Proskauer, A. Weisberger, Editorial Board, vol. 1, pp. 37-38, 1953.

W. Stevens et al., "Mixed Carboxylic Acid Anhydrides", 83, 1964, Recueil, pp. 1294-1298.

S. Takahashi et al., "C-NMR Spectral Studies on the Distribution of Substituents in Some Cellulose Derivatives", Journal of Polymer Science: Part A: Polymer Chemistry Edition, vol. 24, 1986, pp. 2981-2993.

T. Nagai et al., "Chapter 3—Applications of HPMC and HPMCAS Aqueous Film Coating of Pharmaceutical Dosage Forms", Aqueous Polymeric Coatings for Pharmaceutical Dosage Forms, Edited by J. McGinity, pp. 81-152, 1989.

K. Schnatbaum et al., "Electroorganic Synthesis 66: Selective Anodic Oxidation of Carbohydrates Mediated by TEMPO", Synthesis, 1999, No. 5, pp. 864-872.

E.G. Rozantzev et al., "Organic Radical Reactions Involving No Free Valence", Tetrahedron, 1964, vol. 20 pp. 131-137.

B. Philipp et al., "Chapter 32—Homogeneous derivation of cellulose via reactive organo-soluble intermediates", Cellulose Sources and Exploitation—Industrial Utilization, Biotechnology and Physico—Chemical Properties, J.F. Kennedy et al., Editors, pp. 257-262, 1990.

R.H. Marchessaults et al., "Experimental Evaluation of the Lateral-Order Distribution in Cellulose", Textile Research Journal, 1957, 27, pp. 30-41.

C. Malm et al., "C. Organic Esters", Cellulose and Cellulose Derivatives, E. Ott et al., Editors, pp. 763-824, 1943.

T. Liebert et al., "Synthesis Path Versus Distribution of Functional Groups in Cellulose Ethers", Macromol, Symp., 130, 1998, pp. 271-283.

T. Liebert et al., "Synthesis and Carboxymethylation of Organo-Soluble Trifluoroacetates and Formates of Cellulose", J.M.S.—Pure Appl. Chem., A33(5), 1996, pp. 613-626.

T. Kondo, "Preparation of 6-O-alkylcelluloses", Carbohydrate Research 238, 1993, pp. 231-240.

T. Kondo et al., "The preparation of O-methyl-and-O-ethyl-celluloses having controlled distribution of substituents", Carbohydrate Research, 220, 1991, pp. 173-183.

T. Kondo, "Hydrogen Bonds in Regioselectively Substituted Cellulose Derivatives", Journal of Polymer Science: Part B: Polymer Science Physics, vol. 32, 1994, pp. 1229-1236.

D. Klemm et al., "Polyglucane Derivatives with Regular Substituent Distribution", Macromol, Symp., 99, 1995, pp. 129-140

D. Klemm et al., "Silylated Cellulose Materials in Design of Supramolecular Structures of Ultrathin Cellulose Films", J. M.S.—Pure Appl. Chem., A32(4), 1995, pp, 899-904.

Bertocchi et al. Carbohydrate Polymers, 1995, 27, pp. 295-297.

Tahiri et al. Cellulose, 2000, 7, pp. 177-188.

Kuznetsova. Russian Chemical Bulletin, 1979, 28(5), pp. 1029-1031.

Lemeune et al. Journal of Applied Polymer Sciences, 2004, 93, pp. 1219-122.

Daly et al. Water-Soluble Polymers, Shalaby, S. et al., ACS Symposium Series, 1991, p. 189-200.

USPTO Office Action for U.S. Appl. No. 12/975,440 dated Aug. 6, 2013.

USPTO Office Action for U.S. Appl. No. 13/728,153 dated Sep. 26, 2013.

USPTO Office Action for U.S. Appl. No. 13/728,216 dated Sep. 27, 2013.

USPTO Office Action for U.S. Appl. No. 13/728,258 dated Oct. 8, 2013.

USPTO Office Action for U.S. Appl. No. 13/728,187 dated Nov. 19, 2013.

Hall et al., Model Compounds of Cellulose: Trityl Ethers Substituted Exclusively at C-6 Primary Hydroxyls, Journal of Applied Polymer Science, Vo. 17, pp. 2891-2896. 1973.

Haskins et al, "Aminocellulose Derivatives", J. Org. Chem., vol. 19, Issue 1, pp. 67-69, 1954.

Hearon et al, Cellulose Trityl Ether, J. Am. Chem. Soc., vol. 65, pp. 2449-2452, 1943.

Klemm et al, "New approaches to advanced polymers by selective cellulose functionalization", Acta Polymer, 1997, 48, pp. 277-297.

Woodings, C. entry for Cellulose Fibers, Regenerated, Encyclopedia of Polymer Science and Technology, 2002, Wiley-Interscience, vol. 5.=, pp. 532-570.

USPTO Office Action for U.S. Appl. No. 13/728,258 dated May 8, 2014.

USPTO Notice of Allowance dated May 14, 2014 for co-pending U.S. Appl. No. 12/975,440.

USPTO Office Action for U.S. Appl. No. 13/728,153 dated Jun. 5, 2014.

USPTO Office Action for U.S. Appl. No. 13/728,216 dated Jun. 13, 2014.

USPTO Office Action for U.S. Appl. No. 13/728,187 dated Jun. 5, 2014.

MSDS for Formic Acid, Sigma-Aldrich, http://www.sigmaaldrich.com/, accessed online on Jun. 9, 2014.

* cited by examiner

Figure 7. Dissolution of poorly water-soluble drugs from oxidized CA:drug mixtures.
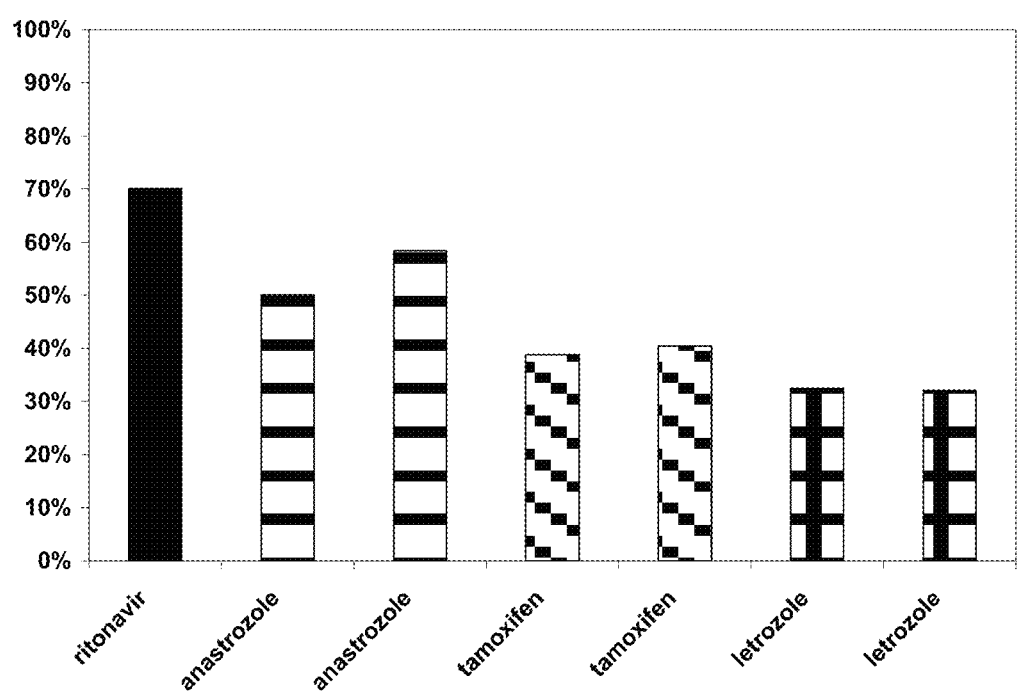

CELLULOSE INTERPOLYMERS AND METHOD OF OXIDATION

CROSS REFERENCE TO RELATED APPLICATION

This application is a continuation of U.S. application Ser. No. 12/975,440 filed on Dec. 22, 2010, now United States Publication No. 2011-0098464; which is a divisional of U.S. application Ser. No. 10/995,750 filed on Nov. 23, 2004, now U.S. Pat. No. 7,879,994; which claims benefit from the following provisional application under 35 USC 119: U.S. Application Ser. No. 60/525,787, filed Nov. 28, 2003, now expired; all of which are incorporated herein by reference.

FIELD OF THE INVENTION

This invention provides cellulose ester interpolymers, cellulose interpolymers, and methods of oxidizing cellulose interpolymers and cellulose ester interpolymers.

BACKGROUND OF THE INVENTION

Cellulose esters are well known compounds ("Cellulose Derivatives", Ben P. Rouse, Kirk-Othmer Encyclopedia of Chemical Technology, vol 4, 1964, 616-683). The most common cellulose esters are comprised of aliphatic $C_2$-$C_4$ substitutents. Examples of such cellulose esters include cellulose acetate (CA), cellulose propionate (CP), cellulose butyrate (CB), cellulose acetate propionate (CAP), and cellulose acetate butyrate (CAB). Examples of the utility of such cellulose esters can be found in Prog. Polym. Sci. 2001, 26, 1605-1688. Cellulose esters are generally prepared by first converting cellulose to a cellulose triester before hydrolyzing the cellulose triester in an acidic aqueous media to the desired degree of substitution (DS, the number of substitutents per anhydroglucose monomer). Aqueous acid catalyzed hydrolysis of cellulose triacetate yields a random copolymer that can consist of 8 different monomers depending upon the final DS (Macromolecules 1991, 24, 3050).

Processes that provide non-random copolymers via hydrolysis of cellulose triesters are known. Direct esterification to less than fully substituted cellulose esters is also known. Depending upon the precise reaction conditions, it is possible to obtain a non-random cellulose ester by this type of process.

Recently, there have been accounts of attempts at the preparation of regioselectively substituted cellulose derivatives. For the purposes of this invention, regioselective substitution means the exclusive or preferential placement or removal of a substituent at the C2, C3, or C6 hydroxyls of the anhydroglucose monomer of cellulose. Controlled placement of the substitutent can lead to a homopolymer or a copolymer of cellulose with specific monomer content. That is, a cellulose derivative with a specific substitution pattern within the anhydroglucose monomer and a controlled sequence along the cellulose polymer chain is obtained.

Prior methods leading to the formation of regioselective substituted cellulose derivatives rely on the use of temporary protecting groups and either requires the use of cellulose solvents so that the protecting group can be installed in a homogeneous reaction mixture or mercerized cellulose that has sufficient reactivity.

The preparation of certain formate esters of carbohydrates and polysaccharides is known. The isolated cellulose formates are typically used as unstable intermediates for subsequent reactions due to reported instability of the formate ester and reactivity toward other functional groups. As a result, the formation of mixed cellulose formate derivatives has received little attention, and few reports of the formation of a mixed cellulose formate esters exists. GB 568,439 (1945) teaches the preparation of cellulose acetate formate which is produced by mixing cellulose with an acetic and formic mixed anhydride in the presence of a catalyst Only a few classes of carboxylated cellulose esters are known. One example of this class of cellulose ester derivatives is carboxymethyl cellulose esters described for example in U.S. Pat. Nos. 5,668,273; 5,792,856; and 5,994,530. These cellulose derivatives are cellulose ether esters in which an intervening ether linkage attaches a carboxylate to the anhydroglucose units of the cellulose chain. These derivatives are formed by esterifying carboxymethyl cellulose (an ether) to the fully substituted carboxymethyl cellulose ester followed by hydrolysis to the desired ester DS. This class of carboxylated cellulose esters offers the advantage of a non-hydrolysable carboxylate linkage. The disadvantage is that the method of preparation is a two-step process requiring the preparation and isolation of the carboxymethyl cellulose prior to esterification. Furthermore, one cannot obtain a consistent, homogeneous distribution of carboxymethyl substitutents along the cellulose backbone.

Another class of carboxylated cellulose esters is those in which the carboxylate functionality is attached to the cellulose backbone via an ester linkage. An example of this class is cellulose acetate phthalate and the like which are described in U.S. Pat. No. 3,489,743. In general, these cellulose ester derivatives are formed by first preparing a neutral, randomly substituted cellulose ester, e.g. a CA, with the desired DS. In a second reaction, the carboxylate functionality is installed by treating the cellulose ester with an anhydride such as phthalic anhydride.

An additional class of carboxylated cellulose esters is those, which result from ozonolysis of cellulose esters in the solid state (Sand, I. D., Polymer Material Science Engineering, 1987, 57-63; U.S. Pat. No. 4,590,265). Ozonolysis of cellulose ester provides a polymer that contains not only carboxylates but also aldehydes, ketone, and peroxides as well. The process results in significant loss in polymer molecular weight and relatively low levels of oxidation. Furthermore, the process is not specific in that any of the cellulose ester hydroxyls can be oxidized.

Oxidation of carbohydrates and polysaccharides is a very important process in the chemical industry and a number of useful catalysts for this transformation have been developed. Some of the most useful catalysts belong to the class of compounds referred to as nitroxyl or nitroxide radicals. Typically, these compounds are secondary amine nitroxides with the general structure shown below.

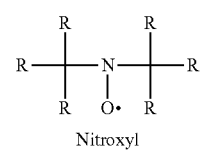

Nitroxyl

Of the secondary amine N-oxides, the cyclic hindered nitroxyls belonging to the piperidine series have proven to be the most interesting. There are many routes for the synthesis of cyclic nitroxyl derivatives in the piperidine series. The vast majority of the methods use 4-oxo-2,2,6,6-tetramethylpiperidine (triacetoneamine) as the common starting material, which is generally prepared by the cyclocondensation of acetone and ammonia (Sosnovsky, G.; Konieczny, M., Synthesis, 1976, 735-736). Triacetoneamine serves as a common intermediate for the synthesis of a number of different derivatives such as those shown in Scheme 1 below. Of the derivatives shown in Scheme 1,2,2,6,6-tetramethylpiperidine-N-oxyl (5, TEMPO) has proven to be the cyclic nitroxyl used in most studies involving oxidation of alcohols.

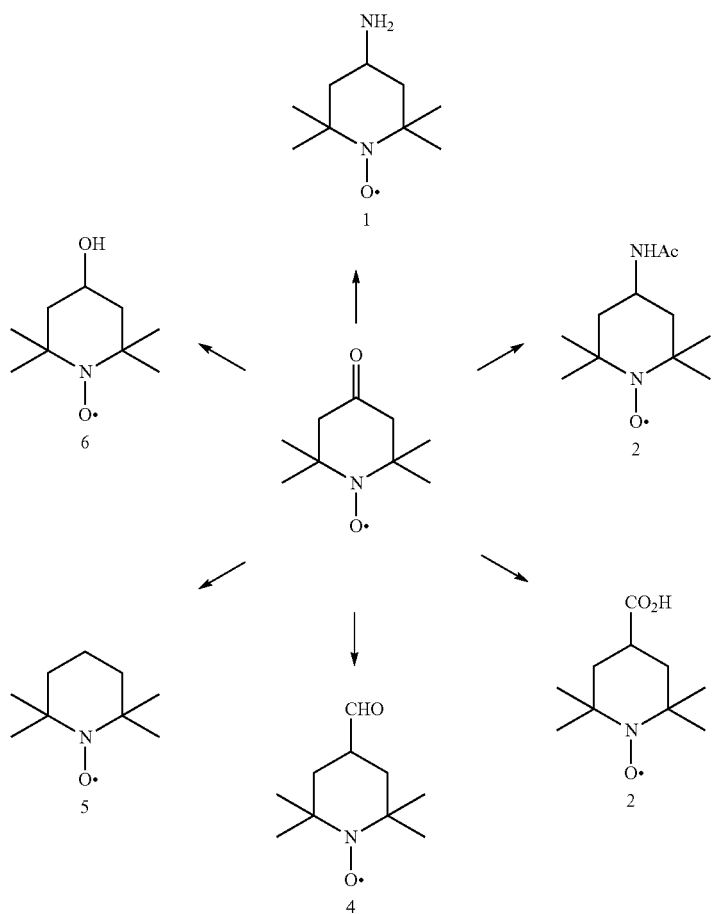

Scheme 1

Oxidation of alcohols with TEMPO under acidic conditions converts primary and secondary alcohols to aldehydes and ketones, respectively (Bobbit, J. M.; Ma, Z., J. Org. Chem. 1991, 56, 6110-6114). Generally, over oxidation is not observed, but two molar equivalents of TEMPO per mole of substrate are required for the oxidation of the alcohol. That is, the reaction is not catalytic.

The use of stoichiometric amounts of TEMPO or its analogues for oxidation of alcohols can be expensive and create difficulties in isolation of the product. As a result, work in this area has focused on catalytic processes that regenerate the nitrosonium ion in situ by the use of primary and/or terminal oxidants. The primary oxidant oxidizes the hydroxy amine back to the nitrosonium ion, and the terminal oxidant serves to regenerate the primary oxidant. In some cases, the primary oxidant functions as both the primary and terminal oxidant.

It is possible to oxidize alcohols under acidic conditions using catalytic amounts of TEMPO or its analogues. However, the solvents for this process are limited and acid sensitive substrates typically are destroyed under these conditions. Furthermore, primary and secondary alcohols are typically converted to aldehydes and ketones, respectively, rather than to a carboxylic acid.

TEMPO catalyzed oxidations of primary alcohols in non-aqueous reaction media under acidic conditions (pH<4) can give almost exclusively the corresponding aldehyde. In aqueous media, some subsequent conversion of the aldehyde to a carboxylate is observed, but the aldehyde to carboxylic acid ratio remains high. As a result, oxidation of primary alcohols of polysaccharides and carbohydrates under acidic conditions using prior art TEMPO catalyzed conditions is of limited utility due to the fact that the extent of oxidation is limited and the reaction media is not suitable for many substrates.

As a result, research concerning the oxidation of primary alcohols of polysaccharides and carbohydrates with TEMPO and TEMPO analogues has focused on oxidation under alkaline conditions. Because most polysaccharides and carbohydrates have limited solubility in organic solvents, most investigations have focused on the use of an aqueous reaction media.

Typical pH and temperature for TEMPO catalyzed oxidation of polysaccharides, such as starch, are in the range of 8.5-11.5 at a temperature of −10 to 25° C. (Tetrahedron Letters 1999, 40, 1201-1202; Macromolecules 1996, 29, 6541-6547; Tetrahedron 1995, 51, 8023-32; Carbohydr. Polym. 2000, 42, 51-57; Carbohydr. Res. 2000, 327, 455-461; Carbohydr. Res. 1995, 269, 89-98; WO 96/38484; Recl. Trav.

Chim. Pays-Bas 1994, 113, 165-6; Carbohydr. Res. 2001, 330, 21-29; Carbohydr. Lett. 1998, 3, 31-38; EP 1077221 A1; Synthesis 1999, 5, 864-872; J. Mol. Catal. A: Chem. 1999, 150, 31-36). In most cases, the primary oxidant is NaBr and the terminal oxidant is NaOCl.

Oxidation of polysaccharides and carbohydrates under alkaline conditions using analogues of TEMPO and other primary oxidants has also been investigated (Carbohydrate Research 2000, 328, 355-363; J. Mol. Catal. A: Chem. 2001, 170, 35-42; J. Catal. 2000, 194, 343-351; Proc. Electrochem. Soc. 1993, 260-7; Carbohydr. Res. 1995, 268, 85-92; EP 0979826 A1; U.S. Pat. No. 5,831,043; US 2001/0034442 A1).

It is difficult, if not impossible, to oxidize cellulose esters using TEMPO under alkaline conditions. One problem is that nearly all cellulose esters are insoluble in water. Additionally, the pH and temperatures commonly employed can lead to rapid and undesirable cleavage of the acyl substitutents. Furthermore, the polymer backbone is rapidly cleaved under these reaction conditions.

Most of the studies involving TEMPO catalyzed oxidation of polysaccharides have involved water-soluble polysaccharides or polysaccharides that are sufficiently reactive so that they can be treated as a suspension in $H_2O$. Attempts to extend TEMPO mediated oxidations to cellulose have met with limited success. Cellulose can be oxidized to a water-soluble polyuronic acid after mercerization in NaOH or after regeneration of the cellulose (Cellulose 2002, 9, 75-81; Cellulose 1998, 5, 153-164).

In view of the previous discussion, it would be useful to have routes to access carboxylated cellulose ester derivatives with high acid numbers wherein the carboxyl group is attached directly to the cellulose backbone by a carbon-carbon bond. Preferably, such a route would be versatile allowing access to carboxylated cellulose esters having a wide range of acid numbers. It would also be desirable that the carboxylates be randomly distributed within the cellulose ester polymer. Through functionalization of the intermediate aldehyde, the corresponding cationic or zwitterionic cellulose ester derivatives could also be accessed.

SUMMARY OF THE INVENTION

In one aspect, the present invention provides cellulose ester interpolymers wherein the C2 and C3 positions of each of the anhydroglucose units of the cellulose ester interpolymer are in the alcohol oxidation state, and comprising anhydroglucose units

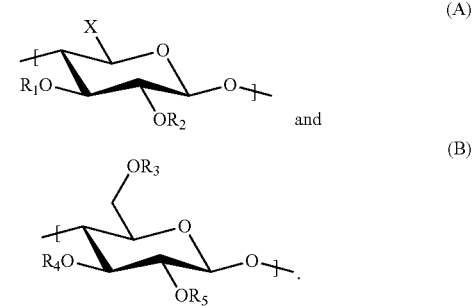

wherein $R_1$, $R_2$, $R_3$, $R_4$, and $R_5$ are independently selected from the group consisting of hydrogen and $C_2$-$C_{12}$ acyl groups, wherein at least one of $R_1$, $R_2$, $R_3$, $R_4$, and $R_5$ is a $C_2$-$C_{12}$ acyl group; and, X is formyl, hydroxymethylene, aminomethyl, $R_6$—NH—$CH_2$— or carboxy or a mixture thereof, wherein $R_6$ is selected from the group consisting of alkyl, aryl, or alkylene-aryl, provided when at least some of X is carboxy, the acid number is greater than 10; wherein the anhydroglucose units A and B comprise greater than 65% of the total anhydroglucose units of the cellulose portion of the cellulose ester interpolymer.

In another aspect, the present invention provides cellulose ester interpolymers comprising a plurality of anhydroglucose units having a C6 carboxy group and wherein the cellulose ester interpolymer has an apparent degree of substitution per anhydroglucose unit of $C_2$-$C_{12}$ acyl of at least about 0.6 and an acid number of greater than 10.

In another aspect, the present invention provides oxidized cellulose interpolymers having a degree of polymerization of at least 10, an acid number of greater than 10, and a random distribution throughout the cellulose interpolymer of anhydroglucose units having a C6 carboxy group.

In another aspect, the present invention provides cellulose ester interpolymers comprising anhydroglucose units

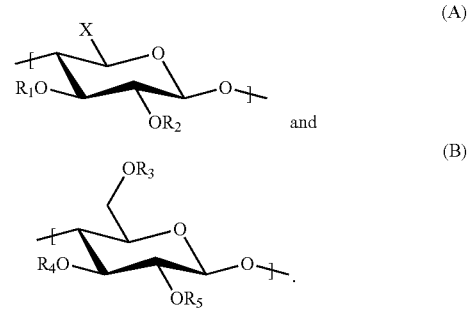

wherein $R_1$, $R_2$, $R_3$, $R_4$, and $R_5$ are independently selected from the group consisting of $C_2$-$C_{12}$ acyl groups; X is hydroxymethyl; and wherein the anhydroglucose units A and B comprise greater than 65% of the total anhydroglucose units of the cellulose portion of the cellulose ester interpolymer, and the degree of substitution per anhydroglucose unit of $C_2$-$C_{12}$ acyl groups is from about 1.5 to about 2.5.

In another aspect, the present invention provides cellulose ester interpolymers having a degree of substitution per anhydroglucose unit of formate of 0.5 to 1.3, and a degree of substitution of $C_2$-$C_{12}$ acyl of 1.5 to 2.5.

In another aspect, the present invention provides a method for converting a C6 hydroxyl of an anhydroglucose unit of cellulose polymer to a formyl group or a carboxyl group comprising: adding an amino substituted cyclic nitroxyl derivative, a primary oxidant, and a terminal oxidant to a cellulose mixture having a pH of less than 4 to form a reaction mixture, wherein the cellulose mixture comprises a $C_2$-$C_{12}$ alkyl acid, water, and a cellulose polymer comprising anhydroglucose units having C6 hydroxyl groups; and passing of a reaction period sufficient to effect conversion of a C6 hydroxyl to a formyl group or a carboxy group and thus produce an oxidized cellulose interpolymer. In a further embodiment, there is provided the above process, further comprising reacting the oxidized cellulose interpolymer with a $C_2$-$C_{12}$ acyl anhydride or a mixture thereof.

In another aspect, the present invention provides a method for converting a C6 hydroxyl of an anhydroglucose unit of a cellulose ester interpolymer to a formyl group or a carboxyl group comprising: adding an amino substituted cyclic nitroxyl derivative, a primary oxidant, and a terminal oxidant to a cellulose mixture having a pH of less than 4 to form a reaction mixture, wherein the cellulose mixture comprises a $C_2$-$C_{12}$ alkyl acid, water, and a cellulose ester interpolymer comprising anhydroglucose units having C6 hydroxyl groups; and passing of a reaction period sufficient to effect conversion of a C6 hydroxyl to a formyl group or a carboxy group and thus produce an oxidized cellulose ester interpolymer.

In a further aspect of the present invention, there is provided a method for preparing a stable form of a cellulose formate ester interpolymer comprising: (1) mixing formic acid, water, and an $C_2$-$C_{12}$ acyl anhydride to form a mixed anhydride mixture at a first contact temperature; (2) contacting the mixed anhydride mixture and a cellulose compound to form a reaction mixture at a second contact temperature; (3) adding an acid catalyst to the reaction mixture; (4) passing of a formylation period; wherein a resulting cellulose formate ester interpolymer has a degree of substitution per anhydroglucose unit of formate of about 0.5 to about 1.5.

In a further aspect of the invention, there is provided a method for preparing a stable form of a cellulose ester interpolymer comprising: (1) mixing formic acid, water, and an $C_2$-$C_{12}$ acyl anhydride to form a mixed anhydride mixture at a first contact temperature; (2) contacting the mixed anhydride mixture and a cellulose compound to form a reaction mixture at a second contact temperature; (3) adding an acid catalyst to the reaction mixture; (4) passing of a formylation period; (5) adding a $C_2$-$C_{12}$ acyl anhydride to the reaction mixture; (6) heating the reaction mixture to a third contact temperature; (7) passing of an acylation period; wherein a resulting cellulose ester interpolymer has a degree of substitution per anhydroglucose unit of $C_2$-$C_{12}$ acyl of about 1.5 to about 2.5, and a degree of substitution per anhydroglucose unit of formate of about 0.5 to about 1.5.

In another aspect, the present invention provides a method for converting a primary alcohol to a formyl, carboxylate, or mixture thereof, comprising: adding a 4-substituted piperidine nitroxyl derivative wherein the substituent is capable of hydrogen bonding, a primary oxidant, and a terminal oxidant to a mixture to form a reaction mixture, wherein the mixture has a pH of less than about 4 and comprises a compound comprising a primary alcohol functional group; passing of a reaction period sufficient to effect conversion of the primary alcohol functional group. In another embodiment, the primary oxidant is a Mn (III) salt.

In another aspect, the present invention provides a coating composition comprising anionic, cationic, or zwitterionic $C_2$-$C_{12}$ cellulose ester interpolymers; resins; organic solvents; and, optionally, pigments.

In another aspect, the present invention provides a waterborne coating composition comprising anionic, cationic, or zwitterionic $C_2$-$C_{12}$ cellulose ester interpolymers; resins; organic solvents; water; base; and, optionally, pigments.

In another aspect, the present invention provides a drug delivery composition comprising anionic, cationic, or zwitterionic $C_2$-$C_{12}$ cellulose ester interpolymers and a therapeutically active agent.

In another aspect, the present invention provides a therapeutic composition comprising anionic, cationic, or zwitterionic $C_2$-$C_{12}$ cellulose ester interpolymers wherein the oxidized cellulose ester is an effective agent in decreasing or preventing the frequency of transmission of the human immunodeficiency virus, herpes viruses, or sexually transmitted bacterial infections.

In another aspect, the present invention provides a thermoplastic composition comprising anionic, cationic, or zwitterionic $C_2$-$C_{12}$ cellulose ester interpolymers thermoplastic compatibilizers; one or more cellulose esters; a polymer; and, optionally, natural fibers.

In another aspect, the present invention provides a composite comprising anionic, cationic, or zwitterionic $C_2$-$C_{12}$ cellulose ester interpolymers thermoplastic compatibilizers; one or more neutral cellulose esters; and natural fibers.

In another aspect, the present invention provides a personal care composition comprising anionic, cationic, or zwitterionic $C_2$-$C_{12}$ cellulose ester interpolymers; resins; solvents; additives; and, optionally, pigments.

BRIEF DESCRIPTION OF DRAWINGS

FIG. 7 shows the dissolution of poorly water-soluble drugs from oxidized cellulose acetate: drug mixtures.

DETAILED DESCRIPTION OF THE INVENTION

It is to be understood that this invention is not limited to the specific methods, formulations, and conditions described, as such may, of course, vary. It is also to be understood that the terminology used herein is for the purpose of describing particular aspects only and is not intended to be limiting.

In this specification and in the claims that follow, reference will be made to a number of terms, which shall be defined to have the following meanings.

The singular forms "a," "an," and "the" include plural referents unless the context clearly dictates otherwise.

Ranges may be expressed herein as from "about" one particular value and/or to "about" or another particular value. When such a range is expressed, another aspect includes from the one particular value and/or to the other particular value. Similarly, when values are expressed as approximations, by use of the antecedent "about," it will be understood that the particular value forms another aspect.

Throughout this application, where patents are referenced, the disclosures of these patents in their entireties are hereby incorporated by reference into this application in order to more fully describe the state of the art to which this invention pertains.

Figure 1:
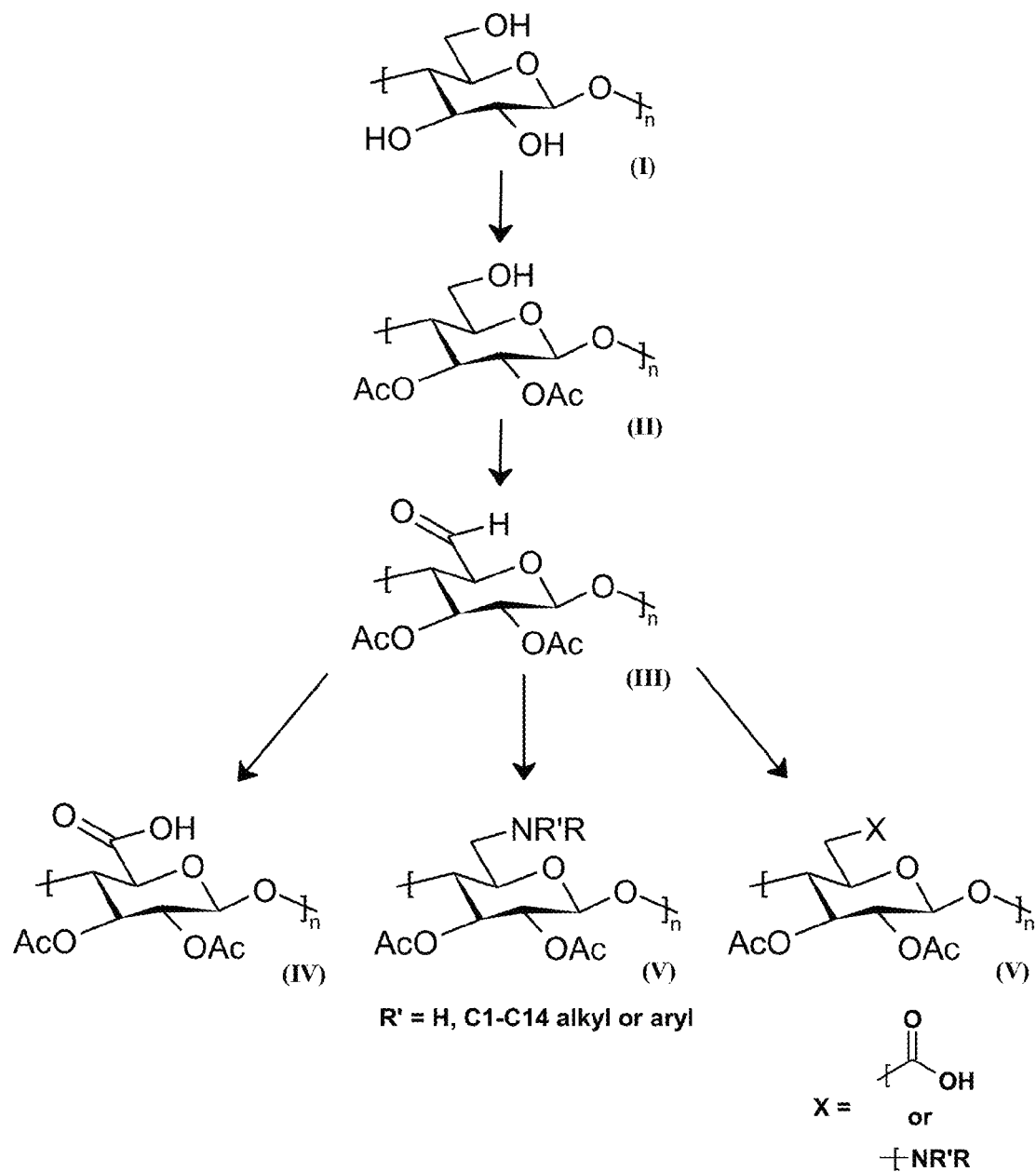
FIG. 1 is a scheme showing various synthetic routes.

As illustrated by FIG. 1, starting with native cellulose (I), one object of the invention is to form a fully substituted cellulose ester or mixed ester. Through selection of appropriate substitutents or reaction conditions, one can remove part or all of the acyl substitutent attached to the C6 primary hydroxyl. Following removal of the C6 substitutent, through the use of suitable catalysts and oxidants one can oxidize the cellulose ester in a mixture of carboxylic acid and water while maintaining the DS and molecular weight. The aldehyde (III) shown in FIG. 1 is a critical intermediate. By selection of suitable reaction conditions, the aldehyde may be oxidized to the carboxylate (IV) shown in FIG. 1. Further, we have found that it was possible to modify the reaction conditions such that the intermediate aldehyde could be intercepted with amines allowing the introduction of cationic functionality. This then leads to the cationic (V) or zwitterionic (VI) cellulose esters illustrated in FIG. 1. Although isolation of intermediates during this multi-step reaction is possible and in some instances desirable, in one embodiment, it is particularly desirable to convert the cellulose esters to oxidized cellulose esters without isolation of any intermediate derivatives.

We also desired to develop an alternative process by which cellulose could be activated and oxidized before esterifying to form an oxidized cellulose ester. Key to such a process would be activation of the cellulose in an acidic environment so that the cellulose chains were more evenly accessible. This would allow the oxidation to proceed in such a manner that a cellulose ester would ultimately be obtained with a high acid number and a relatively homogeneous distribution of oxidized C6 hydroxyls.

The cellulose triesters to be hydrolyzed and oxidized in the present invention can have three substituents selected independently from alkanoyls having from 2 to 10 carbon atoms. Examples of cellulose triesters include cellulose triacetate, cellulose tripropionate, and cellulose tributyrate or mixed triesters of cellulose such as cellulose acetate propionate, and cellulose acetate butyrate. These cellulose esters can be prepared by a number of methods known to those skilled in the art. For example, cellulose esters can be prepared by heterogeneous acylation of cellulose in a mixture of carboxylic acid and anhydride in the presence of a catalyst such as $H_2SO_4$. Cellulose triesters can also be prepared by the homogeneous acylation of cellulose dissolved in an appropriate solvent such as LiCl/DMAc or LiCl/NMP.

Those skilled in the art will understand that the commercial term of cellulose triesters also encompasses cellulose esters that are not completely substituted with acyl groups. For example, cellulose triacetate commercially available from Eastman Chemical Company, Inc., Kingsport, Tenn., U.S.A., typically has a DS from about 2.85 to about 2.95. Hence, cellulose triesters useful for the present invention means a cellulose ester having DS of at least 2.85.

After esterification of the cellulose to the triester, part of the acyl substituents are removed by hydrolysis or by alcoholysis to give a secondary cellulose ester. As noted previously, depending on the particular method employed, the distribution of the acyl substituents can be random or non-random. Secondary cellulose esters can also be prepared directly with no hydrolysis by using a limiting amount of acylating reagent. This process is particularly useful when the reaction is conducted in a solvent that will dissolve cellulose. All of these methods yield cellulose esters that are useful for preparing oxidized cellulose esters.

In one embodiment, the secondary cellulose esters useful in the present invention have a weight average molecular weight (Mw) from about 5,000 to about 400,000 as measured by GPC. In a further embodiment, the Mw is from about 10,000 to about 300,000. In yet a further embodiment, the Mw is from about 25,000 to about 250,000. In one embodiment, the DS of the cellulose esters useful herein is from about 0.5 to about 2.8. In a further embodiment, the DS is from about 1.7 to about 2.7.

The most common commercial secondary cellulose esters are prepared by initial acid catalyzed heterogeneous acylation of cellulose to form the cellulose triester. After a homogeneous solution in the corresponding carboxylic acid of the cellulose triester is obtained, the cellulose triester is then subjected to hydrolysis until the desired degree of substitution is obtained. After isolation, a randomly secondary cellulose ester is obtained. That is, the relative degree of substitution (RDS) at each hydroxyl is roughly equal.

As illustrated in FIG. 1, the degree by which a cellulose ester can be oxidized is determined by the amount of C6 hydroxyl that is available for oxidation. In this sense, a randomly substituted cellulose ester limits the level of oxidation that can be achieved. Hence, it would be advantageous to have a method that would provide cellulose esters with a high content of C6 hydroxyl.

In this context, we have surprisingly found that regioselective substituted cellulose esters can be easily and rapidly prepared by first treating the cellulose with formic anhydride or the mixed formic anhydride prepared in situ from formic acid and acyl anhydride. A second anhydride or mixture of anhydrides is added and the reaction is continued until a triester with the desired molecular weight is formed. Surprisingly, the formate ester is stable and can be isolated and characterized at this stage. Typically, we find at this stage that the triester is principally composed of two monomers: the 6-O-formate-2,3-O-acyl substituted monomer and the 2,3,6-O-acyl substituted monomer. More preferably, the cellulose formate ester is not isolated but is treated with water or an alcohol in such a manner to selectively remove the formate substitutent without affecting the other acyl substitutents. After isolation, a regioselective substituted cellulose ester is obtained with a higher level of C6 hydroxyl relative to the known methods. Typically, we find at this stage that the cellulose ester is principally composed of two monomers: the 2,3-O-acyl substituted monomer and the 2,3,6-O-acyl substituted monomer. It is preferred that the ratio of 2,3-O-acyl substituted monomer to the 2,3,6-O-acyl substituted monomer be at least 0.67, i.e., at least about 40% of the 2,3-O-acyl substituted monomer.

The cellulose that can be used in the regioselective reaction can come from a number of sources. Examples of useful cellulose include cellulose from wood pulp, bacterial cellulose, or cellulose from annual plants such as cotton or corn. In the present invention, it is not necessary to treat the cellulose with water or another agent to activate, i.e. disrupt the hydrogen bonding of the cellulose, prior to esterification. However, in select cases, those skilled in the art will recognize it may be preferential to activate the cellulose prior to esterification.

The formic acid that can be used to make the formic anhydride or the mixed formic anhydride is commercially available and typically contains 1-15% $H_2O$. Formic acid and formic anhydride are inherently not stable and the $H_2O$ serves to stabilize the formic acid. In the present invention, after cooling the formic acid solution to the first contact temperature of about −10 to about 15° C., an equal molar or slight excess amount of acyl anhydride, based on moles of water, is added to the aqueous formic acid. The preferred acyl anhydride contains 2-12 carbon atoms. The preferred acyl anhydrides are acetic anhydride, propionic anhydride, butyric anhydride, isobutyric anhydride, or a mixture thereof. The preferred temperature is from about −5 to about 10° C.

The in situ formed anhydride is adjusted to the desired second contact temperature of about 10 to about 70° C. In another embodiment, the second contact temperature is from about 15 to about 25° C. After reaching the second contact temperature, cellulose is added to the anhydride solution. Alternatively, the anhydride solution can be added to cellulose. After contacting the cellulose with the anhydride solution, the catalyst is added. The catalyst is any acid capable of promoting esterification of cellulose. Examples of such catalysts include, but are not limited to, $H_2SO_4$, HBr, HCl, $HClO_4$, or mixtures thereof. In another embodiment, the catalyst is $H_2SO_4$. The amount of catalyst that is added is from about 0.25 to about 15 wt % based on weight of cellulose. In another embodiment, the amount of catalyst is from about 2.5 to about 7.5 wt %.

Following addition of the catalyst, the slurry of cellulose is maintained at the second contact temperature for the contact time. In one embodiment, the contact time is from about 10 to about 60 min. In another embodiment, the contact time is from about 20 to about 40 min.

When the contact time with the in situ formed anhydride solution is complete, a second $C_2$-$C_{12}$ anhydride or mixture of $C_2$-$C_{12}$ anhydrides is added. In one embodiment, the anhydrides or mixtures thereof are $C_2$-$C_4$ anhydrides. In another embodiment, the anhydrides are acetic, propionic, butyric, isobutyric anhydride or mixtures thereof.

After completing the addition of the second anhydride or mixture of anhydrides, the cellulose containing solution is adjusted to the third contact temperature. In one embodiment, the third contact temperature is from about 30 to about 95° C. In another embodiment, the third contact temperature is from about 40 to about 60° C. The cellulose containing solution is maintained at the third contact temperature until a cellulose triester with the desired molecular weight is obtained. In another embodiment, the second contact time is from about 0.1 to about 24 h. In another embodiment, the second contact time is from about 2 to about 8 h. In one embodiment, the weight-average molecular weight is from about 5,000 to about 600,000 g/mol. In another embodiment, the molecular weight is from about 25,000 to about 250,000 g/mol. In yet a further embodiment, the molecular weight is from about 50,000 to about 150,000 g/mol.

When the cellulose triester with the desired molecular weight is obtained, the catalyst can be neutralized with an appropriate base and isolated by addition of a nonsolvent. Examples of suitable bases include, but are not limited to, NaOH, KOH, $MgCO_3$, $Mg(OAc)_2$, $CaCO_3$, $Ca(OAc)_2$, $Na_2CO_3$, $K_2CO_3$, $NaHCO_3$, or mixtures thereof. Examples of nonsolvents include, but are not limited to, $H_2O$, MeOH, EtOH, n-PrOH, i-PrOH, i-BuOH, or mixtures thereof. Filtration and drying by methods known to those skilled in the art provides a cellulose triester.

In the newly formed triester, the formate substituent is preferably attached to the C6 hydroxyl of cellulose. In one embodiment, the total formate DS is from about 0.7 to about 1.3. In a further embodiment, the total formate DS is from about 0.9 to about 1.1. In another embodiment, the formate RDS at C6 is at least 0.4. In yet another embodiment, the formate RDS is at least 0.6.

When a regiospecific substituted cellulose ester with a high C6 hydroxyl content is desired, the formate ester can be selectively removed by contacting the fully substituted cellulose formate ester with $H_2O$ or an alcohol at a preferred contact temperature and time. In one embodiment, the alcohol is methanol. It is preferred, but not necessary, to neutralize the catalyst prior to hydrolysis or alcoholysis. In one embodiment, the amount of $H_2O$ or alcohol is from about 5 to about 35 wt %. In another embodiment, the amount of $H_2O$ or alcohol is from about 10 to about 25 wt %. In one embodiment, the contact temperature is from about 25 to about 95° C. In another embodiment, the contact temperature is from about 40 to about 60° C. In another embodiment, the contact time is from about 4 to about 36 h. In yet a further embodiment, the contact time is from about 8 to about 24 h. For certain applications, it may be desirable to maintain a low level of formate ester in the secondary cellulose ester. The level of formate ester in the secondary ester can be controlled by selection of the appropriate contact time and temperature. The secondary regiospecific substituted cellulose ester can be isolated in the same manner as the cellulose triester. In general, the RDS of the secondary ester will reflect that established at the triester stage.

The polysaccharide esters that can be oxidized in the present invention are those that are soluble in a mixture of carboxylic acid and $H_2O$ and which have primary hydroxyls available for oxidation. Examples of such polysaccharide esters include starch esters and other polysaccharides esters having α-1,4 glycosidic linkages, pullulan esters and other polysaccharides esters having α-1,3 glycosidic linkages, cellulose esters and other polysaccharides esters having β-1,4 glycosidic linkages, and other β-glucan esters such as those from chitin, chitosan, fructans, glactomannans, glucomannas, xyloglucans, arabinoxylans and the like. The most preferred polysaccharide esters are $C_2$-$C_{10}$ cellulose esters having primary hydroxyls available for oxidation. Thus, in a further aspect of the invention, there is provided a method for converting a primary alcohol to a formyl, carboxylate, or mixture thereof, comprising: adding a 4-substituted piperidine nitroxyl derivative wherein the substitutent is capable of hydrogen bonding, a primary oxidant and a terminal oxidant to a mixture to form a reaction mixture, wherein the mixture has a pH of less than about 4 and comprises a compound comprising a primary alcohol functional group; passing of a reaction period sufficient to effect conversion of the primary alcohol functional group, wherein the primary alcohol group is found on the above listing of polysaccharide esters. In another embodiment of this aspect of the invention, the primary oxidant is a Mn (III) salt.

In one embodiment, the reaction media for oxidation is a mixture of carboxylic acid and $H_2O$. In another embodiment, the carboxylic acids are $C_2$-$C_{10}$ aliphatic carboxylic acids or mixtures thereof. In yet another embodiment, the carboxylic acids are those, which correspond to the acyl groups attached to the polysaccharide ester. For example, the carboxylic acid in the oxidation of cellulose propionate may be propionic acid and the carboxylic acid mixture in the oxidation of cellulose acetate propionate may be a mixture of propionic acid and acetic acid. In one embodiment, the amount of water in the carboxylic acid is from about 1 to about 60 wt % based on total weight of liquids. In another embodiment, the amount of water in the carboxylic acid is from about 5 to about 30 wt %.

In one embodiment of the present invention, the catalyst or mediator for oxidation of polysaccharide esters are organic nitroxyl compounds lacking α-hydrogen atoms. In one embodiment, the organic nitroxyl compounds are those arising from the piperidine or pyrrolidine series. In a further embodiment, the organic nitroxyl compounds are those that can be derived from 4-oxo-2,2,6,6-tetramethylpiperidine. For the preparation of cationic $C_2$-$C_{10}$ oxidized cellulose esters, the most preferred organic nitroxyl compound is 2,2,6,6-tetramethylpiperidine-N-oxyl (TEMPO). The preference for TEMPO in preparing cationic $C_2$-$C_{10}$ oxidized cellulose esters arises from the fact that, when used in combination with appropriate primary oxidants, the oxidation provides a high aldehyde to carboxylate ratio. A high concentration of aldehyde functionality is necessary for subsequent conversion to the cationic functionality (vide infra). For the preparation of anionic or zwitterionic $C_2$-$C_{10}$ oxidized cellulose esters, in one embodiment, the organic nitroxyl compounds are 4-hydroxy-2,2,6,6-tetramethylpiperidine-N-oxyl and derivatives thereof as well as 4-amino-2,2,6,6-tetramethylpiperidine-N-oxyl and derivatives thereof. In another embodiment, the most preferred organic nitroxyl compound for the preparation of anionic or zwitterionic $C_2$-$C_{10}$ oxidized cellulose esters is 4-acetamido-2,2,6,6-tetramethylpiperidine-N-oxyl (NHAcTEMPO). In one embodiment, the amount of organic nitroxyl compound is from about 0.0001 to about 0.1 molar equivalents per mole of polysaccharide ester monomer. In another embodiment, the amount of organic nitroxyl compound is from about 0.0025 to about 0.075 molar equivalents per mole of polysaccharide ester monomer. In yet a further embodiment, the amount organic nitroxyl compound is that amount that will give the desired degree of oxidation under the selected reaction conditions. As such, a broad range of organic nitroxyl compound is contemplated.

The preferred primary oxidants are oxidizing agents capable of oxidizing hydroxyamines that arise from the reduction of organic nitroxyls. Examples of primary oxidants include, but are not limited to halide salts such as KCl, KBr, NaCl, NaBr, NaI and the like, hypohalites such as NaOCl, NaOBr and the like, metals such as Fe(III), Mn (II), Mn(III), Cu(II) and the like, and mixtures thereof. For the preparation of anionic or zwitterionic $C_2$-$C_{10}$ oxidized cellulose esters, in one embodiment, the primary oxidants include $KMnO_4$, $Mn(OAc)_3$, $Mn_2O_3$, $MnO_2$, $Mn(NO_3)_2$, $MgCl_2$, $Mg(OAc)_2$, $Cu(NO_3)_2$, KCl, KBr, NaBr, NaCl, and NaOCl. For the preparation of cationic $C_2$-$C_{10}$ oxidized cellulose esters, in one embodiment, the primary oxidants include $Mn(NO_3)_2$, $Cu(NO_3)_2$, or mixture thereof. For the preparation of cationic $C_2$-$C_{10}$ oxidized cellulose esters using TEMPO, in one embodiment, the primary oxidant is a 1/1 mixture of $Mn(NO_3)_2$ and $Cu(NO_3)_2$. In another embodiment, the amount of primary oxidant is from about 0.0001 to about 0.1 molar equivalents per mole of polysaccharide ester monomer. In yet a further embodiment, the primary oxidant is from about 0.001 to about 0.075 molar equivalents per mole of polysaccharide ester monomer. In general, the amount of primary oxidant is that amount that will give the desired degree of oxidation under the selected reaction conditions. As such, a broad range of primary oxidant is contemplated.

In one embodiment, the terminal oxidants are any oxidizing agents capable of directly oxidizing hydroxyamines that arise from the reduction of organic nitroxyls or reoxidizing primary oxidants that in turn oxidize the hydroxyamines that arise from the reduction of organic nitroxyls. Examples of terminal oxidants include, but are not limited to, oxygen, ozone, hypohalites such as NaOCl and the like, peroxides such as hydrogen peroxide and the like, peracids such as peracetic acid and the like, and mixtures thereof. In one embodiment, the terminal oxidants include oxygen, NaOCl, peracetic acid, and hydrogen peroxide in aqueous carboxylic acid. In one embodiment, the amount of terminal oxidant is from about 0.1 to about 10 molar equivalents per mole of polysaccharide ester monomer. In a further embodiment, the amount of primary oxidant is from about 2 to about 5 molar equivalents per mole of polysaccharide ester monomer. In yet a further embodiment, the amount of terminal oxidant is that amount that will give the desired degree of oxidation under the selected reaction conditions. As such, a broad range of terminal oxidant is contemplated.

For the oxidation of cellulose esters and other polysaccharide esters, a broad contact temperature, time, and pH is contemplated. The precise values will depend upon the amount of catalyst and oxidant added, the degree of oxidation needed, and other properties, such as molecular weight, that are desired. In one embodiment, the contact temperature in the oxidation is from about 25 to about 80° C. In another embodiment, the contact temperature is from about 50 to about 60° C. In another embodiment, the contact time is from about 0.1 to about 36 h. In a further embodiment, the contact time is from about 3 to about 12 h. In yet a further embodiment, the contact time is equal to or slightly greater (about 0.01 to about 1 h) than the time that is required to add the terminal oxidant. In one embodiment, the addition time of terminal oxidant is from about 0.1 to about 35 h. In another embodiment, the terminal oxidant addition time is from about 2 to about 11 h. In one embodiment, the contact pH can range from about 0.1 to about 4. The precise value will be determined by the pH of the carboxylic acid and if the acid used in the esterification or hydrolysis of the polysaccharide ester was neutralized prior to the oxidation. In another embodiment, the contact pH is less than about 2.0. Although it is possible to control pH, it should be understood that in this invention, it is preferred that the pH not be controlled to a particular value during the reaction but that the pH should be allowed to drift during the reaction.

Oxidized cellulose esters can be isolated by a number of techniques such as precipitation in a nonsolvent, by spray drying, by spinning of fibers, etc. In one embodiment, the method is by precipitation into nonsolvents such as $H_2O$, $H_2O/C_2$-$C_4$ carboxylic acid mixtures, $C_1$-$C_4$ alcohols, $C_1$-$C_4$ esters of acetate or propionate, and the like. The solvent used depends upon the degree of oxidation, the molecular weight of the oxidized polysaccharide, and the number of carbons in the acyl substitutents. For oxidized cellulose esters such as oxidized cellulose acetate, the preferred nonsolvents are $C_2$-$C_4$ alcohols such as isopropyl alcohol or n-butanol. In the case of oxidized cellulose esters such as oxidized cellulose butyrates, the preferred nonsolvent is $H_2O$ containing from about 5 wt % to about 25 wt % of a $C_1$ to $C_4$ carboxylic acid.

In the case of oxidized cellulose esters, the amount of oxidation is most conveniently measured by determining the acid number. Acid number is defined as the mg of base (KOH) required to neutralize 1 g of oxidized cellulose ester. For cellulose esters, the acid number of the oxidized cellulose ester will be set by the intended end use application and hence a very broad acid number is anticipated. In one embodiment, the acid number is greater than 10. In another embodiment, the acid number is greater than 30. In another embodiment, the acid number is greater than 30 and less than 150. In another embodiment, the acid number is greater than 30 and less than 130. In another embodiment, the acid number is greater than 30 and less than 90.

Those skilled in the art will recognize that a number of techniques can be used to determine the acyl DS of polysaccharide esters. In the case of oxidized cellulose esters, the acyl DS value will also depend upon the technique that is used to measure the DS. Proton NMR is a common and preferred technique for measuring the acyl DS of cellulose esters. This method relies on determining the amount of glucose monomer by integration of the backbone region of the cellulose ester, which is then divided by 7, which is the number of protons normally attached to the glucose monomer. However, oxidation of the glucose monomer will reduce the number of protons depending upon the extent of oxidation. Hence, if no hydrolysis of acyl substitutents occurs during the oxidation, the normal NMR method will give an acyl DS that will increase linearly with oxidation. If hydrolysis of the acyl substitutents is occurring, the increase in DS will not be linear. Thus, proton NMR can provide an indication of oxidation for a particular sample. The acyl DS that is obtained by proton NMR for the oxidized cellulose ester is referred to as the apparent acyl DS.

The apparent acyl DS of the oxidized cellulose esters is a crucial property for virtually all applications and the preferred apparent acyl DS will vary depending upon the intended application. In one embodiment of this invention, the apparent acyl DS will be at least 0.6. In a further embodiment, the apparent acyl DS is from about 1.5 to about 3.1. In a further embodiment, the apparent acyl DS is from about 1.7 to about 2.8.

The molecular weight of the oxidized cellulose esters is another important property for most applications and the preferred molecular weight will vary depending upon the intended application. In the case of molecular weight, by selection of the acyl group attached to the cellulose polymer and by control of the amount of aldehyde and hydroxyl functional groups in the final product through selection of appropriate reaction conditions, it is possible to have molecular weights in the oxidized cellulose ester that are less than or greater than that of the cellulose ester used in the oxidation. The increase in molecular weight above that of the starting molecular weight of the cellulose esters is thought to be due to small concentrations of aldehyde functional groups that lead to effective cross-linking of the oxidized cellulose ester by formation of acetal or hemiacetal linkages. In the case of the apparent molecular weight of the oxidized cellulose ester, in one embodiment the weight-average molecular weight is at least 5,000 g/mol. In another embodiment, the range for molecular weight is from about 10,000 to about 900,000 g/mol. In a further embodiment, the range is from about 20,000 to about 400,000 g/mol.

As noted, the ratio of carboxylate to aldehyde can be used to adjust the measured molecular weight of the oxidized cellulose ester. This ratio can also be used to gain entry into a number of unique oxidized cellulose ester derivatives. The ratio of carboxylate to aldehyde can be adjusted through selection of appropriate reaction conditions. The reaction parameters, which can impact this ratio, include water concentration in the reaction media, type and concentration of organic nitroxyl compound, type and concentration of primary and terminal oxidant, reaction temperature and time, and the type of cellulose ester being oxidized. Those skilled in the art will understand that there are complex interactions among these parameters and that there are many ways to obtain the same carboxylate to aldehyde ratio by varying these parameters. The disclosure of this invention is sufficient to teach one of ordinary skill in the art how to arrive at a particular carboxylate to aldehyde ratio.

For anionic $C_2$-$C_{10}$ oxidized cellulose esters, in one embodiment, the ratio of carboxylate to aldehyde will be at least 5:1. In another embodiment, the carboxylate to aldehyde range is from about 6:1 to about 100:1. In another embodiment, the range is when the carboxylate to aldehyde range is from about 10:1 to about 50:1. In some cases, it may be desirable that that there be no aldehyde.

As a precursor for cationic $C_2$-$C_{10}$ oxidized cellulose esters, in one embodiment, the ratio of carboxylate to aldehyde will be less than 1:5. In some cases, it is preferred that there be no carboxylate. In one embodiment, the carboxylate to aldehyde range is from about 1:6 to about 1:100. In another embodiment, the carboxylate to free aldehyde range is from about 1:10 to about 1:50.

In one embodiment, the cellulose ester interpolymer has a degree of polymerization of at least 10. In another embodiment, the cellulose ester interpolymer has a degree of polymerization of at least 25. In a further embodiment, the cellulose ester interpolymer has a degree of polymerization of between 25 and 50. In yet another embodiment, the cellulose ester interpolymer has a degree of polymerization of at least 250.

As a precursor for zwitterionic $C_2$-$C_{10}$ oxidized cellulose esters, it is preferred that the ratio of carboxylate to aldehyde be from about 5:1 to about 1:5. A more preferred range is when the carboxylate to aldehyde range is from about 4:1 to about 1:4. An even more preferred range is from about 2:1 to about 1:2.

In preparing cationic or zwitterionic $C_2$-$C_{10}$ oxidized cellulose esters, the aldehyde functionality is converted to cationic functionality. The conversion of the aldehyde functionality can occur during the oxidation or immediately after oxidation but before isolation of the oxidized product. Alternatively, the cationic or zwitterionic oxidized cellulose ester precursor can be isolated and converted to the cationic or zwitterionic oxidized cellulose ester in post reactions. In the case of isolation of the oxidized cellulose ester prior to conversion to the cationic or zwitterionic oxidized cellulose ester, it is preferred that the oxidized cellulose ester not be dried prior to the reductive amination step. For example, the oxidized cellulose ester may be precipitated in a non-solvent such as methanol. The oxidized cellulose is then stored methanol wet until ready for use. The methanol can be removed by dissolving the oxidized cellulose ester in the reaction reagents, e.g. acetic acid and benzyl amine, and bubbling air or $N_2$ through the solution to remove the methanol. Because fewer acetal linkages are formed relative to drying the oxidized cellulose ester, this process allows the oxidized cellulose to be more easily dissolved in the reaction solvents.

The aldehyde functionality can be converted to a cationic functionality by treating the aldehyde with a source of $NH_3$ or a primary amine in the presence of hydrogen and a hydrogenation catalyst (reductive amination). In one embodiment, the source of $NH_3$ is ammonia gas or other sources such as $NH_3Cl$. The preferred amines are primary amines having from 1 to 14 carbon atoms. Examples of amines include, but are not limited to, ethylamine, propylamine, butylamine, benzylamine, or mixture thereof. In one embodiment, the hydrogenation catalyst is Pd supported on inert substances such as carbon. Other reducing agents can also be utilized such as sodium cyanoborohydride, sodium borohydride, or amine salts of formic acid.

The amount of amine present in the cationic or zwitterionic oxidized cellulose ester can be determined by a variety of methods such as by titration methods similar to that used to determine acid number or by other methods such as proton NMR. For the purpose of this invention, the quantity of amine in the cationic or zwitterionic oxidized cellulose ester is preferably determined by proton NMR when possible. In this regard, the DS of amine is referred to as the apparent amine DS for the same reasons described above. In one embodiment of the present invention, the apparent amine DS is at least about 0.05. In another embodiment, the apparent amine DS is about 0.2 to about 0.7.

In certain instances, it may be preferred to first oxidize a polysaccharide then esterify the oxidized polysaccharide. Hence, another aspect of the present invention is oxidation of polysaccharides with available primary hydroxyls in a mixture of carboxylic acid and $H_2O$. Examples of such preferred polysaccharides include starch and other polysaccharides having $\alpha$-1,4 glycosidic linkages, pullulan and other polysaccharides having $\alpha$-1,3 glycosidic linkages, cellulose and other polysaccharides having $\beta$-1,4 glycosidic linkages, and other $\beta$-glucans such as those from chitin, chitosan, fructans, glactomannans, glucomannas, xyloglucans, arabinoxylans and the like. The most preferred polysaccharide is cellulose. The limitations noted above for polysaccharide esters are also applicable to the oxidation of polysaccharides. In one embodiment, in the present invention for oxidation of polysaccharides, it is preferred that the pH during the oxidation be less than about 4 and, in another embodiment, less than about 2. In contrast to oxidation of cellulose in a basic media, no prior treatment of the cellulose is necessary as the reaction media for oxidation of cellulose by the methods of the present invention is sufficient to disrupt the crystallinity of the native cellulose. In one embodiment, the cellulose oxidized by the methods of the present invention has an acid number of at least 10. In another embodiment, the oxidized cellulose has an acid number of at least 30. It is also preferred that the oxidized cellulose prepared by the methods of the present invention have little solubility in water. That is, due to more even accessibility of the primary hydroxyls and resulting even distribution of carboxylates, the product is characterized by having only a small or no water-soluble fractions. The methods of the present invention are compatible with the methods commonly utilized in the esterification of cellulose. That is, after filtering to remove the liquids, the oxidized cellulose can be esterified by methods well known to those skilled in the art.

The cellulose ester interpolymers of the present invention and other compositions disclosed herein may be useful in a number of different types of applications, for example, the cellulose ester interpolymers wherein the C2 and C3 positions of each of the anhydroglucose units of the cellulose ester interpolyer are in the alcohol oxidation state, and comprising anhydroglucose units

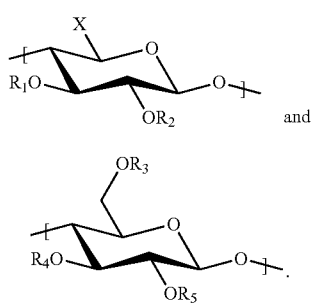

wherein $R_1$, $R_2$, $R_3$, $R_4$, and $R_5$ are independently selected from the group consisting of hydrogen and $C_2$-$C_{12}$ acyl groups, wherein at least one of $R_1$, $R_2$, $R_3$, $R_4$, and $R_5$ is a $C_2$-$C_{12}$ acyl group; and X is formyl, hydroxymethylene, aminomethyl, $R_6$—NH—$CH_2$— or carboxy or a mixture thereof, wherein $R_6$ is selected from the group consisting of alkyl, aryl, or alkylene-aryl, provided when at least some of X is carboxy, the acid number is greater than 10; wherein the anhydroglucose units A and B comprise greater than 65% of the total anhydroglucose units of the cellulose portion of the cellulose ester interpolymer. These cellulose ester interpolymers may be useful in a variety of coating compositions such as enteric coatings for medicaments, architectural coatings, maintenance coatings, industrial coatings, automotive coatings, textile coatings, inks, adhesives, and coatings for metal, paper, wood, and plastics, as binder resins. The cellulose ester interpolymers may be particularly useful in waterborne coating applications containing pigments.

Additionally, the oxidized cellulose esters of the present invention may be useful in drug delivery compositions, as an antiviral agent, as a compatibilizer in thermoplastic compositions, and in personal care compositions.

Accordingly, in one aspect, this invention relates to coating compositions comprising oxidized cellulose esters of the present invention. The oxidized cellulose esters of the invention may be incorporated into coating compositions in the same manner as known cellulose esters and are used with the conventional components and or additives of such compositions. The coating compositions may be clear or pigmented. Coating compositions containing carboxylated cellulose ether esters are known in the art and are described, for example, in U.S. Pat. No. 5,668,273, incorporated herein by reference.

In one embodiment, there provided coating compositions utilizing the cellulose ester interpolymers of the invention; in one embodiment, the cellulose ester interpolymers wherein the C2 and C3 positions of each of the anhydroglucose units of the cellulose ester interpolyer are in the alcohol oxidation state, and comprising anhydroglucose units

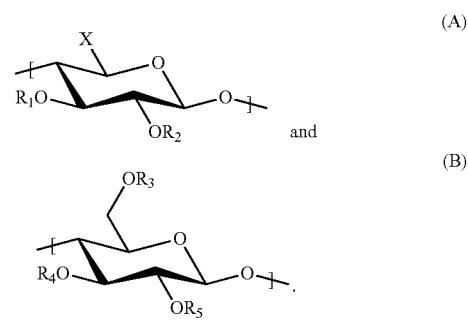

wherein $R_1$, $R_2$, $R_3$, $R_4$, and $R_5$ are independently selected from the group consisting of hydrogen and $C_2$-$C_{12}$ acyl groups, wherein at least one of $R_1$, $R_2$, $R_3$, $R_4$, and $R_5$ is a $C_2$-$C_{12}$ acyl group; and, X is formyl, aminomethyl, $R_6$—NH—$CH_2$— or carboxy or a mixture thereof, wherein $R_6$ is selected from the group consisting of alkyl, aryl, or alkylene-aryl, provided when at least some of X is carboxy, the acid number is greater than 10; wherein the anhydroglucose units A and B comprise greater than 65% of the total anhydroglucose units of the cellulose portion of the cellulose ester interpolymer.

Thus, in one embodiment, the invention provides a coating composition comprising (i) about 0.1 to about 50 weight percent, based on the total weight percent of (i) and (ii), in said composition, of cellulose ester interpolymers wherein the C2 and C3 positions of each of the anhydroglucose units of the cellulose ester interpolymer are in the alcohol oxidation state, and comprising anhydroglucose units

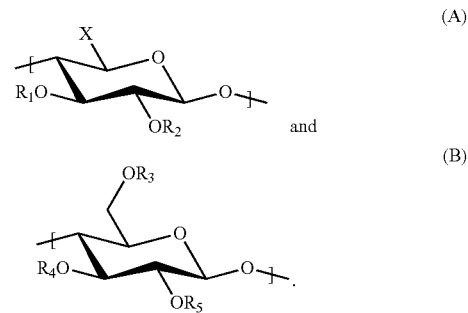

wherein $R_1$, $R_2$, $R_3$, $R_4$, and $R_5$ are independently selected from the group consisting of hydrogen and $C_2$-$C_{12}$ acyl groups, wherein at least one of $R_1$, $R_2$, $R_3$, $R_4$, and $R_5$ is a $C_2$-$C_{12}$ acyl group; and, X is formyl, aminomethyl, R$_6$—NH—CH$_2$— or carboxy or a mixture thereof, wherein R$_6$ is selected from the group consisting of alkyl, aryl, or alkylene-aryl, provided when at least some of X is carboxy, the acid number is greater than 10; wherein the anhydroglucose units A and B comprise greater than 65% of the total anhydroglucose units of the cellulose portion of the cellulose ester interpolymer; and, (ii) about 50 to 99.9 weight percent, based on the total weight of (i) and (ii) in said composition, of a resin which is other than (i); and (iii) at least one organic solvent;

wherein the total weight of (i) and (ii) is about 5 to 70 weight percent of the total weight of (i), (ii), and (iii).

In one embodiment, the cellulose esters interpolymers are anionic C$_2$-C$_8$ cellulose esters having an acid number from about 10 to about 200. In a further embodiment, the oxidized cellulose esters are anionic C$_2$-C$_4$ cellulose esters having an acid number from about 30 to about 80. In coating compositions, the concentration of oxidized cellulose esters is typically from about 0.1 to about 50 wt % based on total weight of oxidized cellulose ester and added resin. In another embodiment, the concentration of oxidized cellulose ester is from about 3 to about 30 wt %.

The cellulose ester interpolymers may be compatible with a wide range of resinous materials such as those used in coating and ink compositions. Classes of resins with which the carboxylated cellulose esters are compatible include, but are not limited to, polyesters, polyester-amides, cellulose esters, alkyds, polyurethanes, epoxy resins, polyamides, acrylics, vinyl polymers, polyisocyanates, melamines, silicone resins, and nitrocellulose. Typically, the concentration of the cellulose ester interpolymer in the coating composition is from about 0.1 to about 50 wt % based on total weight of oxidized cellulose ester and resin. In another embodiment, the concentration of cellulose ester interpolymer is from about 5 to about 30 wt %.

The cellulose ester interpolymers of the present invention are compatible with a number of solvents. These solvents include, but are not limited to methanol; ethanol; methylene chloride; diacetone alcohol; lower alkanoic acids, such as formic acid, acetic acid, and propionic acid; lower alkyl ketones, such as acetone, methyl ethyl ketone, methyl propyl ketone, methyl isobutyl ketone, and methyl n-amyl ketone; esters, such as methyl acetate, ethyl acetate, isopropyl acetate, n-propyl acetate, n-butyl acetate, 2-ethylhexyl acetate, isobutyl acetate, 2-butoxy-ethyl acetate, 1-methoxy-2-propyl acetate, 2-ethoxy-ethyl acetate, ethyl-3-ethoxypropionate, isobutyl isobutyrate, and 2,2,4-trimethyl-1,3-pentanediol-monoisobutyrate; ethers such as ethylene glycol butyl ether, propylene glycol propyl ether, 2-ethoxyethanol, 2-propoxyethanol, and 2-butoxyethanol; and mixtures thereof. The concentration of solvent in the coating compositions containing the cellulose ester is typically from about 30 to about 95 wt % based on the total weight of oxidized cellulose ester, resin, and solvent. Those skilled in the art will understand that selection of the compatible solvent will depend upon a number of factors including DS of the oxidized cellulose ester, the type of substitutent, the degree of oxidation, the molecular weight, and the like.

A coating formulation containing the cellulose esters interpolymers of the present invention may be applied to a variety of surfaces, substrates, or articles, e.g., paper; plastic; metal such as steel and aluminum; wood; gypsum board; concrete; brick; masonry; or galvanized sheeting. The type of surface, substrate, or article to be coated generally determines the type of coating formulation used. The coating formulation may be applied using means known in the art. For example, a coating formulation may be applied by spraying, brushing, rolling or any other application method to coat a substrate.

The cellulose esters interpolymers of the invention are also useful as a major film-forming component in both curing and non-curing finishes of wood coatings. Accordingly, the invention also relates to curing type wood finishes comprising from about 5 to about 20 wt % an oxidized cellulose ester of the present invention, about 15 to about 25 wt % of an alkyd resin, about 2 to about 5 percent by weight of a melamine resin, or up to about 5 to about 10 percent by weight of a urea formaldehyde resin, a relatively small amount of a silicone resin and a solvent system comprising suitable solvents such as xylene, toluene, ethanol, n-butyl alcohol, and methyl ethyl ketone. Flatting agents, such as SYLOID 83 and SYLOID 378 available from W.R. Grace, may also be employed.

The cellulose esters interpolymers of the present invention can be formulated into ink formulations. Here, the oxidized cellulose ester functions as a medium to disperse the pigments for the ink and also serve as a major film-forming resin. Thus, another embodiment of the invention relates to ink compositions comprising from about 30 to about 70% by weight of a oxidized cellulose ester, from about 30 to about 70% by weight of an ink pigment and a solvent present in an amount effective to provide a viscosity suitable for applying the ink composition under the desired conditions.

Ink compositions of the invention may also contain common ink additives depending on need of a particular ink or printing method. Such ink additives include, but are not limited to wetting agents, leveling agents, rheology additives, additives to promote resolubility/rewet on the press, coalescing aids, pigment wetting agents, dispersing agents, surfactants, waxes, defoaming agents, antifoaming agents, and modifying polymers or co-resins. The concentration of the pigment depends upon the particular pigment employed and the color and degree of hiding desired in the ink composition. Pigments, which are useful in the ink compositions of the invention, are those well known in the art and are described, for example, in Kirk-Othmer Encyclopedia of Chemical Technology, 2d Ed., Vol. 11, pp. 613-615. The solvents useful in the ink compositions of the invention are also well known in the art and are described, for example, in Kirk-Othmer Encyclopedia of Chemical Technology, 2d Ed., Vol. 11, pp. 621-623. Preferred solvents include ethanol, ethyl acetate, isopropanol, diacetone alcohol, ethylene glycol monoethyl ether, ethylene glycol monobutyl ether, and mixtures thereof.

Cellulose esters interpolymers of the present invention are particularly useful as a pigment dispersing agent. Non-oxidized cellulose esters have found utility in pigment dispersions by blending the cellulose ester and a pigment with heat and/or shear to disperse the pigment. In this manner, pigments can be dispersed in coating formulations, thereby providing high coloring power and good transparency while using a minimal amount of pigment. Such pigment dispersions can be improved by the use of the oxidized cellulose esters of the present invention in place of conventional cellulose esters. We have found that the oxidized cellulose esters of the present invention impart markedly improved wetting properties to the pigment dispersion. Mixtures of oxidized cellulose esters and pigments at weight ratios of about 20:80 to 50:50 may be prepared. These dispersions can be prepared on a two-roll mill or in a ball mill, Kady mill, sand mill, and the like.

Thus, in one embodiment, the invention provides a pigment dispersion comprising about 40 to 90 weight percent by weight of at least one pigment and correspondingly about 10 to 60 weight percent of cellulose ester interpolymers wherein the C2 and C3 positions of each of the anhydroglucose units of the cellulose ester interpolyer are in the alcohol oxidation state, and comprising anhydroglucose units

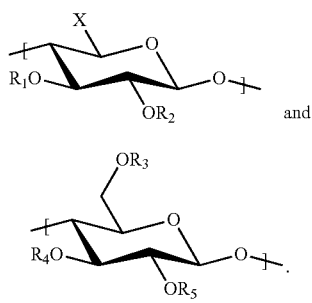

wherein $R_1$, $R_2$, $R_3$, $R_4$, and $R_5$ are independently selected from the group consisting of hydrogen and $C_2$-$C_{12}$ acyl groups, wherein at least one of $R_1$, $R_2$, $R_3$, $R_4$, and $R_5$ is a $C_2$-$C_{12}$ acyl group; and X is formyl, aminomethyl, $R_6$—NH—$CH_2$— or carboxy or a mixture thereof, wherein $R_6$ is selected from the group consisting of alkyl, aryl, or alkylene-aryl, provided when at least some of X is carboxy, the acid number greater than 10; wherein the anhydroglucose units A and B comprise greater than 65% of the total anhydroglucose units of the cellulose portion of the cellulose ester interpolymer.

The oxidized cellulose esters and pigment dispersions can be formulated into either lacquer or enamel type coatings where they are expected to be useful as rheology modifiers and/or binder components providing improved aluminum flake orientation and improved hardness. They can be applied to a substrate in the form of an organic solvent solution, an amine neutralized waterborne dispersion, a fully neutralized aqueous/organic colloidal dispersion, or as a zero VOC dispersion in aqueous ammonia. It is further expected that they will provide a water clear, high gloss, protective coating for a variety of substrates, especially metal and wood.

The cellulose ester interpolymers of the present invention can be relatively hard polymers and have high glass transition temperatures. They can be added to other resins to improve the coating hardness and to improve properties such as slip, sag resistance, mar resistance, flow, leveling, and dry time. To further improve the toughness, cross linkers such as melamines or isocyanates may be added to react with the hydroxyl containing oxidized cellulose esters or with other resins. The preferred melamine cross-linking agents include hexamethoxymethylamine, tetramethoxymethylbenzo-guanamine, tetramethoxymethylurea, mixed butoxy/methoxy substituted melamines, and the like. Typical isocyanate cross linking agents and resin include hexamethylene diisocyanate (HMDI), isophorone diisocyanate (IPDI), and toluene diisocyanate.

Because of the carboxylates present on some of the cellulose ester interpolymers of the present invention, one could use the usual cross linkers and resins used with carboxyl functional resins, e.g., epoxy resins or glycidyl-functional resins. Preferred epoxy functional resins generally have a molecular weight of about 300 to about 4000, and have approximately 0.05 to about 0.99, epoxy groups per 100 g of resin (i.e., 100-2000 weight per epoxy (WPE)). Such resins are widely known and are commercially-available under the EPON trademark of the Shell Chemical Company, the ARALDITE trademark of CIBA-Geigy, and D.E.R. resins of the Dow Chemical Company.

As noted, the cellulose ester interpolymers of the present invention are particularly useful in waterborne coating compositions. The preferred cellulose ester interpolymers are anionic $C_2$-$C_8$ cellulose esters having an acid number from about 10 to about 200. The most preferred cellulose ester interpolymers are anionic $C_2$-$C_4$ cellulose esters having an acid number from about 30 to about 80.

The cellulose ester interpolymers of this invention may be dissolved in organic solvents, partially neutralized, and dispersed in water. Examples of such organic solvents include but are not limited to 2-butanone, methyl amyl ketone, methanol, ethanol, ethyl 3-ethoxypropionate, ethylene glycol monoethyl ether, ethylene glycol monopropyl ether, and ethylene glycol monobutyl ether and the like. Dispersion of the modified cellulose ester of the present invention in water requires about 10 to about 100% neutralization of the pendant carboxylate groups with an amine. Typical amines include but are not limited to ammonia, piperidine, 4-ethylmorpholine, diethanolamine, triethanolamine, ethanolamine, tributylamine, dibutylamine, and dimethylamino ethanol.

In waterborne coating compositions, the concentration of the resin in the coating composition is from about 0.1 to about 50 wt % based on total weight of oxidized cellulose ester and resin. More preferred is when the concentration of resin is from about 5 to about 30 wt %. The concentration of cellulose ester interpolymers is typically from about 0.1 to about 50 wt % based on total weight of oxidized cellulose ester and added resin. More preferred is when the concentration of oxidized cellulose ester is from about 0.5 to about 30 wt %. The weight of resin and oxidized cellulose ester in the total composition is from about 5 to about 70 wt %. More preferred is when the weight of resin and oxidized cellulose ester in the total composition is from about 10 to about 50 wt %. The organic solvent preferably comprises from about 0 to about 20 wt % of the total composition. More preferred is when the organic solvent preferably comprises from about 5 to about 15 wt % of the total composition.

Thus, in one embodiment, the invention provides a waterborne coating composition comprising
(i) about 0.1 to about 50 weight percent, based on the total weight percent of (i) and (ii), in said composition, of cellulose ester interpolymers wherein the C2 and C3 positions of each of the anhydroglucose units of the cellulose ester interpolyer are in the alcohol oxidation state, and comprising anhydroglucose units

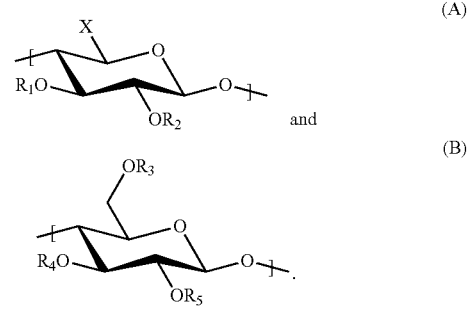

wherein $R_1$, $R_2$, $R_3$, $R_4$, and $R_5$ are independently selected from the group consisting of hydrogen and $C_2$-$C_{12}$ acyl groups, wherein at least one of $R_1$, $R_2$, $R_3$, $R_4$, and $R_5$ is a $C_2$-$C_{12}$ acyl group; and, X is formyl, hydroxymethylene, aminomethyl, $R_6$—NH—$CH_2$— or carboxy or a mixture thereof, wherein $R_6$ is selected from the group consisting of alkyl, aryl, or alkylene-aryl, provided when at least some of X is carboxy, the acid number is greater than 10; wherein the anhydroglucose units A and B comprise greater than 65% of the total anhydroglucose units of the cellulose portion of the cellulose ester interpolymer; wherein at least about 25 percent of all free carboxyl groups on said interpolymer have been neutralized with a base; and (ii) at least one compatible water-soluble or water dispersible resin;

(iii) water; and (iv) at least one organic solvent;

wherein the total weight of (i) and (ii) is between 5 and 50 weight percent of the total composition and the organic solvent comprises less than 20 weight percent of the total weight of the composition.

As a further aspect of the present invention, the above compositions are further comprised of one or more coatings additives. Such additives are generally present in a range of about 0.1 to 15 weight percent, based on the total weight of the composition. Examples of such coatings additives include leveling, rheology, and flow control agents such as silicones, fluorocarbons or cellulosics; flatting agents; pigment wetting and dispersing agents; surfactants; ultraviolet (UV) absorbers; UV light stabilizers; tinting pigments; defoaming and antifoaming agents; anti-settling, anti-sag and bodying agents; anti-skinning agents; anti-flooding and anti-floating agents; fungicides and mildewcides; corrosion inhibitors; thickening agents; or coalescing agents.

Specific examples of additional coatings additives can be found in Raw Materials Index, published by the National Paint & Coatings Association, 1500 Rhode Island Avenue, N.W., Washington, D.C. 20005.

Examples of flatting agents include synthetic silica, available from the Davison Chemical Division of W. R. Grace & Company under the trademark SYLOID; polypropylene, available from Hercules Inc., under the trademark HERCOFLAT; synthetic silicate, available from J. M Huber Corporation under the trademark ZEOLEX.

Examples of dispersing agents and surfactants include sodium bis(tridecyl) sulfosuccinnate, di(2-ethyl hexyl) sodium sulfosuccinnate, sodium dihexylsulfosuccinnate, sodium dicyclohexyl sulfosuccinate, diamyl sodium sulfosuccinate, sodium diisobutyl sulfosuccinate, disodium isodecyl sulfosuccinnate, disodium ethoxylated alcohol half ester of sulfosuccinnic acid, disodium alkyl amido polyethoxy sulfosuccinnate, tetrasodium N-(1,2-dicarboxyethyl)-N-oxtadecyl sulfosuccinnamate, disodium N-octasulfosuccinnamate, sulfated ethoxylated nonylphenol, 2-amino-2-methyl-1-propanol, and the like.

Examples of viscosity, suspension, and flow control agents include polyaminoamide phosphate, high molecular weight carboxylic acid salts of polyamine amides, and alkyl amine salt of an unsaturated fatty acid, all available from BYK Chemie U.S.A. under the trademark ANTI TERRA. Further examples include polysiloxane copolymers, polyacrylate solution, cellulose esters, hydroxyethyl cellulose, hydrophobically-modified hydroxyethyl cellulose, hydroxypropyl cellulose, polyamide wax, polyolefin wax, carboxymethyl cellulose, ammonium polyacrylate, sodium polyacrylate, and polyethylene oxide.

Several proprietary antifoaming agents are commercially available, for example, under the trademark BRUBREAK of Buckman Laboratories Inc., under the BYK trademark of BYK Chemie, U.S.A., under the FOAMASTER and NOPCO trademarks of Henkel Corp./Coating Chemicals, under the DREWPLUS trademark of the Drew Industrial Division of Ashland Chemical Company, under the TROYSOL and TROYKYD trademarks of Troy Chemical Corporation, and under the SAG trademark of Union Carbide Corporation.

Examples of fungicides, mildewcides, and biocides include 4,4-dimethyloxazolidine, 3,4,4-trimethyl-oxazolidine, modified barium metaborate, potassium N-hydroxymethyl-N-methyldithiocarbamate, 2-(thiocyano-methylthio) benzothiazole, potassium dimethyl dithiocarbamate, adamantane, N-(trichloromethylthio)phthalimide, 2,4,5,6-tetrachloroisophthalonitrile, orthophenyl phenol, 2,4,5-trichlorophenol, dehydroacetic acid, copper naphthenate, copper octonate, organic arsenic, tributyl tin oxide, zinc naphthenate, and copper 8-quinolinate.

Examples of U.V. absorbers and U.V. light stabilizers include substituted benzophenone, substituted benzotriazole, hindered amine, and hindered benzoate, available from American Cyanamide Company under the trade name Cyasorb UV, and available from Ciba Geigy under the trademark TINUVIN, and diethyl-3-acetyl-4-hydroxy-benzyl-phosphonate, 4-dodecyloxy-2-hydroxy benzophenone, and resorcinol monobenzoate.

Pigments suitable for use in the coating compositions envisioned by the present invention are the typical organic and inorganic pigments, well-known to one of ordinary skill in the art of surface coatings, especially those set forth by the Colour Index, 3d Ed., 2d Rev., 1982, published by the Society of Dyers and Colourists in association with the American Association of Textile Chemists and Colorists. Examples include, but are not limited to the following: CI Pigment White 6 (titanium dioxide); CI Pigment Red 101 (red iron oxide); CI Pigment Yellow 42, CI Pigment Blue 15, 15:1, 15:2, 15:3, 15:4 (copper phthalocyanines); CI Pigment Red 49:1; and CI Pigment Red 57:1.

This invention also relates to oral drug delivery compositions comprising the cellulose ester interpolymers of the present invention. In one aspect, the cellulose ester interpolymers are used as an enteric coating for a solid core containing the therapeutic agent. In another aspect, the cellulose ester interpolymers are used as a component in a blend used as an enteric coating. In yet another aspect, the cellulose ester interpolymers are used as release rate modifiers or solubility modifiers of therapeutic agents from a solid core. In still yet another aspect, physical mixtures of cellulose ester interpolymers and solubility modifiers are used for the controlled release of therapeutic agents from a solid core. In a further aspect, vesicles of cellulose ester interpolymers containing therapeutic agents acts as release rate and solubility modifiers in the controlled release of therapeutic agents from a solid core. In a still further aspect, the cellulose ester interpolymers are bioadhesive components in a solid core and act to increase the bioabsorption of therapeutic agents.

In drug delivery compositions, in one embodiment, the cellulose ester interpolymers are anionic, cationic, or zwitterionic $C_2$-$C_{12}$ cellulose esters. The preferred cellulose ester interpolymers will be determined by the mode selected for delivery of the therapeutic agent from the oral formulation.

In one embodiment, the invention provides an oral pharmaceutical composition comprising one or more therapeutic agents having coated thereon or admixed therewith a composition comprising one or more cellulose ester interpolymers wherein the C2 and C3 positions of each of the anhydroglucose units of the cellulose ester interpolymer are in the alcohol oxidation state, and comprising anhydroglucose units

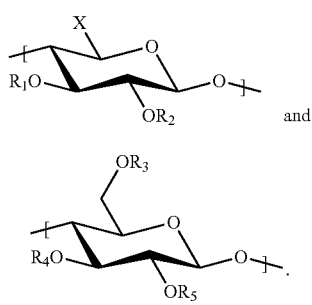

wherein
$R_1$, $R_2$, $R_3$, $R_4$, and $R_5$ are independently selected from the group consisting of hydrogen and $C_2$-$C_{12}$ acyl groups, wherein at least one of $R_1$, $R_2$, $R_3$, $R_4$, and $R_5$ is a $C_2$-$C_{12}$ acyl group; and, X is formyl, hydroxymethylene, aminomethyl, $R_6$—NH—$CH_2$— or carboxy or a mixture thereof, wherein $R_6$ is selected from the group consisting of alkyl, aryl, or alkylene-aryl, provided when at least some of X is carboxy, the acid number is greater than 10; wherein the anhydroglucose units A and B comprise greater than 65% of the total anhydroglucose units of the cellulose portion of the cellulose ester interpolymer.

In the case in which the cellulose ester interpolymers are used as enteric coatings of a solid core containing at least one therapeutic agent, in one embodiment, the cellulose ester interpolymers are anionic $C_2$-$C_4$ cellulose esters having an acid number from about 30 to about 120. In a further embodiment, the cellulose ester interpolymers are anionic $C_2$ cellulose esters having an acid number from about 40 to about 100. The enteric coating can be comprised of a single preferred oxidized cellulose ester or a mixture of cellulose ester interpolymers.

In the case of blends for enteric coating were the cellulose ester interpolymers represent one or more components of the blend, in one embodiment, the cellulose ester interpolymers are anionic $C_2$-$C_4$ cellulose esters having an acid number from about 30 to about 120. In a further embodiment, the cellulose ester interpolymers are anionic $C_2$ cellulose esters having an acid number from about 40 to about 100. The other components of the blend can be one or more of any water soluble, pH sensitive, or water insoluble polymer useful in enteric coatings. Examples of useful water soluble polymers include, but are not limited to, hydroxypropyl cellulose, hydroxypropyl methyl cellulose, or methyl cellulose. Examples of pH sensitive polymers include, but are not limited to, cellulose acetate phthalate, cellulose acetate succinate, cellulose acetate trimellitate, or hydroxypropyl methyl cellulose phthalate. Examples of useful water insoluble polymers include, but are not limited to, cellulose acetate, cellulose acetate propionate, or cellulose acetate butyrate. Those skilled in the art will recognize that the ratio of the blend components is dependent upon the individual formulation and the desired release rate of the therapeutic agent. Hence, a very broad range of blend components and component ratios is contemplated.

In enteric coatings, the cellulose ester interpolymers or blends thereof and optional additives, are dissolved in a suitable solvent or mixture of solvents. The solid core containing the therapeutic agent can be coated with these cellulose ester interpolymers solutions by a number of processes well known to those skilled in the art such as fluidized bed or side vented pan coating processes. Examples of preferred solvents in the present invention include alcohols, ketones, ethers, esters, and chlorinated hydrocarbons. Specific examples of these solvents include, but are not limited to, ethanol, acetone, 2-butanone, 2-pentanone, ethyl acetate, propyl acetate, propyl ether, tetrahydrofuran, methylene chloride, chlorobenze, and the like. Optionally, these solvents may contain from about 0.01 to about 50 wt % $H_2O$. The optional additives include plasticizers, pigments, colorants, stabilizers, antioxidants, and waxes. Commonly used plasticizers include, but are not limited to, diethyl phthalate, dioctyl phthalate, triacetin, polyethylene glycol, and the like.

In one embodiment, the invention provides a method for treating a mammal in need thereof, with at least one therapeutic agent, which comprises administering to said mammal an oral pharmaceutical composition comprising a therapeutic agent having coated thereon or admixed therewith a composition comprising a cellulose ester interpolymer wherein the C2 and C3 positions of each of the anhydroglucose units of the cellulose ester interpolyer are in the alcohol oxidation state, and comprising anhydroglucose units

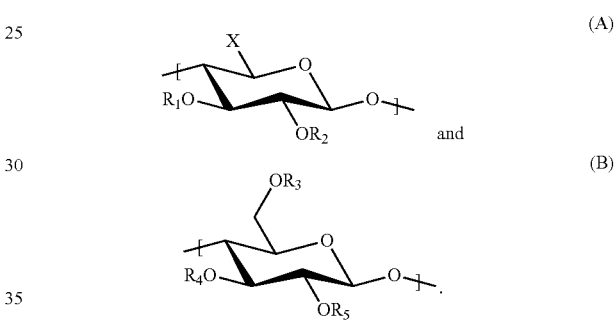

wherein
$R_1$, $R_2$, $R_3$, $R_4$, and $R_5$ are independently selected from the group consisting of hydrogen and $C_2$-$C_{12}$ acyl groups, wherein at least one of $R_1$, $R_2$, $R_3$, $R_4$, and $R_5$ is a $C_2$-$C_{12}$ acyl group; and, X is formyl, hydroxymethylene, aminomethyl, $R_6$—NH—$CH_2$— or carboxy or a mixture thereof, wherein $R_6$ is selected from the group consisting of alkyl, aryl, or alkylene-aryl, provided when at least some of X is carboxy, the acid number is greater than 10; wherein the anhydroglucose units A and B comprise greater than 65% of the total anhydroglucose units of the cellulose portion of the cellulose ester interpolymer.

In the case in which the cellulose ester interpolymers are used as release rate modifiers of therapeutic agents from a solid core, the preferred cellulose ester interpolymers are anionic, cationic, or zwitterionic $C_2$-$C_8$ cellulose esters. The most preferred cellulose ester interpolymers are anionic $C_2$-$C_4$ cellulose esters having an acid number from about 40 to about 120. As a release rate modifier, the modifier may be a single preferred oxidized cellulose ester or a mixture of cellulose ester interpolymers.

The cellulose ester interpolymers can be incorporated into the solid core along with the therapeutic agent by a number of techniques well known to those skilled in the art. The solid core comprises one or more oxidized cellulose ester, a pharmaceutically acceptable carrier, and a therapeutically effective amount of therapeutic agent. A film coating optionally surrounds the solid core. These solid cores can be in the form of, by way of example and without limitation, chewable bar, capsule, fiber, film, gel, granule, chewing gum, pellet, powder, tablet, stick, strip and wafer.

Intended routes of administration include oral or buccal. The solid core formulations of the present invention are generally administered with pharmaceutically acceptable carriers or diluents, the proportion and nature of which are determined by the solubility and chemical properties of the therapeutic agents selected, the chosen dosage form, and standard pharmaceutical practice. Solid oral forms may contain conventional excipients, for instance: lactose, sucrose, magnesium stearate, resins and like materials, flavoring, coloring, buffering, preserving, or stabilizing, agents.

As used herein, "release rate modifier" means cellulose ester interpolymers which serve to modify the rate of release of therapeutic agents. The release rate modifier will assist in providing a controlled release of the therapeutic agent and can cooperate with other components in the formulation to provide a delayed, sustained, timed, pH dependent, targeted, or further controlled delivery of the therapeutic agent. Thus, in a further embodiment, the invention provides a method wherein the cellulose ester interpolymer modifies ordinary release rate profile of the therapeutic agent. In this context, the point of the gastrointestinal tract where a given therapeutic agent is absorbed will be modified.

In this context, we expect that inclusion of certain solubility enhancers in the solid core along with the cellulose ester interpolymers may serve to provide for the increased solubility and oral bioavaliability of the therapeutic agents. The solubility enhancer can be any agent which will aid in increasing the water solubility of the therapeutic agent. The solubility enhancer can be incorporated with the oxidized cellulose ester release modifier and therapeutic agent as a physical mixture. Alternatively, in certain instances, the solubility enhancer and therapeutic agents can be incorporated into the solid core with the oxidized cellulose ester release modifier as a complex or as vesicles. Examples of solubility enhancers include water-soluble cyclodextrins, cyclodextrin derivatives, and polyethyleneoxide-polypropyleneoxide block copolymers. Preferred cyclodextrin derivatives include hydroxybutenyl cyclodextrins (U.S. Pat. No. 6,479,467, incorporated herein by reference) and sulfohydroxybutenyl cyclodextrins (U.S. Pat. No. 6,610,671, incorporated herein by reference). Preferred polyethyleneoxide-polypropyleneoxide block copolymers are available from BASF Corporation under the trade name Pluronics.

In particular, the pharmaceutical compositions of the present inventions may include water-soluble CD or CD derivatives. The CD or CD derivative is or is derived from a CD of any ring size, including but not limited to α, β, or γ-cyclodextrins. In some embodiments, the hydroxybutenyl cyclodextrin is hydroxybutenyl-α, β, or γ-cyclodextrin. In some embodiments, the hydroxybutenyl cyclodextrin derivative is sulfonated hydroxybutenyl-α, β, or γ-cyclodextrin. In some embodiments, the hydroxybutenyl cyclodextrin is hydroxybutenyl-β-cyclodextrin and the hydroxybutenyl cyclodextrin derivative is sulfonated hydroxybutenyl-β-cyclodextrin.

In some embodiments, the hydroxybutenyl-β-cyclodextrins have a molar substitution (MS, wherein MS is the total number of substituents attached to the CD) from about 1 to about 12. In some embodiments, the hydroxybutenyl-β-cyclodextrins are hydroxybutenyl-β-cyclodextrins with a MS from about 3 to about 10. In some embodiments, the hydroxybutenyl-β-cyclodextrins are water-soluble and have a MS from about 4 to about 7. In some embodiments, the hydroxybutenyl-β-cyclodextrins are water-soluble and have a MS from about 4.5 to about 5.5. In some embodiments, the hydroxybutenyl-β-cyclodextrins are water-soluble and have a MS of about 5.

In some embodiments, the hydroxybutenyl cyclodextrin derivatives are sulfonated hydroxybutenyl-α, β, or γ-cyclodextrins. In some embodiments, the sulfonated hydroxybutenyl cyclodextrins are sulfonated hydroxybutenyl-β-cyclodextrins comprising at least one hydroxybutyl sulfonate substitutent. In some embodiments, the sulfonated hydroxybutenyl-β-cyclodextrins have a MS of hydroxybutyl sulfonate from about 0.02 to about 7. In some embodiments, the hydroxybutenyl-β-cyclodextrins have a MS of hydroxybutyl sulfonate from about 0.1 to about 2. In the case of sulfonated hydroxybutenyl-α, β, or γ-cyclodextrins, those skilled in the art will recognize that these cyclodextrin ethers contain both hydroxybutenyl substitutents and hydroxybutyl sulfonate substitutents. In this case, the total MS is provided by the sum of the hydroxybutenyl MS and the hydroxybutyl sulfonate. In some embodiments, the total MS is from about 0.02 to about 12. In some embodiments, cyclodextrin ethers containing at least one hydroxybutyl sulfonate substitutent optionally further comprise additional alkyl, sulfinate, or disulfonate substitutents.

In some cases, the cellulose ester interpolymers may serve as solubility modifiers of one or more therapeutic agents in the solid core.

In one embodiment, the cellulose ester interpolymers act as solubility modifiers of therapeutic agents, the preferred cellulose ester interpolymers are anionic, cationic, or zwitterionic $C_2$-$C_{12}$ cellulose esters. The more preferred cellulose ester interpolymers are one or more anionic $C_2$-$C_8$ cellulose esters having an acid number from about 40 to about 120. The more preferred cellulose ester interpolymers are one or more anionic $C_2$-$C_4$ cellulose esters having an acid number from about 40 to about 120. In the case where the cellulose ester interpolymers serves as a solubility modifier in the solid core, the oxidized cellulose ester and the therapeutic agent can be combined in the solid core as a physical mixture.

Alternatively, in the case where the cellulose ester interpolymers serves as solubility modifiers in the solid core, the therapeutic agents and the oxidized cellulose ester can be combined to form blends, microspheres, nanospheres, or hydrogels prior to incorporation into the solid core. The blends can be formed by first dissolving the cellulose ester interpolymers in an appropriate solvent and dissolving the therapeutic agents in the same or second solvent. A blend is then formed by mixing the two solutions followed by removal of the solvents by methods known to those skilled in the art. The microspheres, nanospheres, or hydrogels can be formed by an emulsification-interfacial cross-linking process or by complexation between oppositely charged macromolecules. In the case of complexation between oppositely charged macromolecules, the complimentary charged macromolecule to the cellulose ester interpolymers may be the complimentary charged cellulose ester interpolymer. For example, an anionic $C_2$-$C_{12}$ cellulose esters having an acid number from about 40 to about 120 may be complexed with a cationic $C_2$-$C_{12}$ cellulose esters of the present invention in the presence of a therapeutic agent forming the desired microsphere or nanosphere. In the case of a zwitterionic $C_2$-$C_{12}$ cellulose ester, the complexation leading to formation of the desired microsphere or nanosphere may result from internal ionic interactions. It is not necessary that the complimentary charged macromolecule be an oxidized cellulose ester. Examples, but not limited to, of complimentary charged macromolecules for anionic cellulose ester interpolymers are chitosans having from about 40% to about 60% N-acetyl groups and derivatives thereof. Examples, but not limited to, of complimentary charged macromolecules for cationic cellulose ester interpolymers are carboxymethyl cellulose, alginates, xanthan, hyaluronic acid, and derivatives thereof. When necessary, the microspheres, nanospheres, or hydrogels can be isolated as powders by techniques known to those skilled in the art such as spray frying or freeze drying.

As used herein, "solubility modifier" means cellulose ester interpolymers which serve to modify the solubility of therapeutic agents which are otherwise poorly water-soluble. In certain instances, the cellulose ester interpolymers may act as both a release rate modifier and as a solubility modifier of therapeutic agents. Thus, in a further embodiment, the invention provides a method for increasing the solubility of the at least one therapeutic agent, thereby increasing its oral bioavailability.

In another aspect of the invention, the cellulose ester interpolymers incorporated as a solid core component can function as a bioadhesive. A bioadhesive is defined as a material that adheres or interacts strongly with biological surfaces such as mucous membranes or skin tissue. The net effect is to localize the therapeutic agent thereby increasing its bioavailability. The preferred cellulose ester interpolymers are anionic, cationic, or zwitterionic $C_2$-$C_{12}$ cellulose esters. More preferred are anionic, cationic, or zwitterionic $C_2$-$C_8$ cellulose esters.

With regard to drug delivery compositions, therapeutic agent means any bioactive agent capable of eliciting the required or desired therapeutic response from a patient when administered orally or bucally. A patient is any living human or animal. Examples of therapeutic agents include antineoplastics, antiviral agents, antidiabetic agents, antidepressants, antifungal agents, antibacterial agents, antimigrane, antiprotozoal agents, antisense agents, androgens, estrogens, sedatives, serotonin antagonists, narcotic antagonists, narcotic agonists, proteins, peptides, steroids, tranquilizers, antipsychotics, antidepressants, antiallergics, antianginals, antiarthritics, antiasthmatics, antidiabetics, antidiarrheal drugs, anticonvulsants, antigout drugs, antihistamines, antipruritics, anticoagulants, emetics, antiemetics, antispasmondics, appetite suppressants, neuroactive substances, neurotransmitter agonists, antagonists, receptor blockers and reuptake modulators, beta-adrenergic blockers, calcium channel blockers, disulfarim and disulfarim-like drugs, muscle relaxants, analgesics, antipyretics, stimulants, anticholinesterase agents, parasympathomimetic agents, hormones, anticoagulants, antithrombotics, thrombolytics, immunoglobulins, immunosuppressants, hormone agonists/antagonists, vitamins, antimicrobial agents, antineoplastics, antacids, digestants, laxatives, cathartics, antiseptics, diuretics, disinfectants, fungicides, ectoparasiticides, antiparasitics, heavy metals, heavy metal antagonists, chelating agents, gases and vapors, alkaloids, salts, ions, autacoids, digitalis, cardiac glycosides, antiarrhythmics, antihypertensives, vasodilators, vasoconstrictors, antimuscarinics, ganglionic stimulating agents, ganglionic blocking agents, neuromuscular blocking agents, adrenergic nerve inhibitors, anti-oxidants, vitamins, cosmetics, anti-inflammatories, wound care products, antithrombogenic agents, antitumoral agents, antithrombogenic agents, antiangiogenic agents, anesthetics, antigenic agents, wound healing agents, plant extracts, growth factors, emollients, humectants, rejection/anti-rejection drugs, spermicides, conditioners, antibacterial agents, antifungal agents, antiviral agents, antibiotics, tranquilizers, cholesterol-reducing drugs, agents for treatment of Parkinson's or Alzheimer's disease, vitamins/nutritional factors, antitussives, histamine-blocking drugs, monoamine oxidase inhibitor, or pharmaceutically acceptable salts or metabolites of any of the foregoing. In some embodiments, the pharmaceutically active drugs are hydrophobic, poorly water-soluble drugs.

Non-limiting examples of therapeutic agents include orally-active forms of the following: abacavir, acarbose, acebutolol, acetazolamide, acetohexamide, acrivastine, acutretin, acyclovir, alatrofloxacin, albendazole, albuterol, alclofenac, alendronate, allopurinol, aloxiprin, alprazolam, alprenolol, alprostadil, amantadine, amiloride, aminoglutethimide, amiodarone, amitriptyline, amlodipine, amodiaquine, amoxapine, amoxapine, amphetamine, amphotericin, amprenavir, aminone, amsacrine, amyl nitrate, amylobarbital, amylobarbitone, anastrozole, arzoxifene, aspirin, astemizole, atenolol, atorvastatin, atovaquone, atropine, auranofin, azapropazone, azathioprine, azelastine, azithromycin, baclofen, barbital, barbitone, becaplermin, beclamide, beclomethasone, bendrofluazide, benethamine, benethamine penicillin, benezepril, benidipine, benorylate, bentazepam, benzhexyl, benznidazole, benzonatate, benztropine, bephenium hydroxynaphthoate, betamethasone, bexarotene, bezafibrate, bicalutamide, bifonazole, biperiden, bisacodyl, bisanthrene, bovine growth hormone, bromazepam, bromfenac, bromocriptine, bromocriptine mesylate, bromperidol, brompheniramine, brotizolam, budesonide, bumetanide, bupropion, busulphan, butenafine, butobarbital, butobarbitone, butoconazole, butoconazole nitrate, calcifediol, calciprotiene, calcitonin, calcitriol, cambendazole, camidazole, camptothecan, camptothecin, candesartan, capecitabine, capsacin, capsaicin, captopril, carbamazepine, carbimazole, carbinoxamine, carbromal, carotenes, cefazolin, cefoxitin sodium, celecoxib, cephadrine, cephalexin, cerivistatin, cetrizine, chlopheniramine, chlophenisamine, chloproguanil, chlorambucil, chlordiazepoxide, chlormethiazole, chloroquine, chlorothiazide, chlorpromazine, chlorpropamide, chlorprothiocene, chlorprothixene, chlorthalidone, cholecalciferol, cilostazol, cimetidine, cinnarizine, cinoxacin, ciprofloxacin, cisapride, citalopram, citrizine, clarithromycin, clemastine, clemastine fumarate, clemizole, clenbuterol, clinofibrate, clioquinol, clobazam, clofazimine, clofibrate, clomiphene, clomipramine, clonazepam, clopidrogel, clotiazepam, clotrimazole, cloxacillin, clozapine, codeine, conjugated estrogens, cortisone acetate, cortisone acetate, cromalyn sodium, cromoglicate, cromolyn, cyclizine, cyclosporin, cyproheptadine, dacarbazine, danazol, dantrolene, darodipine, decoquinate, delavirdine, demeclocycline, desoxymethasone, dexamphetamine, dexanabinol, dexchlopheniramine, dexfenfluramine, dextropropyoxyphene, diamorphine, diazepam, diazoxide, dichlorophen, diclofenac, dicloxacillin, dicoumarol, dicumarol, didanosine, diethylpropion, diflunisal, digitoxin, digoxin, dihydro epiandrosterone, dihydrocodeine, dihydroergotamine, dihydroergotamine mesylate, dihydrotachysterol, diiodohydroxyquinoline, dilitazem, diloxanidefuroate, dimenhydrinate, dinitolmide, diphenhydramine, diphenooxylate, diphenylimidazole, diphenylpyrallin, dipyridamole, dirithromycin, disopyramide, divalproen, docetaxel, doconazole, docusate, dolasetron, domperidone, donepezil, doxercalciferol, doxazosin, doxycycline, doxorubicin, droloxifene, dronabinol, droperidol, dutasteride, econazole, econazole nitrate, editronate, efavirenz, elanapril, ellipticine, enalapril, enkephalin, enoxacin, enoximone, enrofloxacin, epalrestate, eperisone, ephedrine, eposartan, eposartan losartan, ergocalciferol, ergotamine, erythromycin, erythropoietin, essential fatty acids, estramustine, ethacrynic acid, ethambutol, ethinamate, ethinyloestradiol, ethionamide, ethopropazine, ethotoin, etodolac, etoperidone, etoposide, etretinate, exemestane, fadrozole, famcyclovir, famotidine, felbamate, felodipine, fenbendazole, fenbufen, fenfluramine, fenofibrate, fenolclopam, fenoldopam, fenoprofen, fenoprofen calcium, fentanyl, fenticonazole, fexofenadine, finasteride, flecamide, fluconazole, flucortolone, flucytosine, fludrocortisone, flunanisone, flunarizine, flunisolide, flunitrazepam, fluopromazine, fluoxetine, fluoxymisterone, flupenthixol decanoate, flupentixol, flupentixol decanoate, fluphenazine, fluphenazine decanoate, flurazepam, flurbiprofen, flurithromycin, fluticasone, fluvastatin, formestane, foscarnet, fosinopril, fosphenyloin, frovatriptan, frusemide, fumagillin, furazolidone, furosemide, furzolidone, gabapentin, gancyclovir, gemfibrozil, gentamycin, glibenclamide, gliclazide, glipizide, glucagon, glybenclamide, glyburide, glyceryl trinitrate, glymepiride, glymepride, granisetron, granulocyte stimulating factor, grepafloxacin, griseofulvin, goserelin, guanabenz, halofantrine, haloperidol, hydrocortisone, hyoscyamine, ibufenac, ibuprofen, imipenem, idarubicin, indinavir, indivir, indomethacin, insulin, interferon, pegylated interferon, interleukin-3, irbesartan, irinotecan, isoconazole, isosorbide dinitrate, isosorbide mononitrate, isotretinoin, isoxazole, isradipine, itraconazole, ivermectin, ketoconazole, ketoprofen, ketorolac, ketotifen, labetalol, lamivudine, lamotrigine, lanatoside C, lanosprazole, leflunomide, letrozole, levofloxacin, levothyroxine, lisinopril, linezolide, lombazole, lomefloxacin, lomustine, loperamide, lopinavir, loratadine, lorazepam, lorefloxacin, lormetazepam, losartan, lotrimin, lovastatin, L-thryroxine, lysuride, lysuride maleate, maprotiline, mazindol, mebendazole, meclofenamic acid, meclozine, medazepam, medigoxin, medroxyprogesterone acetate, mefenamic acid, mefloquine, megesterol acetate, melonicam, meloxicam, melphalan, mepacrine, mepenzolate bromide, meprobamate, meptazinol, mercaptopurine, mesalazine, mesoridazine, mesoridiazine, mestranol, metformin, methadone, methaqualone, methoin, methotrexate, methoxsalen, methsuximide, methylphenidate, methylphenobarbital, methylphenobarbitone, methylprednisolone, methyltestosterone, methysergide, methysergide maleate, metoclopramide, metolazone, metoprolol, metronidazole, mianserin, miconazole, midazolam, miglitol, minoxidil, mitomycin, mitotane, mitoxantrone, mofetil, molindone, montelukast, morphine, mortriptyline, moxifloxacin, mycophenolate, nabumetone, nadolol, nalbuphine, nalidixic acid, naproxen, naratriptan, natamycin, nedocromil sodium, nefazodone, nelfinavir, nerteporfin, neutontin, nevirapine, nicardipine, nicotine, nicoumalone, nifedipine, nilutamide, nimesulide, nimodipine, nimorazole, nisoldipine, nitrazepam, nitrofurantoin, nitrofurazone, nizatidine, non-essential fatty acids, norethisterone, norfloxacin, norgestrel, nortriptyline HCl, nystatin, oestradiol, ofloxacin, olanzapine, omeprazole, ondansetron, oprelvekin, ornidazole, orconazole, ospemifene, oxacillin, oxamniquine, oxantel, oxantel embonate, oxaprozin, oxatomide, oxazepam, oxcarbazepine, oxfendazole, oxiconazole, oxmetidine, oxprenolol, oxybutynin, oxyphenbutazone, oxyphencylcimine, paclitaxel, pamidronate, paramethadione, parconazole, paricalcitol, paroxetine, penicillins, pentaerythritol tetranitrate, pertazocine, pentobarbital, pentobarbitone, pentoxifylline, perchloperazine, perfloxacin, pericyclovir, perphenazine, perphenazine pimozide, phenacemide, phenbenzamine, phenindione, pheniramine, phenobarbital, phenobarbitone, phenoxybenzamine, phensuximide, phentermine, phenylalanine, phenylbutazone, phenyloin, physostigmine, phytonodione, pimozide, pindolol, pioglitazone, piroxicam, pizotifen, pizotifen maleate, posaconazole, pramipexol, pramipexole, pranlukast, pravastatin, praziquantel, prazosin, prednisolone, prednisone, pregabalin, primidone, probenecid, probucol, procarbazine, prochlorperazine, progesterone, proguanil, propofol, propranolol, propylthiouracil, pseudoephedrine, pyrantel, pyrantel embonate, pyridostigmine, pyrimethamine, quetiapine, quinapril, quinidine, quinine, rabeprazole, raloxifene, ranitidine, ravuconazole, recombinant human growth hormone, refocoxib, remifentanil, repaglinide, reserpine, residronate, retinoids, ricobendazole, rifabutin, rifabutine, rifampicin, rifampin, rifapentine, rimantadine, rimexolone, risperodone, ritonavir, rizatriptan, rizatriptan benzoate, ropinirole, rosiglitazone, roxatidine, roxithromycin, salbutamol, salmon calcitonin (sCT), saquinavir, selegiline, sertindole, sertraline, sibutramine, sildenafil, simvastatin, sirolimus, sodium cefazoline, somatostatin, sparfloxacin, spiramycins, spironolactone, stanozolol, stavudine, stavueline, stiboestrol, sulconazole, sulfabenzamide, sulfacetamide, sulfadiazine, sulfadoxine, sulfafurazole, sulfarnerazine, sulfamethoxazole, sulfapyridine, sulfasalazine, sulindac, sulphabenzamide, sulphacetamide, sulphadiazine, sulphadoxine, sulphafurazole, sulphamerazine, sulphamethoxazole, sulphapyridine, sulphasalazine, sulphin-pyrazone, sulpiride, sulthiame, sumatriptan, tacrine, tacrolimus, tamoxifen, tamsulosin, targretin, tazarotene, telmisartan, temazepam, teniposide, terazosin, terbinafine HCl, terbutaline, terbutaline sulfate, terconazole, terenadine, terfenadine, testolactone, testosterone, tetracycline, tetrahydrocannabinol, tetramisole, thiabendazole, thioguanine, thioridazine, tiagabine, tibolone, ticlidopine, ticlopidine, tiludronate, timolol, tinidazole, tioconazole, tirofibran, tizanidine, tolazamide, tolbutamide, tolcapone, tolmetin, tolterodine, topiramate, topotecan, toremifene, tramadol, trazodone, tretinoin, triamcinolone, triamterene, triazolam, trifluoperazine, trimethoprim, trimipramine, troglitazone, tromethamine, tropicamide, trovafloxacin, tubulazole, tumor necrosisi factor, undecenoic acid, ursodeoxycholic acid, valacylcovir, valconazole, valproic acid, valsartan, vancomycin, vasopressin, venlafaxine HCl, verteporfin, vigabatrin, vinblastine, vincristine, vinorelbine, vitamin A, vitamin B2, vitamin D, vitamin E and vitamin K, vitamin K5, vitamin K6, vitamin K7, vitamin K-S (II), voriconazole, zafirlukast, zileuton, ziprasidone, zolmitriptan, zolpidem, and zopiclone.

In some instances, it is believed that the cellulose ester interpolymers of the present invention may function as a therapeutic agent. In particular, due to the high concentration and localization of ionic charge, it is possible that the cellulose ester interpolymers may be effective in decreasing or preventing the frequency of transmission of the human immunodeficiency virus, herpes viruses, or sexually transmitted bacterial infections through administration to a human of an anti-human immunodeficiency virus amount or an anti-herpes virus amount or an anti-bacterial amount of the oxidized cellulose ester. The anti-viral or antibacterial oxidized cellulose ester may be used either alone or in combination with a pharmaceutically acceptable carrier or diluent. Unlike the dextran sulfates or cellulose acetate phthalates currently utilized for this purpose (J. Experimental Med. 2000, 192, 1491-1500; WO 01/05377 A1, BMC Infectious Diseases, 2002, 2:6; BMC Infectious Diseases, 2001, 1:17; Antimicrobial Agents and Chemotherapy, 2000, 44, 3199-3202; U.S. Pat. No. 6,165,493; Antimicrobial Agents and Chemotherapy, 1990, 34, 1991-1995), the ionic charge of the cellulose ester interpolymers of the present invention is covalently attached to the backbone of the polysaccharide via a carbon-carbon bond and is not susceptible to hydrolysis which will render the polysaccharide derivative inactive. This asset may allow the cellulose ester interpolymers to be more conveniently formulated into a stable formulation with a long shelf and use life. The preferred cellulose ester interpolymers are anionic, cationic, or zwitterionic $C_2$-$C_{12}$ cellulose esters. More preferred cellulose ester interpolymers are anionic $C_2$-$C_8$ cellulose esters having an acid number from about 30 to about 200. The most preferred anionic cellulose esters have an acid number from about 60 to about 150.

This invention also relates to thermoplastic compatibilizers comprising the cellulose ester interpolymers of the present invention. When incorporated into blends of two or more polymers in which one of the polymers is a cellulose ester, it is anticipated that the oxidized cellulose ester thermoplastic compatibilizer will improve the miscibility between the two polymers by providing a favorable enthalpic effect via ionic interactions. Likewise, the oxidized cellulose ester thermoplastic compatibilizers are anticipated to improve the interfacial adhesion in cellulose ester natural fiber composites by providing a favorable enthalpic effect via ionic interactions. Furthermore, in certain instances, it is anticipated that the oxidized cellulose ester thermoplastic compatibilizers will increase the biodegradation rate of the blend or composite.

As thermoplastic compatibilizers, the preferred cellulose ester interpolymers are anionic, cationic, or zwitterionic $C_2$-$C_{12}$ cellulose esters. More preferred cellulose ester interpolymers are anionic $C_2$-$C_4$ cellulose esters having an acid number from about 40 to about 120. The most preferred anionic cellulose esters have an acid number from about 40 to about 90 and the substitutent type matches the neutral cellulose ester component in the polymer blend or composite.

The anionic cellulose esters can be used in either the acid form or when the anionic functionality has been neutralized salt. In one embodiment, the anionic cellulose ester is neutralized with a base selected from NaOH, KOH, $Ca(OH)_2$, $CaCO_3$, $Ca(OAc)_2$, $Mg(OH)_2$, $MgCO_3$, or $Mg(OAc)_2$. In another embodiment, the anionic cellulose ester has been neutralized and is incorporated into the blend or composite as the Ca or Mg salt.

It is anticipated that the cellulose ester interpolymers of the invention can improve the compatibility in blends and the interfacial adhesion in composites. In one embodiment, the amount of the oxidized cellulose ester is from about 1 to about 15 wt % based on total weight of the mixture. In another embodiment, the amount of oxidized cellulose ester is from about 2 to about 5 wt % based on total weight of the mixture.

The neutral cellulose esters that can be used with the oxidized cellulose ester thermoplastic compatibilizer are secondary cellulose esters such as cellulose acetate, cellulose acetate propionate, and cellulose acetate butyrate. These cellulose esters are commercially available from Eastman Chemical Company, Inc., Kingsport, Tenn., U.S.A.

In one embodiment, the neutral cellulose esters useful in the present invention have a Mw from about 5,000 to about 400,000 as measured by GPC. In another embodiment, the Mw is from about 100,000 to about 300,000. In a further embodiment, the Mw is from about 125,000 to about 250,000. In one embodiment, the DS of the neutral cellulose esters useful herein is from about 0.7 to about 3.0. in another embodiment, the DS is from about 1.7 to about 2.8. In a further embodiment, the DS is from about 1.9 to about 2.6. The preferred Mw and DS depend upon the application in which the cellulose esters are used. In certain cases, the DS of each acyl substituent will influence the properties of cellulose mixed ester. Examples of esters of cellulose include cellulose triacetate (CTA), cellulose acetate (CA), cellulose acetate propionate (CAP), cellulose acetate butyrate (CAB), and the like.

The second polymer component in the polymer blends containing the oxidized cellulose ester thermoplastic compatibilizer is selected from polyesters, polycarbonates, cellulose esters, polyalkanoates, polyamides, polyesteramides.

The oxidized cellulose ester thermoplastic compatibilizer and the neutral cellulose esters can be in the form of a powder, bead, pellet, or fiber prior to incorporation into natural fiber composites. Most preferred is when the oxidized cellulose ester thermoplastic compatibilizer and the neutral cellulose esters are in the form of a fiber.

Often, the oxidized cellulose ester thermoplastic compatibilizer and the neutral cellulose esters are plasticized either in the fiber form prior to incorporation into the composite or during formation of the composite. Examples of preferred plasticizers include phthalates (e.g. diethyl or dibutyl phthalate), glycerol, triacetin, citrate esters (eg. triethylcitrate), aliphatic diesters (e.g. dioctyl adipate), phosphates (e.g. triphenyl phosphate), low molecular weight polyethylene glycols, esters of polyethylene glycols, and carbohydrate or polyol esters (See U.S. Ser. No. 10/340,012, filed Jan. 10, 2003 and Published U.S. Application No. 2003/0171458, incorporated herein by reference). The most preferred plasticizers are carbohydrate or polyol esters. Selection of the proper plasticizer and the amount of plasticizer is based upon the compatibility of the plasticizer with the cellulose ester and on the desired properties in the finished part. In this regard, it is important to note that the compatibility of each plasticizer will vary with each cellulose ester. For example, dioctyl adipate has poor compatibility with cellulose acetates, but good compatibility with most cellulose acetate butyrates.

It is preferred that the natural fibers of the composite structure comprise hemp, sisal, flax, kenaf, cotton, abaca, jute, kapok, papyrus, ramie, coconut (coir), wheat straw, rice straw, hardwood pulp, softwood pulp, and wood flour. More preferably, the natural cellulose fiber is selected from the group consisting of hemp, sisal, flax, kenaf, cotton, jute and coir. A suitable fiber length for the natural cellulose fiber component of this invention would be 0.01 to 10.2 cm.

It is preferred that the composite structure be comprised of about at least 50 wt % natural fiber. More preferable is when the natural fiber is from about 60 to about 75 wt % with the balance being comprised of the oxidized cellulose ester thermoplastic compatibilizer and the neutral cellulose esters.

Those skilled in the art will understand that the most preferred compositions, the preferred method of forming the composites, and the preferred processing conditions will depend on the intended applications and desired physical properties. As such, a broad composition range and processing window is anticipated.

This invention also relates to the use of the cellulose ester interpolymers of this invention as film forming agents, thickening agents, rheology modifiers, wetting agents, and dispersing agents in personal care formulations. Examples of personal care formulations include, but are not limited to, hair care, nail polish, skin gloss and makeup, lipstick and lip gloss, deodorants, mascara, and eyeliner formulations.

In personal care compositions, the preferred cellulose ester interpolymers are anionic, cationic, or zwitterionic $C_2$-$C_{12}$ cellulose esters. More preferred cellulose ester interpolymers are anionic, cationic, or zwitterionic $C_2$-$C_4$ cellulose esters. The more preferred oxidized cellulose esters are anionic $C_2$-$C_4$ cellulose esters having an acid number of about 40 to about 120. Those skilled in the art will recognize that the most preferred oxidized cellulose esters will be determined by the particular personal care formulation and the intended use.

In many personal care formulations, typically, some or all of the carboxyl groups of the preferred cellulose ester interpolymers are neutralized to provide increased solubility or clarity of the dispersion, and to provide continuous film formation. Neutralization can be accomplished by using an inorganic base such as sodium hydroxide, potassium hydroxide, ammonium hydroxide, or combinations thereof. Organic bases may also be used and include for example, monoethanolamine, diethanolamine, triethanolamine, 2-amino-2-methyl propanol (AMP), monoisopropaolamine, triisopropanolamine, and combinations thereof.

The degree of neutralization (percentage of acid groups that are neutralized with base) varies depending on the other ingredients in the personal care formulations, and the intended function and/or performance characteristics of the personal care formulations. Generally, the degree of neutralization is from about 20 to 100%. The preferred neutralization is from about 40 to 90%; and most preferred is from about 50 to 80%.

Many, if not all, personal care formulations contain other resins and additives to modify and enhance the performance of the personal care formulation. The preferred amount of each additive in highly dependent upon the particular application and hence, a very broad range is anticipated.

Examples of resins that can be included in personal care formulations involving the cellulose ester interpolymers of the present invention include, but are not limited to, cellulose nitrate, the ethyl, isopropyl, or n-butyl esters of poly(methylvinylether/maleic acid), polyvinyl pyrrolidone (PVP), polyvinyl caprolactam, polyvinyl pyrrolidone/vinyl acetate, copolymers of vinyl pyrrolidone and methyl methacrylate, copolymers of vinyl pyrrolidone and dimethylaminopropyl methacrylamide, methacrylate/methacrylic acid copolymer, poly(ethylacrylate/acrylic acid/N-tert-butyl acrylamide), PVP/ethyl methacrylate/methacrylic acid terpolymer, PVP/vinylcaprolactam/dimethylaminopropyl methacrylamide terpolymer, poly(vinyl acetate/crotonic acid), vinyl acetate/crotonates/vinyl neodecaoate copolymer, polyvinyl alcohol (PVA), copolymers of PVA and crotonic acid, copolymers of PVA and maleic anhydride, hydroxypropyl cellulose, hydroxypropyl methylcellulose, hydroxypropyl guar gum, sodium polystyrene sulfonate, octylacrylamide/acrylate/butylaminoethyl methacrylate copolymers, sulfopolyesters, and mixtures thereof.

Due to the effectiveness of the cellulose ester interpolymers of the present invention to act as a dispersing agent, the resins that can be used with preferred cellulose ester interpolymers in personal care compositions can be substantially hydrophobic. Examples of such hydrophobic resins include, but are not limited to, neutral cellulose esters such as cellulose acetate propionate or cellulose acetate butyrate, waxes; silicones; fluorocarbons; UV absorbers; photoinitiators; chlorinated and nonchlorinated polyolefins; hydroxy-functional resins such as acrylics, polyesters, and polyethers; acrylate-functional resins such as acrylated acrylics, acrylated polyesters, acrylated polyethers, acrylated polyurethanes, and acrylated epoxies; amine-modified acrylated acrylics, polyesters and polyethers; unsaturated polyesters; allyl functional polymers; aminoplast resins, and the like.

Examples of additives include, but or not limited to, plasticizers, coalescing agents, silicones, emollients, emulsifiers, lubricants, penetrants such as various lanolin compounds, protein hydrolysates, or other protein derivatives, viscosity increasing and decreasing agents, ethylene adducts and polyoxyethylene cholesterol, dyes, tints and other colorants, perfumes or fragrances, preservatives, antifoaming agents, chelating agents, polymers and resins, conditioners, and the like.

A few examples of additives that can be included in personal care formulations involving the cellulose ester interpolymers of the present invention include, but are not limited to, polysiloxane polyether copolymers, polysiloxane polydimethyl dimethylammonium acetate copolymers, acetylated lanolin alcohols, lauryl dimethylamine oxide, a lanolin-derived extract of sterol ester, lanolin alcohol concentrate, an isopropyl ester of lanolin fatty acid, sulfur rich amino acid concentrate, oleyl alcohol, stearyl alcohol, stearamidopropyl dimethyl myristyl acetate, a polyol fatty acid, a fatty amido amine, guar hydroxypropyltrimethyl ammonium chloride, cetyl/stearyl alcohol, keratin protein derivatives, isostearamidopropyl dimethylamine, stearamidopropyl dimethylamine, an amino functional silicone, ethoxylated (30) castor oil, acetylated lanolin alcohol, fatty alcohol fraction of lanolin, a mineral oil and lanolin alcohol mixture, high molecular weight ester of lanolin, N-vinylpyrrolidone/dimethylaminoethyl methacrylate copolymer, ethylene oxide adducts of soya sterol, stearic acid ester of ethoxylated methyl glucoside, sodium salt of polyhydroxycarboxylic acid, hydroxylated lanolin, cocamidopropyl dimethylamine lactate, cocamidopropyl dimethylamine propionate, cocamidopropyl morpholine lactate, isostearamidopropyl dimethylamine lactate, isostearamidopropyl morpholine lactate, oleamidopropyl dimethylamine lactate, linoleamidopropyl dimethylamine lactate, a stearamidopropyl dimethylamine lactate, ethylene glycol monostearate and propylene glycol mixture, stearamidopropyl dimethylamine lactate, acetamide monoethanolamine, lactamide monoethanolamine, stearamide monoethanolamine, behenalkonium chloride, a behenyl trimethyl ammonium methosulfate and cetearyl alcohol mixture, cetearyl alcohol, tallow imidazaolinum methosulfate, mixed ethoxylated and propoxylated long chain alcohols, stearamidopropyl dimethylamine lactate, oleamine oxide, stearamide oxide, soya ethyldiammonium ethosulfate, ricinolamidopropyl ethyldimonium ethosulfate, N-(3-isostearamidopropyl)-N,N-dimethyl amino glycolate, N-(3-isostearamidopropyl)-N,N-dimethyl amino gluconate, hydrolyzed animal keratin, ethyl hydrolyzed animal keratin, stearamidoethyl diethylamine, cocamidopropyl dimethylamine, lauramidopropyl dimethylamine, oleamidopropyl dimethylamine, palmitamidopropyl dimethylamine, stearamidopropyl dimethylamine lactate, avocado oil, sweet almond oil, grape seed oil, jojoba oil, apricot kernel oil, sesame oil, safflower oil, wheat germ oil, cocamidoamine lactate, ricinoleamido amine lactate, stearamido amine lactate, stearamido morpholine lactate, isostearamido amine lactate, isostearamido morpholine lactate, wheat germamido dimethylamine lactate, wheat germamidopropyl dimethylamine oxide, disodium isostearamido monoethanolamine sulfosuccinate, disodium oleamide PEG-2 sulfo succinate, disodium oleamide monoethanolamine sulfosuccinate, disodium ricinoleyl monoethanolamine sulfosuccinate, disodium wheat germamido monoethanolamine sulfosuccinate, disodium wheat germamido PEG-2 sulfosuccinate, stearamido amine, stearamido morpholine, isostearamido amine, isostearamido morpholine, polyethylene glycol and distearates, synthetic calcium silicate, isostearic alkanolamide, ethyl ester of hydrolyzed animal protein, blend of cetyl and stearyl alcohol with ethoxylated cetyl or stearyl alcohol, amido amines, polyamido amine, propoxylated lanolin alcohol, isostearamide diethanolamine, and hydrolyzed collagen protein.

Examples of plasticizer additives include, but or not limited to, glycols, adipic esters, citrate esters, phthalate esters, carbohydrate or polyol esters, epoxidized vegetable oils, glycerine as well as polymeric plasticizers. More preferred plasticizers in accordance with the invention are, for example, diethylhexyladipate, dibutyl phthalate, dibutyl adipate, diethyl phthalate, diisobutyl adipate, diisononyl adipate, n-butyl benzyl phthalate, 1,3-butylene glycol/adipic acid polyester, tricresyl phosphate, benzyl benzoate, triphenyl phosphate, butyl stearate, triethyl citrate, tributyl citrate, tributyl acetyl citrate, camphor, epoxidized soybean oil, propylene glycol adipate, 2,2,4-trimethyl-1,3-pentanediol diisobutyrate (TXIB), 2-amino-2-methyl propanol, and dibutyl sebacate. Other plasticizers include: Dimethicone copolyol, PEG-6 capric/caprylic glyceride, phenyl trimethicone, propylene glycol, and dipropylene glycol.

Additional examples of additives include but are not limited to emulsifiers such as ethoxylated fatty alcohols and esters, ethoxylated glycerides, dimethicone copolyol esters, glyceryl esters, hydrogenated fatty glycerides, and the sodium salts of fatty acids. Preservatives such as benzyl alcohol, methyl paraben, propyl paraben and imidazolidinylurea may also be used. Viscosity increasing agents that may be used include, methyl vinyl ether/maleic anhydride copolymer cross linked with 1,9-decadiene, carbomers, acrylates/alkyl acrylate cross polymers, the diethanolamide of a long chain fatty acid, fatty alcohols (for example, stearyl alcohol), cellulose gum, sodium chloride, and sodium sulfate. Viscosity decreasing agents that may be used include, for example, ethyl alcohol, glycerin, propylene glycol, and ethoxydiglycol. The pH of personal care formulations may be adjusted using pH adjusting agents such as citric acid, succinic acid, sodium hydroxide, and triethanolamine. Colorants for use in personal care formulations are, for example, any of the Food, Drug and Cosmetics (FD&C) or Drug and Cosmetics (D&C) dyes. Bleaching agents such as hydrogen peroxide, perborate salts, persulfate salts, and percarbonate salts may also be used. Perfume oils are also commonly found in many personal care products and may be used here. Chelating agents, such as ethylenediamine tetraacetic acid (EDTA), may also be used.

The solvents that are useful for the personal care formulations of the present invention may be water, organic solvents, or mixtures thereof. In another aspect of the invention, the preferred oxidized cellulose ester is dissolved in a compatible solvent, the resins or additives to be incorporated are added, the oxidized cellulose ester is neutralized to a given percent neutralization, and the solution inverted from a solvent continuous phase to an aqueous continuous phase. In this aspect, the cellulose ester interpolymers are also functioning as a dispersing agent in the personal care formulation. Alternatively, the preferred oxidized cellulose ester can be added directly to a solution containing water, base, and organic solvent to obtain a solution.

Examples of organic solvents include, but are not limited to, alcohols, ketones, alkyl esters, polyols, ethers, aromatic hydrocarbons, and mixtures thereof. Examples of preferred organic solvents include, but are not limited to, ethanol, propanol, isopropanol, acetone, 2-butanone, methyl acetate, ethyl acetate, ethylene glycol monobutyl ether, ethylene glycol monopropyl ether, diethylene monoethyl ether, toluene, xylene, and mixtures thereof.

As used herein, the term interpolymers include polymers comprising two or more different monomer units. Interpolymers include copolymers and terpolymers. Further, interpolymer includes graft copolymers comprising a cellulose polymer grafted to another polymer such as, but not limited to, a polyethylene glycol.

As used herein, a random distribution of carboxy groups on a cellulose polymer is defined as a cellulose polymer where the probability that an anhydroglucose unit having a C6 carboxy group is flanked on either or both by anhydroglucose units having a C6 carboxy group is unpredictable.

As used herein, a C6 carboxy group refers to the 6 position of an anhydroglucose unit being a $-CO_2H$ group wherein the $-CO_2H$ includes the free acid, salts of alkali earth metals, and ammonium and substituted ammonium salts.

As used herein, a C6 formyl group refers to the 6 position of an anhydroglucose unit being a $-C(O)H$ group.

As used herein, a stable form of a cellulose ester interpolymer is one that is stable to air hydrolysis, and capable of being isolated, characterized, and stored as a neat compound. Further, in this context, in one embodiment, the term "stable" means that it may be isolated and stored for up to six months with less than 5% hydrolysis of acyl substituents.

As used herein, an amino substituted cyclic nitroxyl derivative refers to compounds having carbocyclic rings comprising a nitroxyl group as one of the members of the ring, where no protons are alpha to the nitroxyl group, and the amino substituent is located at a position on the carbocyclic ring other than alpha to the nitroxyl group. The size of the carbocyclic ring is not particularly limited so long as the amino substituted cyclic nitroxyl derivative is operable to oxidize the C6 position of anhydroglucose units of a cellulose or cellulose ester interpolymer. In an embodiment, the carbocyclic ring contains six atoms. In another embodiment, the carbocyclic ring contains 5 atoms. The amino group may comprise an amine or a substituted amine wherein the substituent may comprise an alkyl group or a $C_2$-$C_{12}$ acyl group. In another embodiment, the amino substituted cyclic nitroxyl derivative is a 4-amino substituted 2,2,6,6-tetramethyl piperidin-1-oxyl derivative. In another embodiment, the amino substituted cyclic nitroxyl derivative is 4-amino 2,2,6,6-tetramethyl piperidin-1-oxyl. In another embodiment, the amino substituted cyclic nitroxyl derivative is a 4-($C_1$-$C_4$ acylamido)-2,2,6,6-tetramethylpiperidin-1-oxyl. In another embodiment, the amino substituted cyclic nitroxyl derivative is 4-acetamido-2,2,6,6-tetramethylpiperidin-1-oxyl.

As used herein, anhydroglucose units having C2, C3, and/or C6 positions "in the alcohol oxidation state" includes anhydroglucose units where the position in the alcohol oxidation state is not an aldehyde, ketone, or carboxy group. As a result, positions in the alcohol oxidation state include hydroxyl groups and hydroxy group derivatives such as alkyl ethers and O-acyl groups.

For the purposes of this invention, "AN" means acid number; "MEK" means methyl ethyl ketone; "PM acetate" means propylene glycol monomethyl ether acetate; "diacetone alcohol" means 4-hydroxy-4-methyl-2-pentanone; "MPK" means methyl propyl ketone; "EB" means ethylene glycol monobutyl ether; "EP" means ethylene glycol monopropyl ether; "PM" means propylene glycol monomethyl ether; "PB" means propylene glycol monobutyl ether; "EB acetate" means ethylene glycol monobutyl ether acetate; "PP" means propylene glycol monopropyl ether; "2-EH acetate" means 2-ethyl-1-hexanol acetate; "EEP" means ethyl 3-ethoxypropionate; "MIBK" means methyl iso-butyl ketone; "MAK" means methyl amyl ketone; "IBIB" means iso-butyl iso-butyrate; Texanol® means 2,2,4-trimethyl-1,3-pentanediol monoisobutyrate; "RDS" means relative degree of substitution at the 3 hydroxyls of the anhydroglucose monomer of cellulose; "Eqs" means equivalents.

As used herein, an "alkyl" group, unless noted otherwise, preferably refers to a $C_1$-$C_{12}$ straight chain hydrocarbon group.

As used herein, the term "aryl" preferably refers to groups such as phenyl, napthyl, phenanthryl, biphenyl, etc.

As used herein, the term "hydroxymethylene" refers to a group of the formula —CH$_2$OH.

As used herein, the term "alkylenearyl" preferably refers to a C$_1$-C$_{12}$ alkylene group having an aryl group attached.

EXAMPLES

Examples 1-5

To a 5 L 5-neck round-bottom jacked-flask equipped with a mechanical stirrer, reflux condenser, thermocouple, addition funnel, and a temperature controlled circulating bath was added a solution of 88% formic acid (See Table 1). The solution was chilled to 5° C. before adding 318 mL of Ac$_2$O over a 20 min period. To this solution, was added 125 g of cellulose followed by a solution of 9.35 g of H$_2$SO$_4$ in 55 mL of acetic acid. Following the addition of the H$_2$SO$_4$, the flask temperature was adjusted to 15° C. The heterogeneous mixture was stirred at this temperature for 70 min before adding an amount of Ac$_2$O slowly (See Table 1) (3.2 h addition). During the Ac$_2$O addition, the internal reaction temperature reached 37° C. Following completion of the Ac$_2$O addition, the reaction temperature was increased to 58° C. The reaction mixture became a homogeneous solution 6.8 h after adding the cellulose. The reaction temperature was maintained at 58° C. for an additional 4 h after the homogeneous solution was obtained. The reaction mixture was diluted with 500 mL of acetic acid before pouring slowly with high agitation into 5 L of H$_2$O. This gave a fine white powder, which was isolated by filtration and dried.

TABLE 1

| Example | Molar eq. of formate (amt) | Molar eq. of Ac$_2$O (amt) | DS$_F$ | DS$_{Ac}$ |
|---|---|---|---|---|
| 1 | 12 (440 gr) | 11.5 (835 mL) | 1.15 | 1.85 |
| 2 | 9 (330 gr) | 11.5 (835 mL) | 0.88 | 2.22 |
| 3 | 6 (220 gr) | 11.5 (835 mL) | 0.85 | 2.29 |
| 4 | 2 (73 gr) | 11.5 (835 mL) | 0.49 | 2.60 |
| 5 | 12 (440 gr) | 4.6 (334 mL) | | |

FIG. 1 shows the $^1$H NMR spectra for Examples 1-4. The resonances due to the C6 protons of the carbon bearing a formate or acetate substitutent are labeled as 6 F and 6A. This data illustrates that as the number of equivalents of formic acid increases, the DS of formate and the ratio of C6 formate/acetate increases. When the concentration of formic acid is held constant and the amount of Ac$_2$O is decreased (Example 5), the DS of formate and the ratio of C6 formate/acetate remains virtually unchanged. This data demonstrates that the concentration of formic acid is one of the features that control the DS of formate and selectivity at C6 for formate.

Examples 6-8

To a 1 L 3-neck round-bottom flask equipped with a mechanical stirrer, reflux condenser, and addition funnel was added 100 mL of 88% formic acid (15 molar equivalents based on cellulose). The solution was chilled to 0° C. before adding 65 mL of Ac$_2$O over a 10 min period. After warming to ambient temperature, 25 g of cellulose was added to the solution followed by a solution of 1.88 g of H$_2$SO$_4$ in 15 mL of acetic acid. The heterogeneous mixture was stirred for 30 min before the flask temperature was placed in a 30° C. water bath. To the heterogeneous mixture was added 172 mL of Ac$_2$O (9 molar equivalents based on cellulose, 20 min addition). Following completion of the Ac$_2$O addition, the reaction mixture was stirred for 10 min before the reaction temperature was increased to 50° C. The reaction mixture became a homogeneous solution 1.7 h after adding the cellulose. The reaction temperature was maintained at 50° C. and aliquots were removed at different time intervals. Each sample was treated with 0.43 g of Mg(OAc)$_2$ in 6.7 mL of acetic acid before pouring the sample into 5 wt % aqueous acetic acid. This gave a white solid, which was isolated by filtration, washed thoroughly, and dried. This reaction was repeated 2 additional times in which the reaction temperature was increased to 58° C. and to 65° C. following the Ac$_2$O addition. The results are summarized in Tables 2, 3, and 4.

TABLE 2

| Example | Reaction Temperature | Reaction Time | DS$_F$ | DS$_{Ac}$ | Mn | Mw | Mz |
|---|---|---|---|---|---|---|---|
| 6-A | 65 | 1.8 | 0.9 | 2.01 | 37,793 | 302,194 | 1,035,582 |
| 6-B | 65 | 5.8 | 0.88 | 2.06 | 13,730 | 39,798 | 98,067 |
| 6-C | 65 | 8.8 | 0.81 | 2.15 | 8,233 | 24,533 | 76,466 |
| 6-D | 65 | 23.0 | 0.52 | 2.43 | 3,965 | 6,293 | 10,121 |

TABLE 3

| Example | Reaction Temperature | Reaction Time | DS$_F$ | DS$_{Ac}$ | Mn | Mw | Mz |
|---|---|---|---|---|---|---|---|
| 7-A | 58 | 1.6 | 1.01 | 1.95 | 28,829 | 102,342 | 252,630 |
| 7-B | 58 | 5.6 | 0.95 | 1.97 | 14,404 | 38,013 | 80,493 |
| 7-C | 58 | 9.6 | 0.84 | 2.06 | 7,872 | 18,261 | 42,562 |
| 7-D | 58 | 23.6 | 0.54 | 2.42 | 3,685 | 5,943 | 10,324 |

TABLE 4

| Example | Reaction Temperature | Reaction Time | $DS_F$ | $DS_{Ac}$ | Mn | Mw | Mz |
|---|---|---|---|---|---|---|---|
| 8-A | 50 | 2.7 | 1.05 | 1.90 | 29,688 | 115,177 | 285,585 |
| 8-B | 50 | 4.7 | 1.02 | 1.93 | 27,740 | 106,452 | 268,996 |
| 8-C | 50 | 5.7 | 1.06 | 1.99 | 27,837 | 90,314 | 203,959 |
| 8-D | 50 | 8.7 | 0.97 | 2.00 | 19,772 | 89,852 | 262,219 |
| 8-E | 50 | 24.8 | 0.82 | 2.02 | 10,912 | 42,000 | 120,719 |

In these examples, cellulose acetate formates were prepared using identical conditions except for the reaction temperature. Shortly after obtaining a homogeneous reaction mixture, which is indicative of full esterification of the cellulose, the first sample was removed and isolated. In each case, cellulose acetate formates were obtained (entries 6-A, 7-A, 8-A) with weight-average molecular weights ranging from about 300,000 to about 100,000 and a formate DS from about 0.9 to about 1.05. The data in Tables 2, 3 and 4 shows the change in molecular weight, formate DS and acetate DS when the reaction is maintained at different temperatures after reaching the triester stage. At 65° C. (Table 2), the formate DS was relatively unchanged at 5.8 h but dropped with longer reaction times with a corresponding increase in acetate DS. This indicates transesterification can occur with long reaction times at this temperature. The weight-average molecular weight decreased at 65° C. from 302,000 to 6,200 over the time frame studied. At 58° C., the observations were very similar. At the 50° C. reaction temperature, the formate DS did not significantly change until after about 24 h. The weight-average molecular weight also decreased much more slowly eventually reaching 42,000 after 24.8 h reaction time.

Example 9

To a 5 L 5-neck round-bottom jacked-flask equipped with a mechanical stirrer, reflux condenser, thermocouple, addition funnel, and a temperature controlled circulating bath was added 500 mL of 88% formic acid (15 molar equivalents based on cellulose). The solution was chilled to 4° C. before adding 430 mL of $Pr_2O$ over a 20 min period. The solution was warmed to 20° C. before adding 125 g of water-activated cellulose. To the heterogeneous mixture was added a solution of 9.35 g of $H_2SO_4$ in 80.5 mL of propionic acid. Following the addition of the $H_2SO_4$, the flask temperature was adjusted to 30° C. before adding 885 mL of $Pr_2O$ slowly (9 molar equivalents based on cellulose, 30 min addition). During the $Pr_2O$ addition, the maximum internal reaction temperature reached was 37° C. The reaction mixture became a homogeneous solution 55 min after adding the cellulose. The reaction temperature was increased to 50° C. and homogeneous solution was held at this temperature for an additional 5 h before adding 2.5 g of $Mg(OAc)_2$ in 150 mL of propionic acid. After filtration through a 70-100µ glass frit funnel, the clear solution was poured slowly with high agitation into 5 L of 5 wt % aqueous acetic acid. This gave a white solid, which was isolated by filtration. After drying, 215.2 g of a fine white powder was obtained.

Characterization of this material by $^1H$ NMR and GPC revealed that the product was a cellulose propionate formate with a formate and propionate DS of 1.05 and 1.74, respectively, with a Mw of 120,295. Carbon 13 NMR indicated that majority of the formate was located at C6. A smaller amount of formate was located at C2 and none was found at C3. Correspondingly, most of the propionate was attached at C2 and C3 and only relatively small amount of propionate was located at C6.

Example 10

To a 5 L 5-neck round-bottom jacked-flask equipped with a mechanical stirrer, reflux condenser, thermocouple, addition funnel, and a temperature controlled circulating bath was added 500 mL of 88% formic acid (15 molar equivalents based on cellulose). The solution was chilled to 4° C. before adding 325 mL of $Bu_2O$ over a 20 min period. The solution was warmed to 20° C. before adding 125 g of water-activated cellulose. To the heterogeneous mixture was added a solution of 9.4 h of $H_2SO_4$ in 75 mL of butyric acid. Following the addition of the $H_2SO_4$, the flask temperature was adjusted to 30° C. and 1060 mL of $Bu_2O$ slowly added (8.4 molar equivalents based on cellulose, 25 min addition). During the $Bu_2O$ addition, the maximum internal reaction temperature reached was 49° C. The reaction mixture became a homogeneous solution 60 min after adding the cellulose. The reaction temperature was increased to 58° C. and the homogeneous solution was held at this temperature for an additional 4.3 h before adding 2.5 g of $Mg(OAc)_2$ in 150 mL of butyric acid. After filtration through a 70-100µ glass frit funnel, the clear solution was diluted with 1 L of acetic acid and poured slowly with high agitation into 5 L of $H_2O$. This gave a white solid, which was isolated by filtration. After drying, 211.6 g of a fine white powder was obtained.

Characterization of this material by $^1H$ NMR and GPC revealed that the product was a cellulose butyrate formate with a formate and butyrate DS of 1.16 and 1.75, respectively, with a Mw of 49,226. Carbon 13 NMR indicated that majority of the formate was located at C6. A smaller amount of formate was located at C2 and none was found at C3. Correspondingly, most of the butyrate was attached at C2 and C3 and only relatively small amount of butyrate was located at C6.

Example 11

To a 1 L 3-neck round-bottom flask equipped with a mechanical stirrer, reflux condenser, and addition funnel was added 100 mL of 88% formic acid (15 molar equivalents based on cellulose) followed by 65 mL of $Ac_2O$. To this solution was added 25 g of water-activated cellulose followed by a solution of 1.88 g of $H_2SO_4$ in 15 mL of butyric acid. To the heterogeneous mixture was added 334 mL of $Bu_2O$ (13.3 molar equivalents based on cellulose, 45 min addition). Following completion of the $Bu_2O$ addition, the reaction mixture was stirred for 35 min before the reaction temperature was increased to 50° C. The reaction mixture became a homogeneous solution 9 h after beginning the addition of $Bu_2O$ to the cellulose. The cellulose ester was isolated by adding the reaction solution to $H_2O$, filtering and drying.

Proton NMR showed that the product was a cellulose acetate butyrate formate with a $DS_F=0.98$, $DS_{Ac}=1.07$, and $DS_{Bu}=0.92$. The weight-average molecular weight was 46,000.

Example 12

Figure 2:
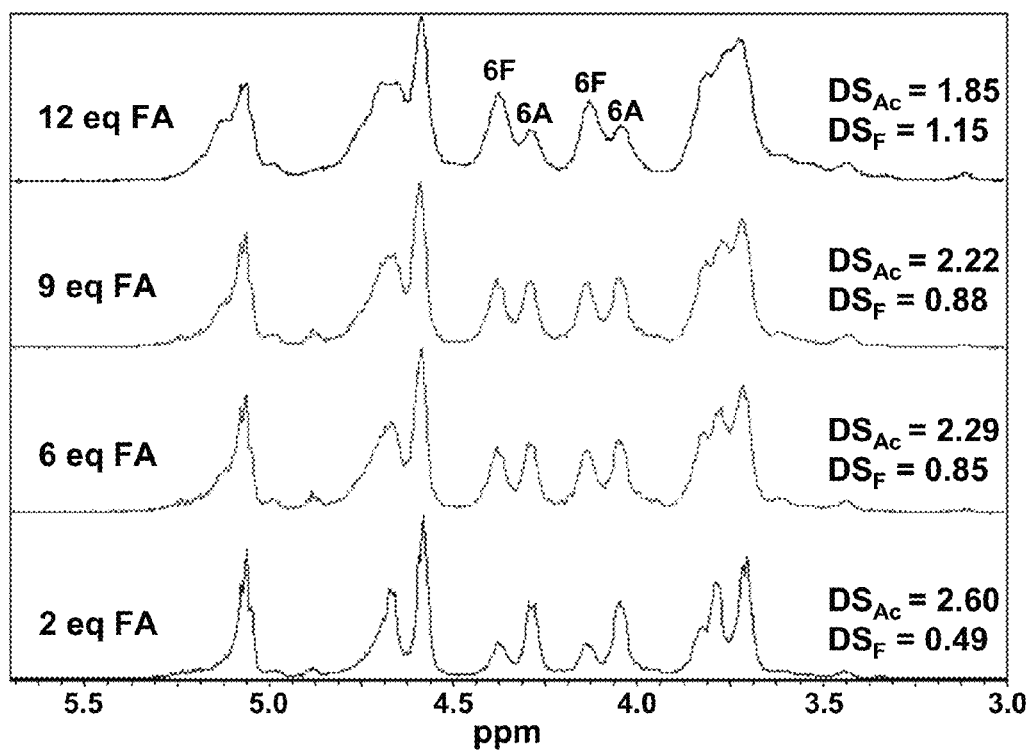
FIG. 2 is a graph showing the degree of substitution of formate per anhydroglucose unit as a function of time during a hydrolysis reaction.

Cellulose acetate formate (10 g, $DS_F=0.93$, $DS_{Ac}=2.0$) was dissolved in 120 mL of acetic acid at 60° C. To this solution was added 13.3 mL of $H_2O$, Samples were removed at different time intervals and isolated by pouring the sample into $H_2O$. The white solid was isolated by filtration, washed, and dried before submitting for analysis by $^1H$ NMR to determine the formate and acetate DS. The resulting data is summarized in FIG. 2 which shows the change in formate DS as a function of time. The initial hydrolysis of formate is rapid but the hydrolysis rate slows with time. Under these conditions, ca. 24 h is required for complete hydrolysis of formate. The $^1H$ NMR analysis also showed that the acetate DS was unchanged.

Example 13

A cellulose acetate formate having a $DS_{Ac}=1.80$ and $DS_F=0.68$ was hydrolyzed according to the general procedure of Example 12 for 24 h. Relevant physical properties for this cellulose acetate relative to a random substituted cellulose acetate produced commercially by Eastman Chemical Company as CA320S are presented in Table 5.

TABLE 5

| Sample | $DS_{Ac}$ | $RDS_6$ | $RDS_3$ | $RDS_2$ | Mn | Mw | Mz | Tg °C. | Tm °C. |
|---|---|---|---|---|---|---|---|---|---|
| Example 13 | 1.79 | 0.31 | 0.78 | 0.70 | 18,197 | 43,719 | 92,863 | 201 | 236 |
| CA320S | 1.79 | 0.58 | 0.57 | 0.64 | 21,097 | 50,450 | 96,561 | 208 | 244 |

The data in Table 5 shows both of the cellulose acetates have the same $DS_{Ac}$ and similar Mw. However, the CA prepared from the CAF has a $RDS_6$, nearly half of that for CA320S. With CA320S, the RDS at the 3 hydroxyls is very close to 1:1:1, which is typical for a random substituted CA. With the CA prepared from CAF, the $RDS_6$ is much less than that observed for the 2 and 3 positions. Comparison of the $^{13}C$ NMR carbonyl resonances for the two cellulose acetates indicates that the CA prepared from the CAF has more of the 2,3-diacetate monomer than the random substituted CA.

Example 14

Following the general procedure of Examples 6-8, a cellulose acetate formate was prepared and then, without isolation, hydrolyzed for 24 h according to the general procedure of Example 12. Relevant physical properties for this cellulose acetate relative to a non-selectively substituted cellulose acetate produced commercially by Eastman Chemical Company as CA355 are presented in Table 6.

TABLE 6

| Sample | $DS_{Ac}$ | $RDS_6$ | $RDS_3$ | $RDS_2$ | Mn | Mw | Mz |
|---|---|---|---|---|---|---|---|
| Example 14 | 2.03 | 0.38 | 0.80 | 0.86 | 22,058 | 84,152 | 229,224 |
| CA355 | 2.06 | 0.69 | 0.65 | 0.72 | 25,365 | 62,328 | 126,603 |

The data in Table 6 shows both of the cellulose acetates have nearly the same DS and similar Mw. However, the CA prepared from the CAF has a $RDS_6$ significantly less than the CA355. With CA355, the RDS at the 3 hydroxyls are close to 1:1:1. With the CA prepared from CAF, the $RDS_6$ is much less than that observed for the 2 and 3 positions which is typical for a regioselectively substituted cellulose ester prepared by the methods of the present invention. Comparison of the $^{13}C$ NMR carbonyl resonances for the two cellulose acetates indicates that the CA prepared from the CAF has more 2,3-diacetate than CA355.

Example 15

A cellulose propionate formate having a $DS_{Pr}=1.74$ and $DS_F=1.05$ was hydrolyzed according to the general procedure of Example 12 for 24 h. Proton NMR indicated that the CP had a DS of 1.67. The Mw of this CP was 93,420. The Tm taken from the first scan DSC spectra was 229° C. and the second scan Tg was 180° C. The RDS at the 6, 3, and 2 positions were 0.26, 0.69, and 0.71, respectively, indicating that the CP contained a high amount of the 2,3-dipropionate substituted monomer.

Example 16

To a 100 mL 3-neck round bottom flask was added 2 g of a regioselective substituted cellulose acetate with a $DS_{Ac}=2.03$ prepared according to the general method of Examples 6-8 and 20 mL of propionic acid. The CA was stirred at 80° C. until a homogeneous solution was obtained. After cooling to 50° C., 2.12 g of propionic anhydride was added followed by 0.05 g of $H_2SO_4$ in 0.5 mL of propionic acid. The reaction mixture was stirred for 4 h at 50° C. before pouring the solution into water. The product was isolated by filtration, washed with $H_2O$ and dried.

Proton NMR indicated that the product had a $DS_{Ac}=1.93$ and $DS_{Pr}=1.08$. The Mw for this CAP was 108,827. Carbon-13 NMR revealed that most of the propionate was located at the 6 position while the majority of the acetate was located at the 2 and 3 positions.

Example 17

To a 300 mL 3-neck round bottom flask was added 7 g (29.8 mmol) of a CA (prepared according to the general methods of Examples 6-8 and 12) and 115 mL of acetic acid. The mixture was stirred at 50° C. until a homogeneous solution was obtained. To this solution was added 20 mL of $H_2O$ followed by 317.8 mg (1.49 mmol, 0.05 eq) of NHAcTEMPO and 153.3 mg (1.49 mmol, 0.05 eq) of NaBr, respectively. To this solution was pumped 31.3 mL (148.9 mmol, 2.5 eq, 7.2 min/mL) of 32% peracetic acid. After the addition of ca. 4 mL of peracetic acid, the viscosity of the solution was observed to increase. After adding ca. 7 mL of peracetic acid, the viscosity returned to that at the start of the reaction. Aliquots were removed from the reaction at 4, 5.6, 7.3, and 8.6 h from the start of the peracetic acid addition. Each aliquot was poured into cold EtOH and the resulting solid was isolated by filtration, washed extensively with cold EtOH, and dried. Table 7 summarizes the characterization of each sample.

TABLE 7

Oxidation of cellulose acetate using 0.05 equivalents of NHAcTEMPO and NaBr.

| Examples | time (h) | Yield (%) | AN | $DS_{Ac}$ | Mn | Mw | Mz | Mw/Mn |
|---|---|---|---|---|---|---|---|---|
| Starting Material | 0 | | | 1.68 | 24,584 | 55,410 | 98,037 | 2.25 |
| 17-A | 4 | 92 | 97.5 | 2.00 | 99,927 | 426,173 | 1,000,023 | 4.26 |
| 17-B | 5.6 | 89 | 88.9 | 1.94 | 92,989 | 372,740 | 868,995 | 4.01 |
| 17-C | 7.3 | 86 | 108.0 | 2.02 | 80,785 | 343,556 | 828,377 | 4.25 |
| 17-D | 8.6 | 85 | 94.6 | 1.97 | 14,382 | 43,061 | 114,434 | 2.99 |

Example 17-A is the first aliquot taken 4 h after beginning the peracetic acid addition (15 min after completion of the peracetic acid addition). As can be seen, Example 17-A has an acid number of 97.5, the apparent DS has increased to 2.0, and the observed Mw is now 426,173. As the reaction progresses, the acid number and the DS remains relatively constant while the Mw decreases reaching 43,061 for Example 17-D. The relatively constant DS indicates that little or no hydrolysis of the acetyl substitutent is occurring under these reaction conditions.

This example demonstrates that oxidation of cellulose esters can occur rapidly under these reaction conditions without significant hydrolysis of the acyl substitutent. The increase in apparent Mw is believed to be due to crosslinking resulting from the presence of aldehydes. The subsequent decrease in Mw is believed to be due to further oxidation of the aldehydes rather than significant chain cleavage.

Examples 18-19

Cellulose acetate (prepared according to the general methods of Examples 6-8 and 12) was oxidized according to the general procedure of Example 17. Two experiments were conducted that differed only in the reaction temperature and addition rate of the peracetic acid. The reaction conditions and characterization of the products are summarized in Tables 8 and 9.

TABLE 8

Oxidation of cellulose acetate at 40° C., 40° C., 0.1 eq NHAcTEMPO, 0.1 eq NaBr, 2.5 eq PAA, 5.1 h Addition.

| Example | time (h) | AN | $DS_{Ac}$ | Mn | Mw | Mz | Mw/Mn |
|---|---|---|---|---|---|---|---|
| Starting Material | 0 | | | 1.68 | 24,584 | 55,410 | 98,037 | 2.25 |
| 18-A | 7.42 | 114.1 | 2.05 | 72,004 | 400,032 | 1,126,551 | 5.56 |
| 18-B | 9.33 | 119.0 | 2.12 | 63,013 | 338,693 | 937,631 | 5.38 |
| 18-C | 11.83 | 119.3 | 2.16 | 51,156 | 252,173 | 751,184 | 4.93 |
| 18-D | 13.92 | 114.4 | 2.21 | 38,036 | 209,500 | 644,529 | 5.51 |

TABLE 9

Oxidation of cellulose acetate at 60° C., 0.1 eq NHAcTEMPO, 0.1 eq NaBr, 2.5 eq PAA, 2.9 h Addition.

| Example | time (h) | AN | $DS_{Ac}$ | Mn | Mw | Mz | Mw/Mn |
|---|---|---|---|---|---|---|---|
| Starting Material | 0 | | | 1.74 | 23,758 | 57,266 | 106,406 | 2.41 |
| 19-A | 2.92 | 121.6 | 2.10 | 10,478 | 45,911 | 149,928 | 4.38 |
| 19-B | 4.5 | 120.4 | 2.22 | 5,706 | 21,162 | 61,365 | 3.71 |
| 19-C | 7 | 125.7 | 2.22 | 4,629 | 14,437 | 39,340 | 3.12 |
| 19-D | 9.33 | 120.8 | 2.24 | 4,804 | 15,328 | 43,992 | 3.19 |

Comparison of the results in Tables 8 and 9 shows that both sets of reaction conditions led to significant oxidation of the cellulose acetates. At 40° C., oxidation of the cellulose acetate gave acid numbers only slightly less than that obtained at 60° C. Oxidation of cellulose acetate at 40° C. gave oxidized cellulose acetates with much higher molecular weights. In all cases, the apparent DS remained above 2.0 indicating that little, if any, hydrolysis of the cellulose acetate had occurred.

The $^1$H NMR spectra for Example 18-A (7.4 h at 40° C.) and Example 19-A (2.9 h at 60° C.). The presence of a resonance at about 9.5 ppm for Example 18-A, corresponds to that of an aldehyde. This resonance is absent in the $^1$H NMR spectrum for 19-A. Aldehydes in the presence of alcohols act as cross-linking points via formation of an acetal and can lead to the observed higher molecular weights for the examples in Table 8. The absence of an aldehyde resonance in the $^1$H NMR spectrum for 19-A indicates oxidation of aldehyde to carboxy before the aldehyde can cross link.

The data in Tables 8 and 9 demonstrate that acid numbers above 110 can be achieved in the reaction temperature range of 40 to 60° C. while maintaining reaction times of less than 24 hours. This data in Tables 8 and 9 also demonstrates that oxidized cellulose acetates with apparent molecular weights ranging from 400,000 to 15,000 can be produced. Also, the data on Tables 8 and 9 demonstrates that the amount of aldehyde present in the polymer can be controlled by selection of reaction conditions.

Examples 20-23

Cellulose acetate (prepared according to the general methods of Examples 6-8 and 12) was oxidized at 50° C. according to the general procedure of Example 17.

TABLE 10

| Example | Oxidant | Eq. PAA | Rate of addition of PAA (min/mL) | Reaction Time (h) |
|---|---|---|---|---|
| 20 | TEMPO (0.1 eq) | 2.1 | 25 | 6 |
| 21 | TEMPO (0.1 eq) | 6.3 | 8 | 7 |
| 22 | TEMPO (0.1 eq) | 2.1 | 8 | 5.5 |
| 23 | NHAc TEMPO (0.1 eq.) | 2.1 | 25 | 5.5 |

Figure 3:
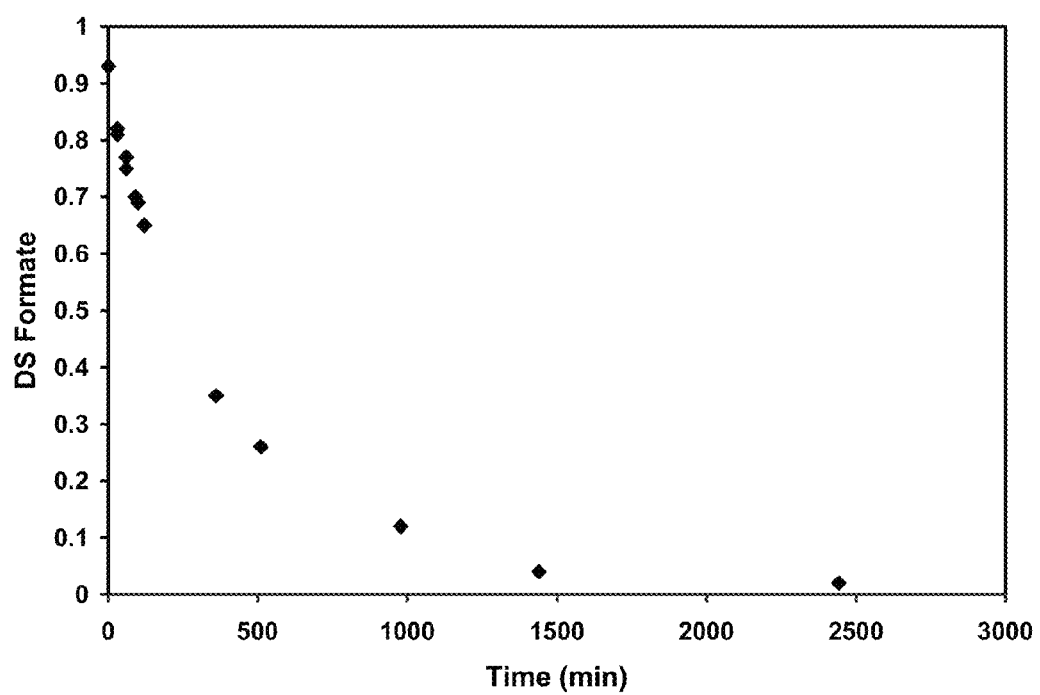
FIG. 3 is a collection of $^{13}C$ NMR spectra of C6 carbon resonances for Examples 20-23.
Figure 4:
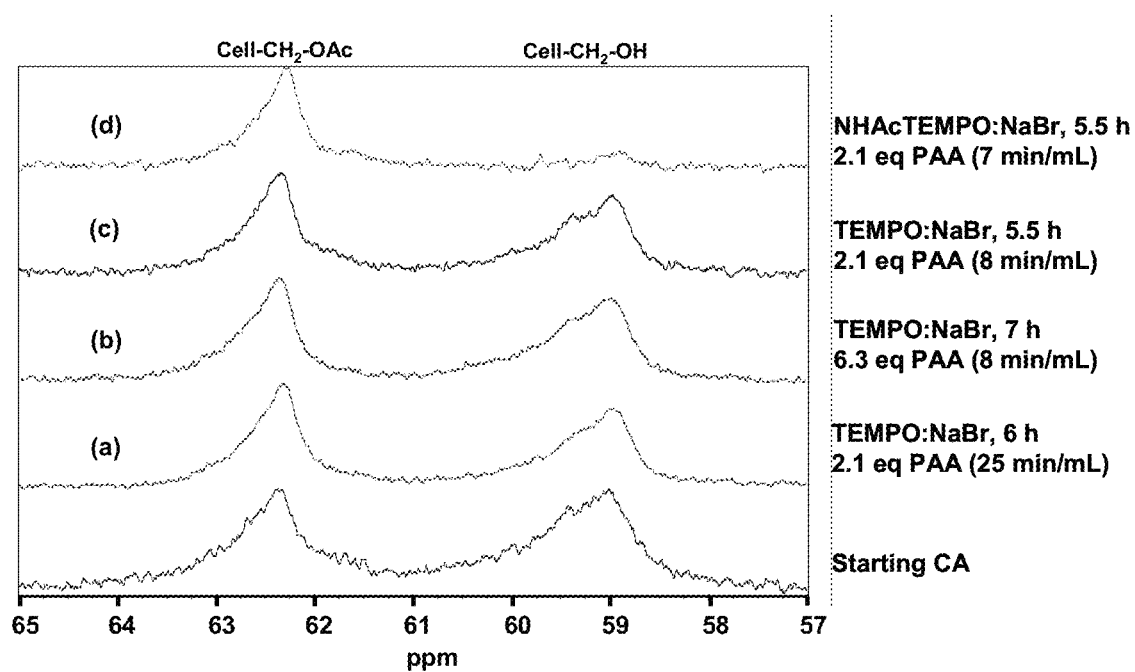
FIG. 4 is a collection of $^1H$ NMR spectra of cellulose ester interpolymers described in Examples 1-4.

FIG. 3 shows the $^{13}$C NMR C6 carbon resonances for Examples 20-23. The resonances corresponding to C6 substituted (ca. 63.5 ppm) and unsubstituted (ca. 59 ppm) carbons are indicated. From FIG. 3 it can be seen that oxidation using NHAcTEMPO (Example 23) resulted in almost a complete loss of the C6 unsubstituted carbon peak through oxidation of the C6 unsubstituted carbons. Reactions involving TEMPO (Examples 20-22) resulted in only minor amounts of oxidation of the cellulose acetate.

Examples 24-39

Cellulose acetate (DS=1.79) commercially available from Eastman Chemical Company as CA320S was oxidized according to the general procedure of Example 17 using different primary oxidants. For each entry, the reaction temperature was 50° C. and 1.0 equivalents of peracetic acid was used as the terminal oxidant. The results of these experiments are summarized in Table 11.

TABLE 11

Oxidation of cellulose acetate using different primary oxidants.

| Ex. | Primary Oxidant | Eqs NHAcTEMPO | Eqs Oxidant | time (h) | AN | $DS_{Ac}$ | Mn | Mw | Mz |
|---|---|---|---|---|---|---|---|---|---|
| 24 | NaBr | 0.075 | 0.005 | 7.0 | 86.0 | 1.92 | 82,399 | 462,685 | 1,273,700 |
| 25 | NaCl | 0.075 | 0.05 | 6.1 | 32.6 | | 44,757 | 373,245 | 1,222,505 |
| 26 | NaOCl | 0.05 | 0.05 | 5.7 | 77.6 | | 7,962 | 104,848 | 425,340 |
| 27 | $Mn(NO_3)_2$ | 0.05 | 0.05 | 6.3 | 21.9 | 1.79 | 23,676 | 55,694 | 105,607 |
| 28 | $Mn(OAc)_3$ | 0.05 | 0.05 | 6 | 39.8 | 1.85 | 21,716 | 81,622 | 180,797 |
| 29 | $KMnO_4$ | 0.05 | 0.05 | 5.8 | 69.6 | 2.11 | 10,738 | 55,814 | 160,774 |
| 30 | $KMnO_4$ | 0 | 0.05 | 5.3 | 15.8 | 1.99 | 6,593 | 100,424 | 961,709 |
| 31 | $Mn_2O_3$ | 0.05 | 0.05 | 7.5 | 38.9 | 1.79 | 6,288 | 28,130 | 85,789 |
| 32 | $MnO_2$ | 0.05 | 0.05 | 7.4 | 22.4 | 1.74 | 17,197 | 52,593 | 99,585 |
| 33 | $MgCl_2$ | 0.05 | 0.05 | 7.4 | 53.8 | 1.88 | 104,438 | 377,680 | 819,682 |
| 34 | $Mg(NO_3)_2$ | 0.05 | 0.05 | 6.0 | 29.4 | 1.87 | 27,120 | 61,559 | 115,958 |
| 35 | $FeCl_3$ | 0.075 | 0.005 | 6.3 | 42.9 | 1.83 | 56,273 | 611,843 | 2,444,184 |
| 36 | $Cu(NO_3)_2$ | 0.05 | 0.05 | 5.3 | 9.9 | 1.81 | 16,300 | 49,156 | 106,042 |
| 37 | $H_2SO_4$ | 0.05 | 0.05 | 5.75 | 3.6 | | 12,895 | 59,169 | 205,294 |
| 38 | $Na_2S_2O_5$ | 0.075 | 0.005 | 7.0 | 3.6 | 1.74 | 21,905 | 55,989 | 110,453 |
| 39 | Oxone | 0.05 | 0.05 | 5.2 | 7.9 | 1.72 | 26,699 | 72,775 | 181,597 |

Oxidation of this CA using NaBr as the primary oxidant provided an anionic CA with an acid number of 86 (Example 24). Substitution of NaBr with other metal halides such as NaCl or NaOCl (Examples 25 and 26) also led to significant oxidation of this CA. Salts or acids based on sulfur gave oxidized CA with low acid numbers (Examples 37-39). Example 37 was particularly surprising as the prior art teaches that strong acids such as $H_2SO_4$ are critical components in TEMPO based oxidations of polysaccharides. Examples 27-32 demonstrate that Mn salts are useful as primary oxidants in the oxidation of polysaccharides such as cellulose esters. That is, it is possible to have halogen free oxidations. Of particular interest is Example 28 involving $Mn(OAc)_3$ which gave an acid number of 39.8. In this case, the salt does not contain a halogen. Oxidation of acetate would lead to peracetic acid which, in the absence of a good primary oxidant, gives only low levels of oxidation. Hence, the observed increase in acid number is due to the Mn. Related to Mn as the primary oxidant, Examples 29 and 30 are of particular interest. $KMnO_4$ is a known oxidant of polysaccharides but is also known that high levels of $KMnO_4$ are required and that this leads to nonselective oxidations with significant loss in molecular weight. Example 29 demonstrates that when used with NHAcTEMPO according to the methods of the present invention, $KMnO_4$ can be used catalytically to provide a cellulose ester with high levels of oxidation and good molecular weight. In comparison, in the absence of NHAcTEMPO (Example 32), a much lower acid number and molecular weight is obtained. Examples 33-36 demonstrate that other metal salts such as Mg, Cu, and Fe can also be used as primary oxidants in the oxidation of cellulose esters.

This example demonstrates that primary oxidants other than NaBr are useful in the oxidation of cellulose esters by the methods of the present invention. Of particular note is the use of metal salts based on Mn, Mg, Fe, and Cu for halogen free oxidations. Also, this example shows that the presence of a strong acid such as $H_2SO_4$, is not necessary for the oxidation of polysaccharide esters as suggested in the prior art. In this case, the presence of the strong acid resulted in essentially no oxidation of the cellulose ester.

Examples 40-46

Cellulose acetate (prepared according to the general methods of Examples 6-8 and 12) was oxidized according to the general procedure of Example 17 using variable amounts of NaBr. In each experiment, the number of equivalents of NHAcTEMPO was 0.05 eq and the reaction temperature was 50° C. The results of these experiments are summarized in Table 12.

TABLE 12

| Entry | Temp (° C.) | Eqs PAA | Eqs NaBr | time (h) | AN | $DS_{Ac}$ | Mn | Mw | Mz |
|---|---|---|---|---|---|---|---|---|---|
| 40[a] | 70 | 1.75 | 0 | 7.4 | 1.7 | 1.73 | 12264 | 29393 | 72520 |
| 41[b] | 60 | 1.75 | 0 | 6.0 | 5.8 | 1.76 | 20518 | 53836 | 128975 |
| 42[b] | 50 | 1.75 | 0 | 5.8 | 15.5 | 1.74 | 19956 | 50610 | 113075 |
| 43[a] | 50 | 1.0 | 0.005 | 7.3 | 52.0 | 1.88 | 33154 | 240966 | 901965 |
| 44[a] | 50 | 1.0 | 0.010 | 7.3 | 68.5 | 1.91 | 24985 | 303643 | 1076774 |
| 45[a] | 50 | 1.0 | 0.025 | 6.4 | 84.3 | 1.94 | 46358 | 313329 | 1029011 |
| 46[b] | 50 | 1.75 | 0.050 | 6.0 | 99.8 | 2.05 | 52736 | 712062 | 1956569 |

For the starting CA: DS = 1.72, Mw = 34124.
For the starting CA: DS = 1.74, Mw = 57266.

The data in Table 12 illustrates a number of points. First, at a reaction temperature of about 50° C. (cf. Examples 40-42), a primary oxidant is not necessary to obtain oxidation. However, addition of even a small amount of NaBr increased the level of oxidation (cf. Examples 43 and 44) relative to when none was used. As the amount of NaBr was increased, both the acid number and the molecular weight were observed to increase. The acid number and the molecular weight of the oxidized cellulose ester can be controlled by varying the amount of NaBr while maintaining a constant temperature and concentration of NHAcTEMPO.

Examples 47-49

Cellulose acetate (prepared according to the general methods of Examples 6-8 and 12) was oxidized according to the general procedure of Example 17 using variable amounts of NHAcTEMPO. In each experiment, the number of equivalents of NaBr was 0.025 eq and the reaction temperature was 50° C. The results of these experiments are summarized in Table 13.

TABLE 13

| Examples | Eqs NHAcTEMPO | time (h) | AN | $DS_{Ac}$ | Mn | Mw | Mz |
|---|---|---|---|---|---|---|---|
| 47[a] | 0.025 | 5.8 | 39.6 | 1.84 | 28,439 | 136,195 | 491,427 |
| 48[a] | 0.050 | 6.4 | 84.3 | 1.94 | 46,358 | 313,329 | 1,029,011 |
| 49[b] | 0.075 | 5.8 | 144.9 | 2.25 | 14,034 | 498,008 | 1,652,295 |

For the starting CA: DS = 1.72, Mw = 34124.
For the starting CA: DS = 1.68, Mw = 55410.

The date in Table 13 for Examples 47-49 shows that as the number of equivalents of NHAcTEMPO are increased while maintaining a constant amount of NaBr and a constant temperature, the acid number and molecular weight of the products increases.

Examples 50-55

Cellulose acetate propionate and cellulose acetate butyrate, commercially available from Eastman Chemical Co. as CAP504 and CAB553, were oxidized at 50° C. according to the general procedure of Example 17 using 1.0 eqs PAA, 0.005 eqs of NaBr, and 0.075 eqs NHAcTEMPO. In the case of the CAP 504, propionic acid was substituted for acetic acid. In the case of the CAB 553, butyric acid was substituted for acetic acid. The oxidized cellulose esters were isolated by precipitation in 5% aqueous acetic acid. The results of these experiments are summarized in Table 14.

TABLE 14

| Examples | Substrate | Time (h) | AN | DS | Mn | Mw | Mz |
|---|---|---|---|---|---|---|---|
| | CAP | 0 | | 2.19 | 9,572 | 22,155 | 40,845 |
| 50 | CAP | 2.75 | 46.8 | 2.46 | 30,196 | 183,329 | 618,702 |
| 51 | CAP | 5.08 | 57.1 | 2.43 | 20,139 | 109,475 | 350,227 |
| 52 | CAP | 22.67 | 61.3 | 2.42 | 21,761 | 102,716 | 298,772 |
| | CAB | 0 | | 2.24 | 10,786 | 31,114 | 63,308 |
| 53 | CAB | 3.08 | 33.9 | 2.25 | 25,717 | 461,098 | 1,663,635 |
| 54 | CAB | 4.17 | 43.9 | 2.28 | 34,126 | 312,655 | 1,036,959 |
| 55 | CAB | 22.42 | 40.7 | 2.24 | 24,126 | 162,815 | 496,651 |

The data in Table 14 for the Examples demonstrates that cellulose esters, such as CAP and CAB, can be oxidized according to the methods of this invention.

Example 56

Water activated cellulose (10 g) was suspended in 400 g of a mixture of acetic acid/$H_2O$ (85/15, wt./wt.) containing NHAcTEMPO (0.99 g) and NaBr (0.032 g) at 50° C. The oxidation was started by slowly adding 25.9 mL of a 32% peracetic acid solution with stirring, in 3 hours, to the mixture. The oxidized cellulose was isolated, after 4.5 hours of reaction, by filtration, washed, and dried at 50° C. in a vacuum oven.

The oxidized cellulose was acetylated with acetic anhydride using sulfuric acid as catalyst. Specifically, oxidized cellulose (10 g) was activated with water, dewatered with acetic acid, and then suspended in a mixture of acetic acid (100 g) and acetic anhydride (28 g) at 13-15° C. The esterification was started by adding a mixture of sulfuric acid (0.75 g) and acetic acid (20 g) to the above cold cellulose, acetic acid and acetic anhydride mixture with vigorous mixing. This reaction mixture was kept at 20 to 23° C. for about 20 to 30 min follow by heating it at 50° C. until a viscous solution was obtained. Unreacted acetic anhydride was destroyed by addition of a water/acetic acid mixture. The acetylated oxidized cellulose was recovered by precipitation from water after the sulfuric acid used as catalyst was neutralized with sodium acetate. After drying, the acid number of the oxidized CA was found to be 10. No loss of product due to solubilization (vide infra) was observed suggesting an even distribution of carboxylates.

Example 57

Comparative

Cellulose (Placetate F) was first activated with 10% aqueous NaOH at 0 to 10° C. for 10 to 20 min. The NaOH solution was then removed from cellulose by filtration and washing with distilled water. The pH of this activated cellulose was then adjusted to 10.8 to 10.9 using 0.5 M NaOH. The oxidation was started by slowly adding 11.5% solution of NaOCl (85 ml) to a mixture of activated cellulose (10 g), TEMPO (0.1 g), NaBr (3.2 g) and distilled water (400 g) in a 3-necked round bottle flask with stirring. The reaction temperature was 25° C., and the pH of the reaction mixture was kept at 10.8 to 10.9 with 0.5 M NaOH. Cellulose was in solution at the end of the addition of NaOCl solution (120 min.). The oxidized cellulose was recovered by precipitation from ethanol, washed with ethanol and dry at 50° C. in a vacuum oven. After drying, the acid number for the oxidized cellulose was determined to be 133.

The above reaction was repeated with the exception that only 25.5 mL of NaOCl was utilized. At the end of the contact time, insoluble fiber was removed from the reaction mixture by filtration. The soluble cellulose fraction was isolated as above. It was found that 37 wt % of the product was the soluble portion and 63 wt % of the product was the insoluble fiber portion that was removed by filtration. The insoluble cellulose fraction was found to have an acid number of 5.6.

Collectively, this data indicates that the oxidation of cellulose under these conditions proceeds by oxidation and solubilization of the cellulose from the fiber surface. That is, the reaction is heterogeneous and the distribution of the carboxylates is not random.

Example 58

Commercial cellulose esters (CA320S, CA398-30, CAP504-0.2, CAB 553-0.4) available from Eastman Chemical Company, were oxidized according to the methods described in Examples 17 and 50. The solubility of these oxidized cellulose esters were evaluated in a variety of solvents by mixing 0.2 g of oxidized cellulose ester in 1.8 g of solvent for ca. 16 h. The samples were inspected and graded on the following scale: 1=Insoluble; 3=Partially Soluble; 5=Gels; 7=Soluble, Hazy Solution; 9=Soluble, Clear Solution. The results are summarized in Table 15. The solubility of the non-oxidized commercial cellulose esters in the same solvents are provided for each sample within the parenthesis.

TABLE 15

Solubility of oxidized cellulose esters in different solvents.

| Solvent | Oxidized CA DS = 1.94 AN = 88.7 | Oxidized CA DS = 2.67 AN = 51.8 | Oxidized CAP DS = 2.41 AN = 61.3 | Oxidized CAB DS = 2.16 AN = 40.7 |
|---|---|---|---|---|
| Formic acid | 9 (9) | 9 (9) | 9 (9) | 9 (9) |
| Acetic acid | 9 (9) | 9 (9) | 9 (9) | 9 (9) |
| Acetone | 3 (1) | 9 (9) | 9 (9) | 9 (9) |
| MEK | 5 (1) | 9 (9) | 9 (9) | 9 (9) |
| Ethyl acetate | 5 (1) | 7 (5) | 9 (9) | 9 (9) |
| PM acetate | 5 (1) | 5 (1) | 9 (9) | 9 (9) |
| diacetone alcohol | 3 (1) | 3 (9) | 9 (9) | 9 (9) |
| MPK | 3 (1) | 3 (1) | 9 (3) | 9 (9) |
| EB | 5 (1) | 3 (1) | 9 (9) | 9 (9) |
| EP | 5 (1) | 3 (1) | 9 (9) | 9 (9) |
| PM | 3 (1) | 3 (1) | 9 (9) | 9 (9) |
| PB | 5 (1) | 3 (1) | 9 (9) | 9 (9) |
| Methanol | 3 (1) | 1 (1) | 9 (9) | 9 (9) |
| Methyl acetate | 3 (3) | 9 (1) | 9 (9) | 9 (9) |
| Propionic acid | 5 (1) | 1 (3) | 9 (9) | 9 (9) |
| Isopropyl acetate | 3 (1) | 1 (1) | 3 (3) | 5 (9) |
| EB acetate | 3 (1) | 1 (1) | 7 (3) | 5 (9) |
| PP | 3 (1) | 1 (1) | 1 (1) | 5 (9) |
| n-Propyl acetate | 5 (1) | 1 (1) | 3 (3) | 5 (9) |
| Isobutyl acetate | 3 (1) | 1 (1) | 3 (1) | 5 (1) |
| Texanol | 3 (1) | 1 (1) | 3 (1) | 5 (9) |
| 2-EH acetate | 1 (1) | 1 (1) | 1 (1) | 1 (1) |
| Dichloromethane | 1 (1) | 1 (9) | 1 (7) | 7 (9) |
| EEP | 1 (1) | 1 (1) | 7 (3) | 9 (9) |
| MIBK | 1 (1) | 1 (1) | 7 (3) | 7 (9) |
| MAK | 1 (1) | 1 (1) | 3 (1) | 3 (9) |
| n-Butyl acetate | 1 (1) | 1 (1) | 3 (3) | 3 (9) |
| IBIB | 1 (1) | 1 (1) | 1 (1) | 1 (1) |

This reveals that oxidized cellulose esters are soluble in a wide variety of solvents typically utilized in many coating applications. As the data indicates, solubility is dependent upon the type of substituent, DS, and acid number.

Example 59

Two samples of a regiospecific substituted cellulose acetate (DS=1.72) prepared according to the general methods of Examples 6-8 and 12, were oxidized according to the general procedure of Example 17. For comparison, two samples of a randomly substituted cellulose acetate having virtually the same DS (1.79) were also oxidized by the method of Example 17. In each experiment, the number of equivalents of NHAcTEMPO was 0.075 eq, the number of equivalents of NaBr was 0.005, the number of equivalents of PAA was 1.0, the reaction temperature was 50° C., and the reaction times were ca. 8 h. The acid numbers for the two oxidized regioselective substituted cellulose acetates were 109 and 104. The acid numbers for the two randomly substituted cellulose acetates were 79 and 86.

This example demonstrates that at the same degree of substitution, a regioselectively substituted cellulose ester can provide an oxidized cellulose acetate with a higher acid number than that obtained from the equivalent randomly substituted cellulose acetate.

Example 60

Cellulose acetate (42.8 mmol, DS=1.79 was dissolved in 100 mL of glacial acetic acid and 20 mL of water. After warming to 50° C., 0.02 eq $Mn(NO_3)_2$, 0.02 eq $Cu(NO_3)_2$, and 0.104 eq TEMPO were added, respectively. The reaction was stirred at 50° C. open to the atmosphere. Approximately 4 h after adding the TEMPO, the viscosity of the solution increased dramatically. In order to decrease the viscosity of the reaction solution, 32 mL of 75% aqueous acetic acid was added.

After 23 h of reaction time, the reaction mixture was poured into an Omni blender and a mixture of $H_2O$ and ice was added. After mixing, the oxidized CA precipitated. The product was washed twice with water before washing with ethanol. Drying in vacuo at 60° C. for 65 h gave a white solid (84% yield). After drying, the product was quite difficult to dissolve in most solvents due to cross-linking via acetal formation between the newly formed aldehyde and unreacted hydroxyls that are present in the cellulose ester. Nevertheless, the $^1H$ NMR of the product (DMSO-$d_6$, reveals the resonances due to the desired aldehyde groups (9-10 ppm). The resonances centered near 6 ppm are believed to be due to acetals formed by reaction of unreacted hydroxyls with the aldehyde functionality.

A portion (8.6 mmol) of the oxidized cellulose acetate prepared above was dissolved in 20 mL of glacial acetic acid and 13 eq of benzyl amine. To this solution was added 0.4 g of 10% Pd/C before heating the solution to 40° C. The solution was then blanketed with a positive hydrogen atmosphere.

After 21 h, the reaction mixture was filtered to remove the Pd/C. The solution was then poured into water which was maintained at 0° C. overnight. The product was isolated by filtration, washed, and dryed in vacuo at 60° C. for 16 h (yield=44%).

A $^1H$ NMR spectrum of the product was used to calculate the apparent DS for acetate of 2.14 and the apparent DS for amine of 0.60. Quantitative carbon 13 NMR also confirmed successful introduction of benzyl amine. This is demonstrated by the presence of resonances due to aromatic carbons (cf. 122-140 ppm) and resonances due to $CH_2$ attached to NH (cf. 44-50 ppm).

Example 61

Cellulose Acetate (240 g, 1.03 mol, DS=1.79) was oxidized according to the method described in Example 60. At the conclusion of the reaction, the oxidized cellulose acetate was isolated by precipitation in cold MeOH. The product was isolated by filtration, washed with MeOH, and stored wet in MeOH. To determine the solids present and to obtain an analytical sample, a portion was removed and dried at 60° C. in vacuo. The product was found to contain 68.5 wt % MeOH.

Methanol wet oxidized cellulose acetate (6.35 g, 8.6 mmol) was dissolved in benzyl amine (25 eq) and glacial acetic acid (82 mL). The MeOH was removed by bubbling $N_2$ through the solution. After all of the MeOH was removed, 0.4 g of 10% Pd/C was added to the solution and the solution was placed under a positive $H_2$ atmosphere. The reaction was stirred at 25° C. for 16 h before venting the hydrogen. The Pd/C was removed by centrifuging and decanting the liquids. Approximately 70% of the acetic acid was removed in vacuo before cold water was added to precipitate the cellulose acetate benzyl amine. The product was isolated by filtration, washed, and dried at 60° C. in vacuo. Analysis of this material by proton NMR revealed that the apparent DS acetate was 1.73 and the apparent DS amine was 0.26. GPC indicated that the product had a weight-average molecular weight of 22,700.

Example 62

Preparation of Cellulose Acetate Butyrate Esters Having a Hydroxyl Content of 1.42 and Oxidation to an Oxidized CAB Hydrolysis of cellulose esters to produce randomly substituted cellulose esters with high hydroxyl content:
To a 12 L 5-neck jacketed round bottom flask equipped with a mechanical stirrer, a reflux condenser, a recirculation bath for temperature control, and an addition funnel was added 2410.5 g of glacial acetic acid, 2140.0 g of butyric acid, 1190.0 g of deionized water, and 1260.1 g of cellulose acetate butyrate (CAB381-20, Eastman Chemical Company) with slow stirring. Following addition of the CAB381-20, the temperature was increased to 70-71° C. and the mixture was allowed to stir until a homogenous solution was obtained. To this mixture was added 19 g of sulfuric acid in 100 g of glacial acetic acid. After addition of the sulfuric acid mixture, the reaction mixture was held at 70° C. for the entire reaction time. After 12 h reaction time, 240 g of deionized water was added. After 24 h reaction time, an additional 400 g of deionized water was slowly added. After 36 h reaction time, a final addition was added consisting of 1560.0 g of acetic acid, 72.0 g of butyric acid, and 324.0 g of deionized water, and 152.8 g of magnesium acetate tetrahydrate. For characterization purposes, a small portion of the resulting CAB was isolated by adding the reaction solution to deionized water, filtering, and washing the solid with water and drying. The remaining CAB reaction mixture was drained from the flask and stored at 10° C. until used in oxidation reactions. Proton NMR indicated that the isolated product had a $DS_{Bu}$=1.13, $DS_{Ac}$=0.44, and $DS_{OH}$=1.42 $DS_{OH}$. The weight-average molecular weight (GPC) was 104,681.

Oxidation of randomly substituted cellulose esters with high hydroxyl content: Six oxidation experiments were performed on the CAB produced above by the general procedure of example 17. Two different types of primary oxidants were utilized at three different concentrations at a fixed concentration of NHAcTEMPO (0.075 eq). The results for these experiments are shown in Table 16.

TABLE 16

Oxidation of randomly substituted cellulose esters using different primary oxidants and oxidant equivalents.

| Sample | Reaction Time (min) | NaBr (eqs) | Mn(OAc)$_3$ (eqs) | Acid Number | Weight-Average MW |
|---|---|---|---|---|---|
| 1 | 1200 | 0.075 | 0 | 98 | 6103 |
| 2 | 1200 | 0.01 | 0 | 92 | 5258 |
| 3 | 1200 | 0.05 | 0 | 90 | 7095 |
| 4 | 1212 | 0 | 0.01 | 23 | 35360 |
| 5 | 1200 | 0 | 0.05 | 11 | 36437 |
| 6 | 1176 | 0 | 0.1 | 72 | 9539 |

This example demonstrates that cellulose esters such as CAB can be hydrolyzed in acidic aqueous media to produce randomly substituted cellulose esters with high hydroxyl content. Oxidation of this CAB using different primary oxidants produced oxidized CAB with a range of acid numbers (11 to 98) and weight-average MW (ca. 5000 to 36000). Thus, by selection of appropriate reaction conditions a broad range of oxidized CAB can be produced.

Example 63

Preparation of Cellulose Acetate Butyrate Ester Having a Hydroxyl Content of 1.81 and Oxidation to an Oxidized CAB Hydrolysis of cellulose esters to produce randomly substituted cellulose esters with high hydroxyl content:

The procedure of Example 62 was used to produce a CAB381 having a high hydroxyl content. This example is different in that the reaction temperature was maintained at 71° C. and the composition of the liquids added at 36 h was 990 g of acetic acid, 48 g of butyric acid, and 560 g of deionized water, and 51 g of magnesium acetate tetrahydrate. For characterization purposes, a small portion of the resulting CAB was isolated by adding the reaction solution to deionized water, filtering, and washing the solid with water and drying. The remaining CAB reaction mixture was drained from the flask and stored at 10° C. until used in oxidation reactions. Proton NMR indicated that the isolated product had a $DS_{Bu}$=0.96, $DS_{Ac}$=0.22, and $DS_{OH}$=1.81 $DS_{OH}$. The weight-average molecular weight (GPC) was 66,097.

Oxidation of randomly substituted cellulose esters with high hydroxyl content:

The CAB produced above was oxidized by the general procedure of Example 17 using 0.075 eq of NHAcTEMPO and 0.75 eq of sodium bromide. The product obtained had an acid number of 104 (mg KOH/g) and a weight-average molecular weight of 4847.

This example demonstrates that CAB can be hydrolyzed in acidic aqueous media to produce a randomly substituted CAB with high hydroxyl content. Oxidation of this CAB using 0.75 eqs of NaBr produced an oxidized CAB with a high acid number and a low weight-average molecular weight.

Example 64

Solubility of Oxidized Cellulose Esters

The solubility of several oxidized cellulose esters were evaluated to determine solubility in solvents commonly utilized for coatings applications. Samples were prepared at 10% solids by weight and were designated as soluble (S), soluble with some gels (SG), partially soluble (PS), or insoluble (I). From this example (Table 17), it may be seen that both the composition of the ester substituents and the acid number of the polymers influence solubility.

TABLE 17

Solubility of cellulose ester interpolymers in coating solvents.

| Solvent | Oxidized cellulose acetate (AN = 89) | Oxidized cellulose acetate propionate (AN = 69) | Oxidized cellulose acetate butyrate (AN = 12) | Oxidized cellulose acetate butyrate (AN = 104) |
|---|---|---|---|---|
| Ethylene glycol monobutyl ether | I | S | I | S |
| Acetone | I | S | I | S |
| Methyl ethyl ketone | S | S | I | I |
| Methanol | I | S | S | S |
| Butyl acetate | I | SG | I | S |
| Ethylene glycol monobutyl ether acetate | I | SG | I | I |
| Propylene glycol monomethyl ether acetate | SG | S | I | S |

Example 65

Preparation of Waterborne Solutions of Oxidized Cellulosics

A typical waterborne cellulose ester such as carboxymethyl cellulose acetate butyrate (Eastman Chemical, CMCAB) may be solubilized in water using a combination of solvent, water, and amine. As the proportion of solvent in the aqueous solution of cellulose ester increases at constant solids content, the viscosity of the solution decreases. It was determined that an aqueous solution of oxidized cellulose acetate butyrate (acid number=104) prepared at 10% solids with 100% neutralization of the acid functionality with dimethylethanolamine (Aldrich) was directly soluble in water and low in viscosity without the need for additional solvent. In this example, 5.4 grams of deionized water was combined with 0.6 grams of oxidized cellulose acetate butyrate and 0.099 grams of dimethylethanol amine and allowed to roll overnight to yield a clear, very light yellow solution with low viscosity.

Example 66

Drug Dissolution from Tablets Consisting Oxidized Cellulose Acetate

Oxidized cellulose acetate (3.7 g, acid number=88) and 1.5 g NF aspirin were milled in a SPEX liquid nitrogen freezer mill for 6 minutes at 75% maximum speed. Magnesium stearate powder (0.04 g) which had been dispersed in carbon black (0.13 g carbon black to 1.0 g magnesium stearate) was added to the powder and mixed until an even pale gray color was achieved. Tablets (0.34-0.37 g) were pressed individually using a tablet press at 5000 psi. Likewise, 6.0 g of cellulose diacetate (CA-398-30) powder was milled with 1.5 g NF Grade aspirin with 0.04 g Mg stearate/carbon black added. Tablets (0.32-0.37 g) tablets were also pressed at 5000 psi.

The dissolution test was completed using a USP #2 calibrated apparatus with Teflon paddles. Buffer solutions were degassed at 41° C. through a 0.45 micron nylon filter and held under vacuum for an additional 5 minutes. After adding the solutions to the dissolution vessels, the solutions were held at 37.3° C. for 30 minutes to achieve constant temperature. The tablets were added to 900 ml of USP 1.2 pH buffer or to 900 ml of USP pH 6.8 buffer. The tablets were weighted down with a Varian 3-pronged capsule weight. At the beginning of each experiment, the tablets were allowed to sink to the bottom of the 1000 ml vessel, the stirrers were turned on at 50 rpm and samples taken as a function of time, using polypropylene syringes. The samples were filtered through 0.45 micron filters and immediately analyzed for the amount of aspirin in the solution using a Varian UV-Vis Spectrophotometer and quartz absorption cells. The wavelengths for measuring the amount of salicylic acid at pH 1.2 and 6.8 was 278 nm and 235, respectively. Each set of experiments had appropriate standards for reference for quantitative analysis.

During the first hour of the experiments, the oxidized cellulose acetate (CAOX) tablets formed cracks at pH 1.2 but retained their original shape at pH 6.8. After 3 hours, the CAOX tablets in pH 6.8 buffer solution had almost completely disappeared leaving a clear solution. At pH 1.2, the CAOX tablets retained the same shape that they had achieved after 10 minutes in the buffer solution. In contrast to both, the CA-398-30 tablets did not change shape through the course of the experiment at pH 1.2 or pH 6.8.

Figure 5:
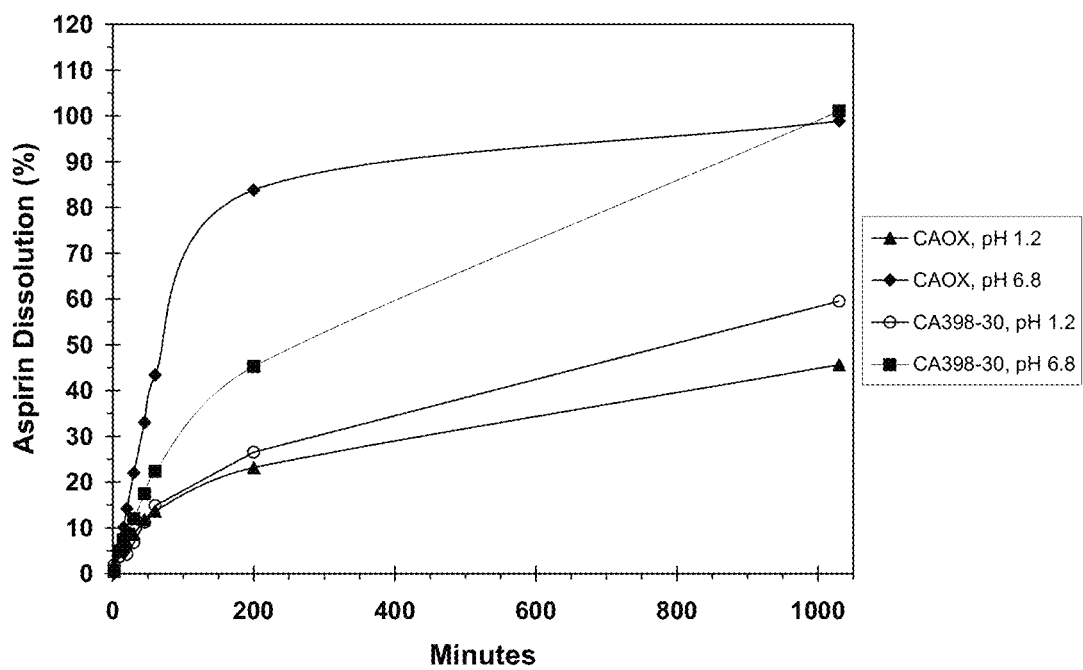
FIG. 5 is a plot of dissolution versus time (minutes) for aspirin in compressed tablets with oxidized cellulose acetate at pH 1.2 and 6.8 at 37° C.

FIG. 5 summarizes the results of these experiments. After 200 min at pH 1.2, only 23% of the maximum amount of aspirin had been released from the intact CAOX tablets. In contrast, at pH 6.8 84% of the maximum available aspirin was released into the media. In the case of the CA398 tablets, 27% and 45% of the available aspirin was released at 200 min at pH 1.3 and 6.8 respectively. This illustrates that the CAOX has low solubility at pH 1.2 and is sufficiently hydrophobic to prevent significant release of the highly water soluble aspirin by diffusion. At pH 6.8, the CAOX dissolved releasing the drug from the matrix. In contrast, the tablets made from cellulose acetate remained intact at this pH 6.8 and only 45% of the drug was released by a diffusion controlled process.

This example illustrates that the oxidized cellulose esters of the present invention can be used to form tablets by compression molding. Because the tablet structure is sensitive to pH, lowered amounts of the drug is released at pH 1.2 (normal stomach pH) while at higher pH (the normal pH gradient of the small intestine is 4.5-7.2), high amounts of the drug is released. This type of formulation is particularly useful in providing controlled release of drug actives in the intestine as opposed to the harsh environment of the stomach. That is, the oxidized cellulose esters of this invention act as release rate modifiers.

Example 67

Oxidized Cellulose Acetate Blends with Poorly Water-Soluble Drugs

A solution of oxidized cellulose acetate (acid number=88) was prepared by adding 400 mg of CA to 15 g of pH 4.8 0.1 N citrate buffer. The heterogeneous mixture was mixed well before carefully adjusting the pH with 0.1 N NaOH until the CA dissolved giving a clear solution. The pH of the aqueous CA solution was found to ca. 3.8. Four independent aqueous CA solutions were prepared by this process. Concurrently, independent solutions containing 40-41 mg of ritonavir, anastrozole, tamoxifen, or letrozole were prepared by dissolving each drug in 5 mL of absolute ethanol. Each of these drugs has poor water solubility. The ethanol solution of each drug was then added slowly to the aqueous CA solutions previously prepared. After addition of each drug solution, the pH of each solution was measured and found to be 4.0-4.3. The oxidized CA:drug solutions were then freeze dried which provided white powders of each mixture.

Solutions of each of the oxidized CA:drug mixtures were prepared in Millipore water (23.0-26.5 g/L). All of the samples were filtered thru 0.45 micron syringe filters before measurement. The pH of each solution after filtration ranged from 3.9-4.1. Solutions of each of the oxidized CA:drug mixtures were also prepared in 50/50 ethanol/Millipore water. All of the oxidized CA:drug mixtures dissolved in the ethanol/water mixture providing clear solutions thus allowing determination of the maximum amount of drug that can be observed with each sample. All samples were immediately analyzed for the amount of drug in the solution using an UV-Vis Spectrophotometer. The results are summarized in Table 18 which gives the % drug solubilized based on the maximum amount possible when the oxidized CA:drug mixture was redissolved in water. Also given is the ratio of the amount of drug solubilized (Sw) to the intrinsic solubility of the drug (So).

TABLE 18

Solubilization of poorly water-soluble drugs with cellulose ester interpolymers.

| Drug | % Drug Solubilized | Sw (g/L/25 g of drug:CAOX) | So (g/L) | Sw/So | Drug pKa (calculated) |
|---|---|---|---|---|---|
| ritonavir | 28 | 0.5360 | 0.0218 | 24.6 | 3.48, 11.5 |
| anastrozole | 90 | 1.2481 | 0.6500 | 1.9 | 4.78 |
| tamoxifen | 89 | 1.1215 | 0.0006 | 1869 | 8.69 |
| letrozole | 7 | 0.1461 | 0.1200 | 1.2 | 3.63 |

The results summarized in Table 18 illustrate a number of useful points. With this set of conditions, 28% of the ritonavir in the pharmaceutical formulation was solubilized when dissolved in water which represents a 24.6 fold increase in ritonavir solubility when measured in the absence of the oxidized cellulose acetate. In the case of anastrozole, the % drug solubilized was 90% while Sw/So was 1.9. With tamoxifen, % drug solubilized was 89% and Sw/So was 1869. For tamoxifen, this data illustrates that the oxidized CA was both efficient in solubilizing the drug while providing a very significant increase in tamoxifen solubility. In the case of letrozole, the efficiency (7% drug solubilized) and Sw/So (1.2) were relatively low.

Also shown in Table 18 are the pKa for each of these basic drugs. One should note, that with ritonavir and letrozole, the pH of the formulations and of the aqueous drug solutions were above the pKa of the drug. That is, these basic drugs were not significantly ionized. For both of these drugs, the % drug solubilized was relatively low. In the case of anastrozole, the pH of the formulation and of the aqueous drug solution were very near the pKa of anastrozole. In this case the % drug solubilized is high while Sw/So is relatively low. With tamoxifen, the pH of the formulation and of the aqueous drug solution is ca. 4.6 units less than the pKa of tamoxifen. As noted for tamoxifen, the % drug solubilized and Sw/So are large. Based on the well known Henderson-Hasselbalch equation, one can obtain the following relationship for the basic drugs of this example: $S_{total} = S_{intrinsic}(1 + 10^{(pKa-pH)})$. Therefore, based strictly on the concentration of ionized and unionized form of the drugs, the total solubility is equal to twice the intrinsic solubility when the formulation pH and drug pKa or ca. equivalent. This is what is observed with anastrozole (Sw/So=1.9). For each unit difference between the drug pKa and the formulation pH, the total drug solubility changes by an order of magnitude. In the case of tamoxifen, this is reflected in both % drug solubilized and the large value of Sw/So. In the case of ritonavir, the pKa is less than that the pH media and contribution of the ionized species to the total solubility is small but Sw/So is relatively large. This observation suggests that specific drug:oxidized cellulose acetate interactions, eg. hydrogen bonding, are also contributing to the total solubility. In the case of letrozole, the pKa is also less than that the pH media and the low Sw/So value indicates poor interactions between the drug and the oxidized cellulose acetate.

This example demonstrates that when properly formulated, the cellulose ester interpolymers of the present invention can serve to modify the solubility of drugs in aqueous media. Without wishing to be bound by theory, it is believed that the cellulose ester interpolymers modifies the solubility of drugs by changing the concentration of the ionized species and through specific interactions between the drug and oxidized cellulose ester interpolymer.

Example 68

Drug Dissolution from Capsules Coated with Oxidized Cellulose Acetate

Topac Inc. gelatin capsules (#3, 0.30 ml) with a lock-ring design were filled with approximately 0.17-0.19 g USP grade pure aspirin. The capsules were then dip-coated 3 times with either a cellulose acetate solution (2 g CA398-10 NF, 0.22 g DEP, 20 g acetone, 0.10 g charcoal colorant) or an oxidized cellulose acetate solution (2 g oxidized cellulose acetate (AN=88), 0.22 g DEP, 18 g acetone, 2 g de-ionized water, 0.10 g charcoal colorant) or left uncoated. Charcoal powder was used as a colorant to determine whether or not the capsules were being evenly coated. The coated capsules were allowed to air dry overnight.

The dissolution test was completed using a USP #2 calibrated apparatus with Teflon paddles. Buffer solutions were degassed at 41° C. through a 0.45 micron nylon filter and held under vacuum for an additional 5 minutes. After adding the solutions to the dissolution vessels, the solutions were held at 37.3° C. for 30 minutes to achieve constant temperature. The capsules were added to 900 mL of USP 1.2 pH buffer or to 900 mL of USP pH 6.8 buffer. The tablets were weighted down with a Varian 3-pronged capsule weight. At the beginning of each experiment, the tablets were allowed to sink to the bottom of the 1000 mL vessel, the stirrers were turned on at 50 rpm and samples taken as a function of time, using polypropylene syringes. The experiment was run continuously for 21 hours. The samples were filtered through 0.45 micron filters and immediately analyzed for the amount of aspirin in the solution using a Varian UV-Vis Spectrophotometer and quartz absorption cells. The wavelengths for measuring the amount of aspirin acid at pH 1.2 and 6.8 were 280 nm and 298 nm, respectively. Each set of experiments had appropriate standards for reference for quantitative analysis.

Figure 6:
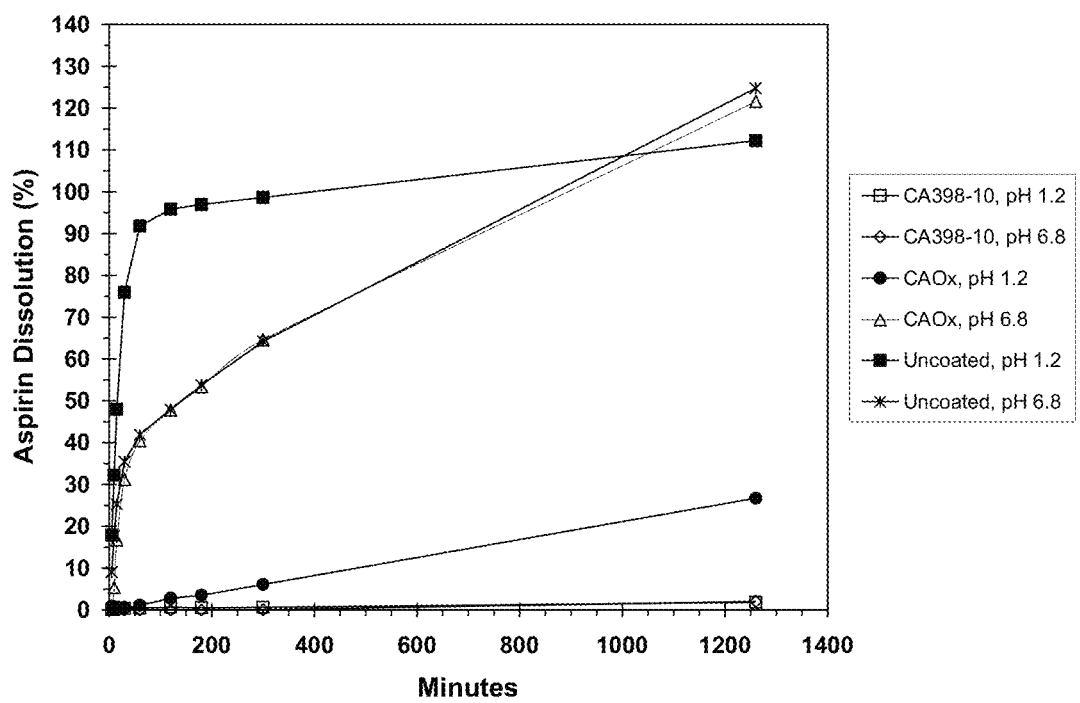
FIG. 6 shows the dissolution of aspirin from coated capsules at 37° C. at pH 1.2 and pH 6.8.

The capsules coated with CA398-10 did not appear to physically change during the course of the experiment. As illustrated in FIG. 6, less than 2% of the aspirin dissolved at both pH 1.2 and pH 6.8 over the course of the experiment. After 300 min at pH 1.2 and 6.8, less than 0.1% of the available aspirin was released into the media.

Different results were obtained with the capsules coated with oxidized cellulose acetate depending on the pH of the experiment. At pH 1.2, the oxidized cellulose acetate coated capsule did not appear to physically change. After 300 min at pH 1.2, less than 10% of the maximum amount of aspirin had been released from the intact coated capsules. At pH 6.8, the oxidized cellulose acetate coated capsule behaved identically to the uncoated capsule at pH 6.8 (FIG. 6). Visually, by 15 minutes, the oxidized cellulose acetate coating had completely disappeared and the gelatin capsule was significantly dissolved. After 300 min at pH 6.8, 65% of the maximum available aspirin was released into the media, precisely the amount of the uncoated capsule.

This example demonstrates the use of oxidized cellulose interpolymers as an enteric coating to prevent drug dissolution at pH 1.2 (pH of the stomach) while permitting rapid drug release at the normal pH of the small intestine (4.5-7.2). Because the capsule coated with the cellulose ester interpolymer is sensitive to pH, lowered amounts of the drug is released at normal stomach pH while at intestinal pH, high amounts of the drug is released. That is, the cellulose ester interpolymers of this invention function as enteric coatings.

Example 69

A solution of oxidized cellulose acetate (acid number=88) was prepared by adding 400 mg of CA to 15 g of pH 4.8 0.1 N citrate buffer. The heterogeneous mixture was mixed well before carefully adjusting the pH with 0.1 N NaOH until the CA dissolved giving a clear solution. The pH of the aqueous CA solution was found to ca. 3.8. Four independent aqueous CA solutions were prepared by this process. Concurrently, independent solutions containing 40-41 mg of ritonavir, anastrozole, tamoxifen, or letrozole were prepared by dissolving each drug in 5 mL of absolute ethanol. Each of these drugs has poor water solubility. The ethanol solution of each drug was then added slowly to the aqueous CA solutions previously prepared. After addition of each drug solution, the pH of each solution was measured and found to be 4.0-4.3. The oxidized CA:drug solutions were then freeze dried which provided white powders of each mixture.

Solutions of each of the oxidized CA:drug mixtures were prepared in Millipore water. Sufficient oxidized CA:drug mixture was added so that the expected drug concentration was 12-125 mg/L. The pH of each solution ranged from 4.2-5.7. In the case of ritonavir, the sample was filtered thru 0.45 micron syringe filter before measurement. No filtration was required for the other samples (clear solutions with no visible solids). The samples were immediately analyzed for the amount of drug in the solution using an UV-Vis Spectrophotometer.

FIG. 7 summarizes the results obtained in this experiment

Example 70

Waterborne Coating Formulation containing an oxidized Cellulose Ester of the invention was prepared as described below;

|  | Grams |  |
|---|---|---|
| Maincote HG-56 w/ 2.5% Oxidized CAB Grind: |  |  |
| DPM | 3.6 | Dow Chemical |
| Water | 7 |  |
| Tamol 165 | 1.9 | Rohm & Haas |
| Ammonia (28%) | 0.2 |  |
| Triton CF-10 | 0.3 | Rohm & Haas |
| *15% Oxidized CAB Solution | 8.716 |  |
| Tego 1488 | 0.3 | Tego Chemie |

|  | Grams | |
|---|---|---|
| Ti-Pure R706 | 39 | DuPont |
| Cowles Grind to 7+ Hegman, then add at low speed: | | |
| Water | 1 | |
| | 62.016 | |
| Letdown: | | |
| Maincote HG-56 | 104.6 | Rohm & Haas |
| Ammonia (28%) | 0.8 | |
| Premix then add: | | |
| DPnB | 11 | Dow Chemical |
| Water | 17 | |
| Dibutyl Phthalate | 2.8 | Eastman Chemical |
| Tego 1488 | 0.5 | Tego Chemie |
| Sodium Nitrite | 1.8 | |
| Acrysol RM-8W | 0.6 | Rohm & Haas |
| | 201.116 | |

*Oxidized CAB sample from Example 63 was dispersed in 8 grams Eastman EB Solvent/77 Grams of Water giving 15% solids with DMEA to pH 8

The resulting formulation was tested for sag resistance using ASTM D4400-898. The paint showed significantly improved sag resistance relative to a control which did not contain the oxidized cellulose ester. (CAB refers to cellulose acetate butyrate available from Eastman Chemical Company).

While the invention has been described with reference to preferred embodiments and working examples, it is to be understood that variations and modifications may be resorted to as will be apparent to those skilled in the art. Such variations and modifications are to be considered within the purview and scope of the invention as defined by the claims appended hereto.

We claim:

1. A method for converting a primary alcohol to a formyl carboxylate, or mixture thereof, comprising:
    adding a 4-substituted piperidine nitroxyl derivative, a primary oxidant, and a terminal oxidant to a homogeneous solution to form a reaction mixture, wherein the homogeneous solution has a pH of less than about 4 and comprises a cellulose interpolymer comprising a primary alcohol functional group;
    passing of a reaction period sufficient to affect conversion of the primary alcohol functional group to a formyl group or a carboxy group and thus produce an oxidized cellulose interpolymer, wherein the oxidized, cellulose interpolymer consists of anhydroglucose units;

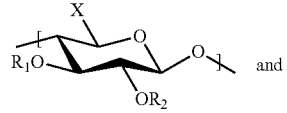
(A)

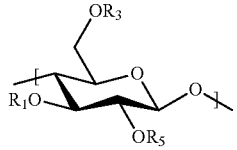
(B)

as the non-terminal monomer units of the oxidized cellulose interpolymer, wherein $R_1$, $R_2$, $R_3$, $R_4$, and $R_5$ are independently selected from the group consisting of hydrogen and $C_2$-$C_{12}$ acyl groups, and X is formyl or carboxy.

2. The method of claim 1, wherein the primary oxidant is a Mn(III) sat.

3. The method of claim 2, wherein the Mn(III) salt is manganese triacetate.

4. The method of claim 1, when the primary oxidant further comprises a salt of Cu, Mg, Fe, Na, K, or mixtures thereof.

5. The method of claim 1, wherein the reaction mixture further comprises water.

6. The method of claim 1, wherein the reaction mixture further comprises water and a $C_2$-$C_{12}$ alkyl acid.

7. The method of claim 1, wherein the 4-substituted piperidine nitroxyl derivative is a 4-amino substituted 2,2,6,6-tetramethyl piperidin-1-oxyl derivative.

8. The method of claim 1, wherein the 4-substituted piperidine nitroxyl derivative is 4-amino 2,2,6,6-tetramethyl piperidin-1-oxyl.

9. The method of claim 1, wherein the 4-substituted piperidine nitroxyl derivative is a 4-($C_1$-$C_4$ acetamido)-2,2,6,6-tetramethylpiperidin-1-oxyl.

10. The method of claim 1, wherein the 4-substituted piperidine nitroxyl derivative is 4-acetamido-2,2,6,6-tramethylpiperidin-1-oxyl.

11. The method of claim 1, wherein the 4-substituted piperidine nitroxyl derivative is immobilized on an inert resin.

12. The method of claim 1, wherein the oxidized cellulose interpolymer has an acid number greater than 30.

* * * * *